(12) United States Patent
Kang et al.

(10) Patent No.: US 8,883,754 B2
(45) Date of Patent: Nov. 11, 2014

(54) METHOD FOR INHIBITING ANGIOGENESIS

(75) Inventors: Sang Won Kang, Seoul (KR); Dong Hoon Kang, Gyeonggi-do (KR); Doo Jae Lee, Seoul (KR)

(73) Assignee: Ewha University—Industry Collaboration Foundation, Seoul (KR)

( * ) Notice: Subject to any disclaimer, the term of this patent is extended or adjusted under 35 U.S.C. 154(b) by 0 days.

(21) Appl. No.: 13/536,213

(22) Filed: Jun. 28, 2012

(65) Prior Publication Data

US 2012/0328617 A1  Dec. 27, 2012

Related U.S. Application Data

(63) Continuation-in-part of application No. PCT/KR2010/009540, filed on Dec. 29, 2010.

(30) Foreign Application Priority Data

Dec. 29, 2009 (KR) .......................... 10-2009-0132296

(51) Int. Cl.
*C07H 21/04* (2006.01)
*G01N 33/50* (2006.01)
*A61K 31/713* (2006.01)

(52) U.S. Cl.
CPC .......... *A61K 31/713* (2013.01); *G01N 33/5023* (2013.01)
USPC .......................................... 514/44; 536/24.5

(58) Field of Classification Search
CPC combination set(s) only.
See application file for complete search history.

(56) References Cited

U.S. PATENT DOCUMENTS

2005/0233992 A1  10/2005  Itescu .............................. 514/44
2011/0177091 A1*  7/2011  Gollnick et al. ........... 424/155.1

OTHER PUBLICATIONS

Immenschuh et al. (Antioxidants & Redox Signaling, 2005, vol. 7: 768-777).*
Shen et al. (Molecular Medicine 2002, vol. 8(2): 95-102).*
Park et al. (Clin. Cancer Res 2000, vol. 6:4915-4920).*
Ewha University, Notice of Preliminary Rejection 10-2010-0138354, 6 pages, Jul. 15, 2013 [*English Translation of Korean 2nd Official Action*].
Joo-Heon Kim, et al., "Up-Regulation of Peroxiredoxin 1 in Lung Cancer and Its Implication as a Prognostic and Therapeutic Target," *Clin. Cancer Res.* 2008; 14: pp. 2326-2333.

* cited by examiner

*Primary Examiner* — Kimberly Chong
(74) *Attorney, Agent, or Firm* — Sunstein Kann Murphy & Timbers LLP

(57) ABSTRACT

The present invention relates to a method for inhibiting angiogenesis using a peroxiredoxin II (Prx II) inhibitor, and a method for preparing angiogenesis-inhibiting medicines using Prx II inhibitor. According to the present invention, the inhibitor of Prx II gene expression or Prx II protein activity increases oxidative inactivation of VEGF receptor tyrosine kinase (RTK) to reduce VEGF signaling, thereby screening a novel angiogenesis inhibitor. Therefore, the method of the present invention can be used for the prevention or treatment of various diseases, ailments, and conditions related to angiogenesis.

9 Claims, 25 Drawing Sheets

METHOD FOR INHIBITING ANGIOGENESIS

CROSS-REFERENCE TO RELATED APPLICATIONS

This application is a Continuation-in-Part of PCT International Application Ser. No. PCT/KR2010/009540, filed Dec. 29, 2010, designating the United States, which claims the benefit of Korean Application No. 10-2009-0132296, filed on Dec. 29, 2009. The entire contents of the aforementioned patent applications are incorporated herein by this reference.

BACKGROUND OF THE INVENTION

1. Field of the Invention

The present invention relates to a method for inhibiting angiogenesis using a peroxiredoxin II (Prx II) inhibitor, and a method for preparing angiogenesis-inhibiting medicines using Prx II inhibitor.

2. Description of the Related Art

In signal transduction pathways involved in vasculature, PDGF/PDGFR-β (platelet-derived growth factor/platelet-derived growth factor receptor-β) and VEGF/VEGFR-2 (vascular endothelial growth factor/vascular endothelial growth factor receptor-2) (also called KDR/Flk-1) signaling pathways are important growth factor signaling pathways that modulate proliferation, chemotactic migration, and survival of VSMCs (Vascular Smooth Muscle Cell) and VECs (Vascular Endothelial Cell) (Olsson, A. K. et al., Nat. Rev. Mol. Cell Biol., 2006 7(5): 359-371; Heldin, C. K. and Westermark, B. Physiol, Rev., 1999 79(4): 1283-1316). VEGFR and PDGFR belong to the same receptor tyrosine kinase (RTK) subclass that has seven extracellular immunoglobulin-like domains, a transmembrane domain, and a split kinase domain. They share many downstream signaling events.

Recently, reactive oxygen species (ROS) such as superoxide ($O_2^-$) and hydrogen peroxide ($H_2O_2$) are known to perform a pivotal function as a secondary mediator in receptor-mediated signaling (Rhee, S. G., Science, 2006 312(5782): 1882-1883; Finkel, T. Curr. Opin. Cell Biol., 2003 15(2): 247-254). Interestingly, PDGF is the first growth factor inducing generation of intracellular ROS in vascular smooth muscle cells (VSMC) (Sundaresan, M. et al., Science, 1995 270(5234): 296-299). In the previous pioneering studies of the present invention, catalase was used to reveal that ROS, $H_2O_2$ is induced by growth factors, and participates in receptor-mediated signaling. Subsequently, a relationship between the receptor-mediated ROS production and its downstream signal transduction pathways was reported (Lander, H. M. FASEB J., 1997 11(2): 118-124), and numerous studies suggested that the oxidative inactivation of protein tyrosine phosphatases (PTPs) is located downstream of the above described signaling pathways (Rhee, S. G. et al., Sci. STKE., 2000: 2000(53)). ROS is also involved in VEGF/VEGFR-2 signaling as well as in angiogenesis (Roy, S. et al., Free Radic. Biol. Med., 2008 44(2): 180-192; Abid, M. R. et al., J. Biol. Chem., 2007 282(48): 35373-35385; Colavitti, R. et al., J. Biol. Chem., 2002 277(5): 3101-3108). It was suggested that NADPH oxidase is a ROS-generating enzyme in two RTK (VEGFR and PDGFR) signaling pathways (Ushio-Fukai, M. Antioxid. Redox Signal., 2007 9(6): 731-739; Bae, Y. S. et al., J. Biol. Chem., 2000 275(14): 10527-10531). However, there have been no studies on endogenous ROS regulators and mode of ROS action in VEGF signaling pathways.

Mammalian 2-cys peroxiredoxin (2-cys Prx) groups, belonging to the superfamily of alkyl peroxide reductase/Prx oxidoreductase, are a new type of oxidoreductase that reduces ROS into its corresponding alcohols. They reduce $H_2O_2$ into water using electrons produced from an electron-conveying system consisting of thioredoxin and thioredoxin reductase (Rhee, S. G. et al., Curr. Opin. Cell Biol., 2005 17(2): 183-189). Among five mammalian 2-cys Prx isoforms, two cytosolic isoforms, Prx I and Prx II are reported to be involved in receptor-mediated signaling pathway (Rhee, S. G. et al., Curr. Opin. Cell Biol, 2005 17(2): 183-189). In particular, the present inventors recently revealed that Prx II is a negative endogenous regulator of $H_2O_2$-mediated protein tyrosine phosphorylation in PDGF signaling (Choi, M. H. et al., Nature, 2005 435(7040): 347-353). According to this report, intracellular $H_2O_2$ level is increased and autophosphorylation of PDGFR-β at positions Tyr 857 and Tyr 579/581 is selectively increased in response to PDGF-BB in Prx II-deficient embryonic fibroblasts and vascular SMCs. Subsequently, phospholipase C-γ1 activity is increased, and cell proliferation and chemotactic migration are increased in response to PDGF-BB. It was also suggested that the inactivation-reactivation cycle of membrane PTF (Protein-Tyrosine Phosphatase) is located downstream of selective regulation of PDGFR-β phosphorylation by Prx II (Kang, S. W. et al., Trends Mol, Med., 2005 11(12): 571-578).

Meanwhile, studies for inhibiting angiogenesis have been focused on inhibition of VEGF (vascular endothelial growth factor) signaling. In fact, studies have shown that tumor cells are inhibited at an early stage, but often become more aggressive after anti-angiogenic therapy. Further, the conventional angiogenesis inhibitors inhibit even the delivery of other anti-cancer agents into tumor cells, and consequently tumor cells become more aggressive.

The present inventors have made many efforts to develop a novel angiogenesis inhibitor. They found that deficiency of intracellular 2-cys peroxiredoxin (2-cys Prx), especially, peroxiredoxin II (Prx II), suppresses VEGF-induced angiogenesis so as to inhibit angiogenesis and induce cancer cell death simultaneously, unlike the known mechanism inhibiting angiogenesis only. Therefore, they also found that angiogenesis inhibition and cancer cell death can be simultaneously achieved by inhibition of one target, and various angiogenesis-related diseases, ailments, or conditions, as well as cancer, can be prevented or treated, thereby completing the present invention.

SUMMARY OF THE INVENTION

An object of the present invention is to provide a method for inhibiting angiogenesis, comprising administering to a subject in need thereof an inhibitor of Prx II (peroxiredoxin II) gene expression or Prx II protein activity.

The subject may suffer from cancer, diabetic retinopathy, retinopathy of prematurity, corneal transplant rejection, neovascular glaucoma, erythrosis, proliferative retinopathy, psoriasis, hemophilic arthropathy, capillary proliferation in atherosclerotic plaques, keloid, wound granulation, vascular adhesions, rheumatoid arthritis, ostarthritis, autoimmune diseases, Crohn's disease, restenosis, atherosclerosis, intestinal adhesions, cat scratch disease, ulcer, cirrhosis, glomerulonephritis, diabetic nephropathy, malignant nephrosclerosis, thrombotic microangiopathy, organ-transplant rejection, glomerulopathy, diabetes, inflammatory diseases or neurodegenerative diseases.

The inhibitor may be identified by a screening method comprising the following steps:
(a) reacting a test material with a buffer solution containing Prx II protein, thioredoxin (Trx), thioredoxin reductase (TrxR) and NADPH;

(b) reacting the reaction product of step (a) with $H_2O_2$ to prepare a first experimental group;
(c) reacting a buffer solution containing Prx II protein, thioredoxin (Trx), thioredoxin reductase (TrxR) and NADPH with $H_2O_2$ to prepare a first control group;
(d) measuring and comparing the absorbance of the first experimental group and the first control group; and
(e) determining the test material as an inhibitor when the absorbance of the first experimental group is lower than that of the first control group.

The inhibitor may be identified by a screening method comprising the following steps:
(a) reacting a test material with a buffer solution containing Prx II protein, thioredoxin (Trx), thioredoxin reductase (TrxR) and NADPH;
(b) reacting the reaction product of step (a) with $H_2O_2$ to prepare a first experimental group;
(c) reacting a buffer solution containing Prx II protein, thioredoxin (Trx), thioredoxin reductase (TrxR) and NADPH with $H_2O_2$ to prepare a first control group;
(d) measuring and comparing the absorbance of the first experimental group and the first control group;
(e) reacting the test material with a buffer solution containing one or more protein selected from the group consisting Prx I, III, IV and V, thioredoxin (Trx), thioredoxin reductase (TrxR) and NADPH;
(f) reacting the reaction product of step (e) with $H_2O_2$ to prepare a second experimental group;
(g) reacting a buffer solution containing one or more protein selected from the group consisting Prx I, III, TV and V, thioredoxin (Trx), thioredoxin reductase (TrxR) and NADPH with $H_2O_2$ to prepare a second control group;
(h) measuring and comparing the absorbance of the second experimental group and the second control group; and
(i) determining the test material as an inhibitor when there is no difference in absorbance between the second control group and the second experimental group, while the absorbance of the first experimental group is lower than that of the first control group.

The inhibitor may be identified by a screening method comprising the following steps:
(a) analyzing Prx II protein activity or Prx II gene expression after treatment of a test material; and
(b) determining the test material as an inhibitor when the Prx II protein activity or the Prx II gene expression after the treatment of the test material is inhibited, compared to the non-treatment of the test material.

Another object of the present invention is to provide a method for preparing angiogenesis-inhibiting medicines comprising:
(a) reacting the test material with a buffer solution containing Prx II protein, thioredoxin (Trx), thioredoxin reductase (TrxR) and NADPH;
(b) reacting the reaction product of step (a) with $H_2O_2$ to prepare an experimental group;
(c) reacting a buffer solution containing Prx II protein, thioredoxin (Trx), thioredoxin reductase (TrxR) and NADPH with $H_2O_2$ to prepare a control group;
(d) measuring and comparing the absorbance of the experimental group and the control group;
(e) determining the test material as an inhibitor of Prx II protein activity when the absorbance of the experimental group is lower than that of the control group; and
(f) preparing angiogenesis-inhibiting medicines using a pharmaceutically effective amount of the inhibitor and a pharmaceutically acceptable carrier.

The above objects and the advantages of the present invention will be more clearly understood from the following detailed description in conjunction with the claims and accompanying drawings.

In order to achieve the above objects, the present invention provides a pharmaceutical composition for inhibiting angiogenesis, comprising an inhibitor of Prx II (peroxiredoxin II) gene expression or Prx II protein activity as an active ingredient.

Further, the inhibitor is identified by a screening method comprising the steps of (a) analyzing Prx II protein activity or Prx II gene expression after treatment of a test material; and (b) determining the test material as an angiogenesis inhibitor when the Prx II protein activity or the Prx II gene expression after the treatment of the test material is inhibited, compared to the non-treatment, of the test, material. The Prx II protein activity or the Prx II gene expression can be analyzed in vivo or in vitro.

The screening method of the present invention may include the steps of (a) reacting a test material with a buffer solution containing Prx II protein, thioredoxin (Trx), thioredoxin reductase (TrxR) and NADPH; (b) reacting the reaction product of step (a) with $H_2O_2$ to prepare a first experimental group; (c) reacting a buffer solution containing Prx II protein, thioredoxin (Trx), thioredoxin reductase (TrxR) and NADPH with $H_2O_2$ to prepare a first control group; (d) measuring and comparing the absorbance of the first experimental group and the first control group; and (e) determining the test material as an inhibitor when the absorbance of the first experimental group is lower than that of the first control group.

The screening method of the present invention may also include the steps of (a; reacting a test material with a buffer solution containing Prx II protein, thioredoxin (Trx), thioredoxin reductase (TrxR) and NADPH; (b) reacting the reaction product of step (a) with $H_2O_2$ to prepare a first experimental group; (c) reacting a buffer solution containing Prx II protein, thioredoxin (Trx), thioredoxin reductase (TrxR) and NADPH with $H_2O_2$ to prepare a first, control group; (d) measuring and comparing the absorbance of the first experimental group and the first control, group; (e) reacting the test material with a buffer solution containing one or more protein selected from the group consisting Prx I, III, IV and V, thioredoxin (Trx), thioredoxin reductase (TrxR) and NADPH; (f) reacting the reaction product, of step (e) with $H_2O_2$ to prepare a second experimental group; (g) reacting a buffer solution containing one or more protein selected from the group consisting Prx I, III, IV and V, thioredoxin (Trx), thioredoxin reductase (TrxR) and NADPH with $H_2O_2$ to prepare a second control group; (h) measuring and comparing the absorbance of the second experimental group and the second control group; and (i) determining the test material as an inhibitor when there is no difference in absorbance between the second control group and the second experimental group, while the absorbance of the first experimental group is lower than that of the first, control group.

Further, the present invention provides a method for preparing angiogenesis-inhibiting medicines comprising: (a) reacting the test material with a buffer solution containing Prx II protein, thioredoxin (Trx), thioredoxin reductase (TrxR) and NADPH; (b) reacting the reaction product of step (a) with $H_2O_2$ to prepare an experimental group; (c) reacting a buffer solution containing Prx II protein, thioredoxin (Trx), thioredoxin reductase (TrxR) and NADPH with $H_2O_2$ to prepare a control group; (d) measuring and comparing the absorbance of the experimental group; and the control group; (e) determining the test material as an inhibitor of Prx II protein activity when the absorbance of the experimental group is lower than that of the control group; and (f) preparing angiogenesis-inhibiting medicines using a pharmaceutically effective amount of the inhibitor and a pharmaceutically acceptable carrier.

Further, the present invention provides a kit for screening angiogenesis inhibitors comprising a Prx II protein and a reaction buffer solution. The kit of the present invention may further comprise thioredoxin, thioredoxin reductase, NADPH and $H_2O_2$.

Further, the present invention provides a method for inhibiting angiogenesis, comprising the step of administering to a subject in need thereof an inhibitor of Prx II gene expression or Prx II protein activity.

Furthermore, the present invention provides a use of the an inhibitor of Prx II gene expression or Prx II protein activity in the preparation of angiogenesis-inhibiting medicines.

BRIEF DESCRIPTION OF THE DRAWINGS

FIG. 2 shows,
- a. Elevation of basal $H_2O_2$ level by Prx II knockdown in HAECs.
- b. Elimination of basal $H_2O_2$ by catalase. HAECs with the Prx II knockdown were incubated with polyethylene glycol (PEG)-conjugated catalase at the indicated doses for 18 hrs (n=3, *P<0.001). Data in the graph show the level of the relative DCF fluorescence averaged from 50-80 cells (means±S.D., n=3, *P<0.01).
- c. Tyrosine site-specific phosphorylation of VEGFR-2 induced by VEGF. The phospho-specific bands were quantified and normalized by the intensities of the corresponding VEGFR-2 bands. Data in the graphs are means±S.D. of the relative band intensities (n=4, *P<0.005, P<0.002, *P<0.0001).
- d. VEGFR-2 RTK activation in VEGF-treated HAECs. The in vitro RTK kinase activities (KA) against VEGFR-2 and GST-PLCγ1 are shown. Bars show means±S.D. of fold induction of RTK activities (n=3, *P<0.005, **p<0.001).

FIG. 3 shows,
- a. VEGFR-2 RTK activation in $H_2O_2$-pretreated HAECs in response to VEGF. Ears in the graph show means±S.D. of fold induction of RTK activities (n=3, *P<0.001).
- b. Restoration of VEGF-dependent VEGFR-2 RTK activation by DTT (Dithiothreitol) reduction. The VEGFR-2 was immunoprecipitated from Prx II siRNA-transfected or $H_2O_2$ (100 μM)-pretreated HAECs that were stimulated with or without VEGF and then incubated with DTT for 10 minutes. The activities were averaged from two independent experiments and plotted as fold increases versus an untreated, sample (lane 1).
- c. Prx II$^{+/+}$ and Prx II$^{-/-}$ MAECs activation in Prx II$^{+/+}$ and Prx II$^{-/-}$ MAECs.
- d. VEGFR-2 activation in PrxI$^{+/+}$ and PrxI$^{-/-}$ MAECs (mouse aortic endothelial cell).
- e. VEGFR-2 activation in Prx II$^{-/-}$ MAECs infected with retrovirus encoding wild-type (WT) or inactive cysteine mutant (CS) of human Prx II. In 3c-3e, a representative set of three independent experiments is shown.

FIG. 4 shows,
- a. differential cysteine labeling of VEGFR-2 with fluorophore-conjugated maleimides from control and Prx II siRNA-transfected HAECs. A representative image is shown. Data in the graph are means±S.D. of the relative fluorescence intensities after being normalized to those of the corresponding VEGFR-2 bands (n=3, *P<0.005).
- b. $H_2O_2$-induced inactivation of mouse VEGFR-2 (mVEGFR2; WT and CS mutants ectopically expressed in 293T cells.
- c. Reversibility of $H_2O_2$-induced inactivation of VEGFR-2 WT and C1199S mutant by DTT reduction. The VEGFR-2 WT and C1199S were immunoprecipitated from $H_2O_2$ (100 μM)-pretreated 293T cells and then incubated with 293T for 10 minutes.
- d. Differential cysteine labeling of the expressed mVEGFR-2 with fluorophore-conjugated maleimides in 293T cells treated with or without $H_2O_2$, as in a (n=3, *P<0.005).
- e. VEGF-induced activation of mVEGFR-2 C1206S mutant in HAECs. Cells were knocked down with the Prx II knockdown. The expressed mVEGFR-2 was immunoprecipitated using anti-HA antibody.
- f. Tube formation of HAECs expressing mVEGFR-2 WT and C1206S. As indicated, VEGFR-2 RTK inhibitor SU5416 (1 μM) was pretreated for 1 hr before VEGF treatment. Data are given in percent of total tube length per field versus untreated control cells (means±S.D., n=8, *P<0.05, **P<0.0.1).

FIG. 5 shows,
- a. changes in $H_2O_2$-induced mobility of mVEGFR-2 WT and CS mutants. Extracts of mVEGFR2-expressing 293T cells were boiled in the presence (R) or absence (NR; of DTT. Red, reduced form; Oxi, oxidized form. 10 mM DTT-treated sample (R) was loaded with the control group of fully reduced form of VEGFR2.
- b. DTT-dependent mobility of endogenous human VEGFR-2 on a denaturing gel. The extracts of HAECs and HUVECs treated with $H_2O_2$ were boiled in the presence of the increasing concentrations of DTT.

FIG. 6 shows,
- a. detection of Prx II, VEGFR2, and NOX4 in lipid raft/caveolae fractions isolated from HAECs treated with or without serum supplemented with VEGF. Fraction numbers and sucrose concentrations are indicated.

b. TEM images of immunogold-stained HAECs. The boxed area in the left image is zoomed out. VEGFR-2 and Prx II are indicated by black and red arrows, respectively.

c. Co-localization of caveolin-1 and NOX4 in the plasma membrane (indicated by arrowheads).

Figure 7:
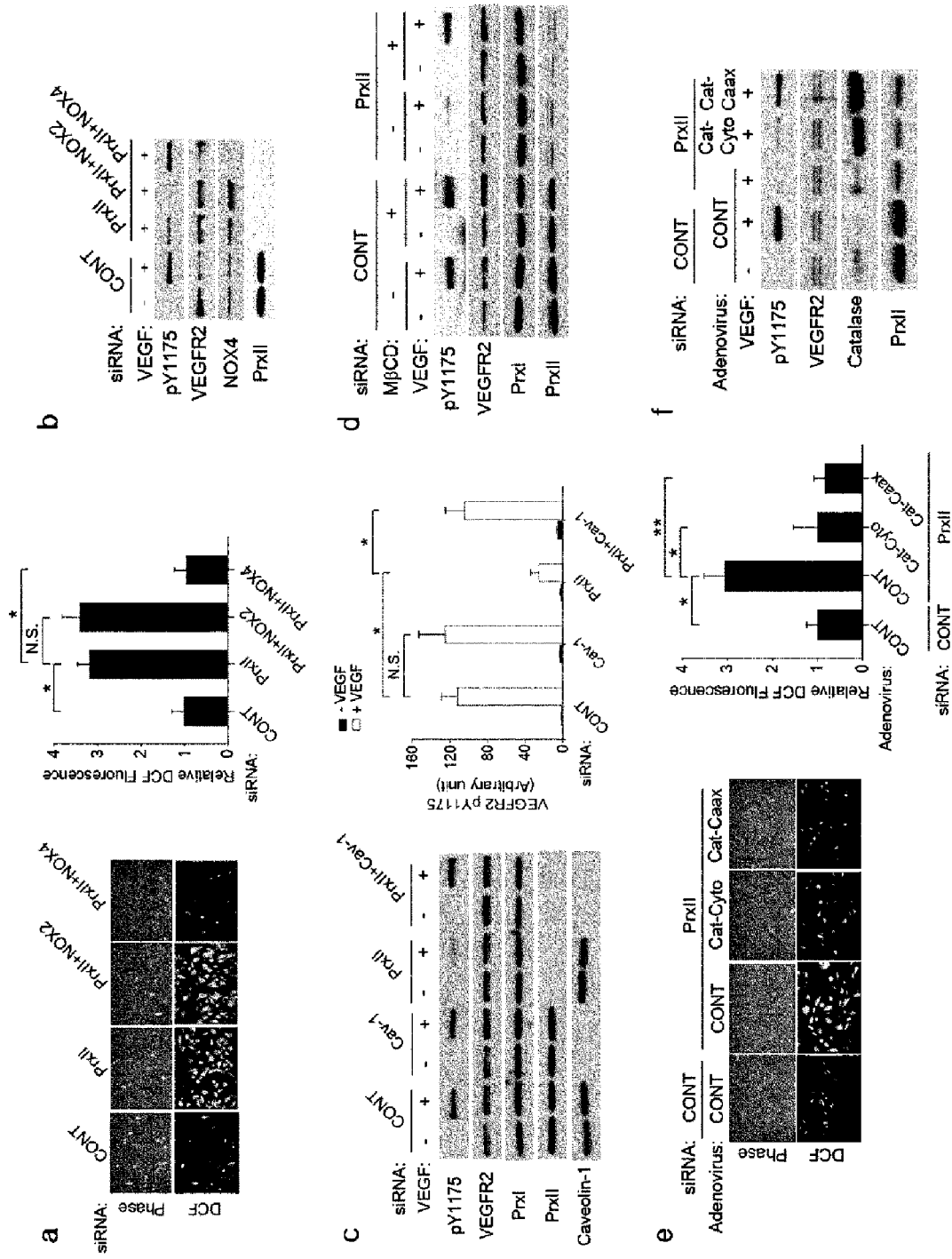

FIG. 7 shows, a. and b. $H_2O_2$ production (a, n=3, *P<0.005) and VEGFR-2 activation (b) in HAECs with the Prx II single knockdown or the Prx II/NOX double knockdown.

c. and d. effect of caveolae disruption by caveolin-1 knockdown (c, n=3, *P<0.001) or cholesterol-hinging agent (d) on VEGFR-2 activation in HAECs. Caveolin-1 knockdown and MβCD treatment was performed for 20 hours and 12 hours, respectively, before VEGF treatment.

e. and f. $H_2O_2$ production (e, n=3, *P<0.005, **P<0.001) and VEGFR-2 (f) activation in the Prx II-knockdown HAECs infected with the indicated adenovirus encoding catalase. Cat-Cyto, cytosolic catalase; Cat-Caax, caveolae-targeted catalase. A representative set of three independent experiments is shown.

Figure 8:
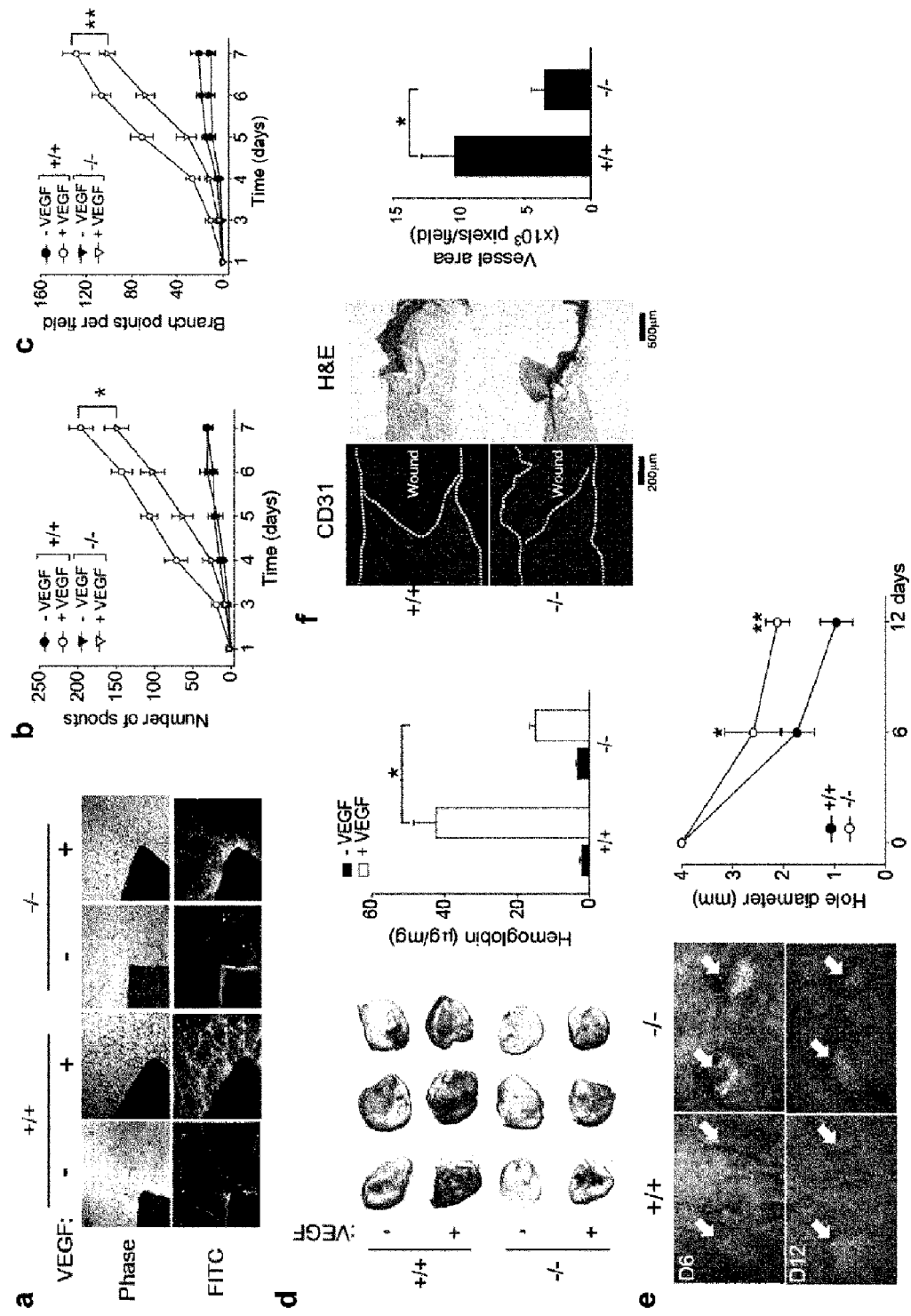
Figure 9:
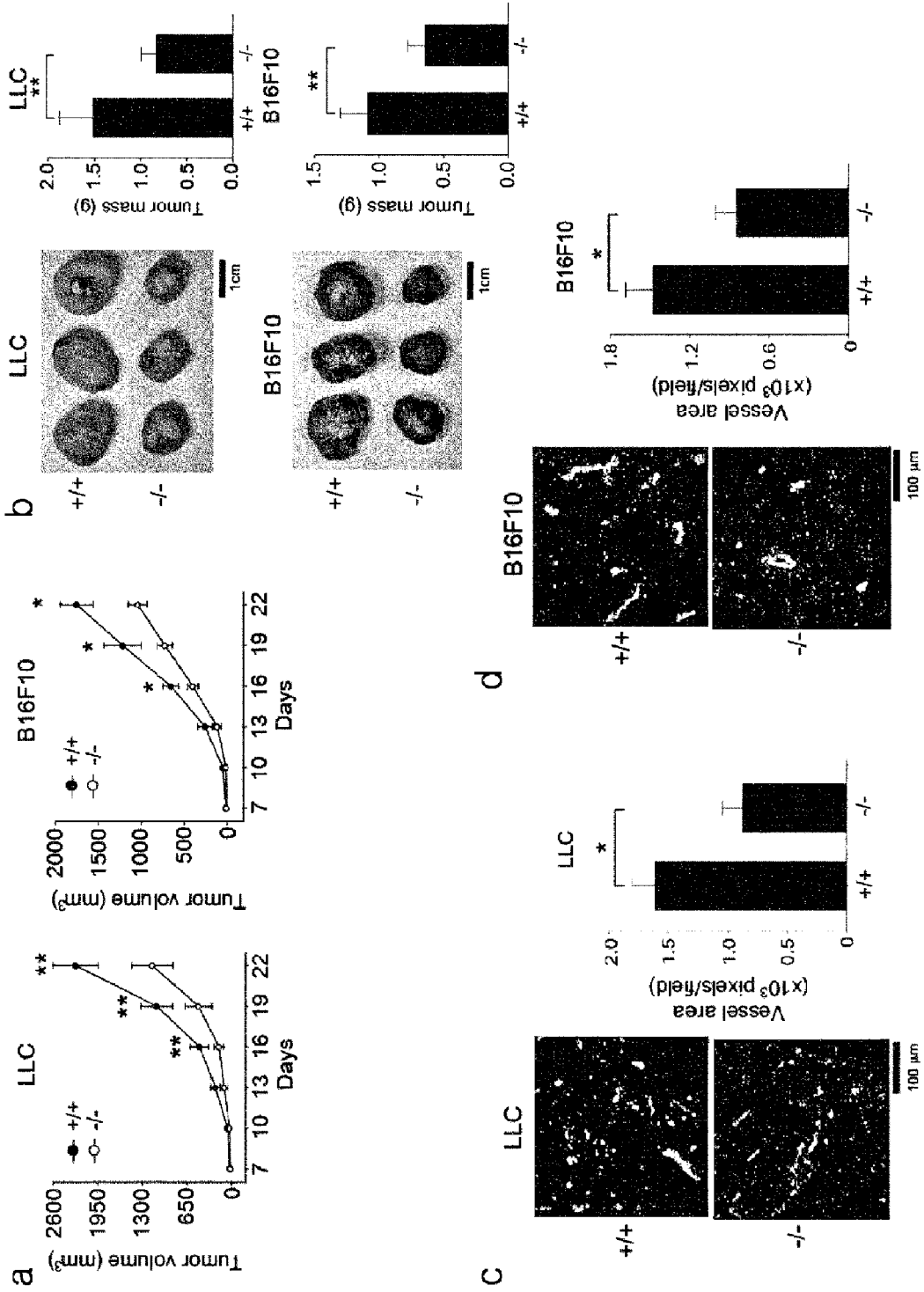
Figure 10:
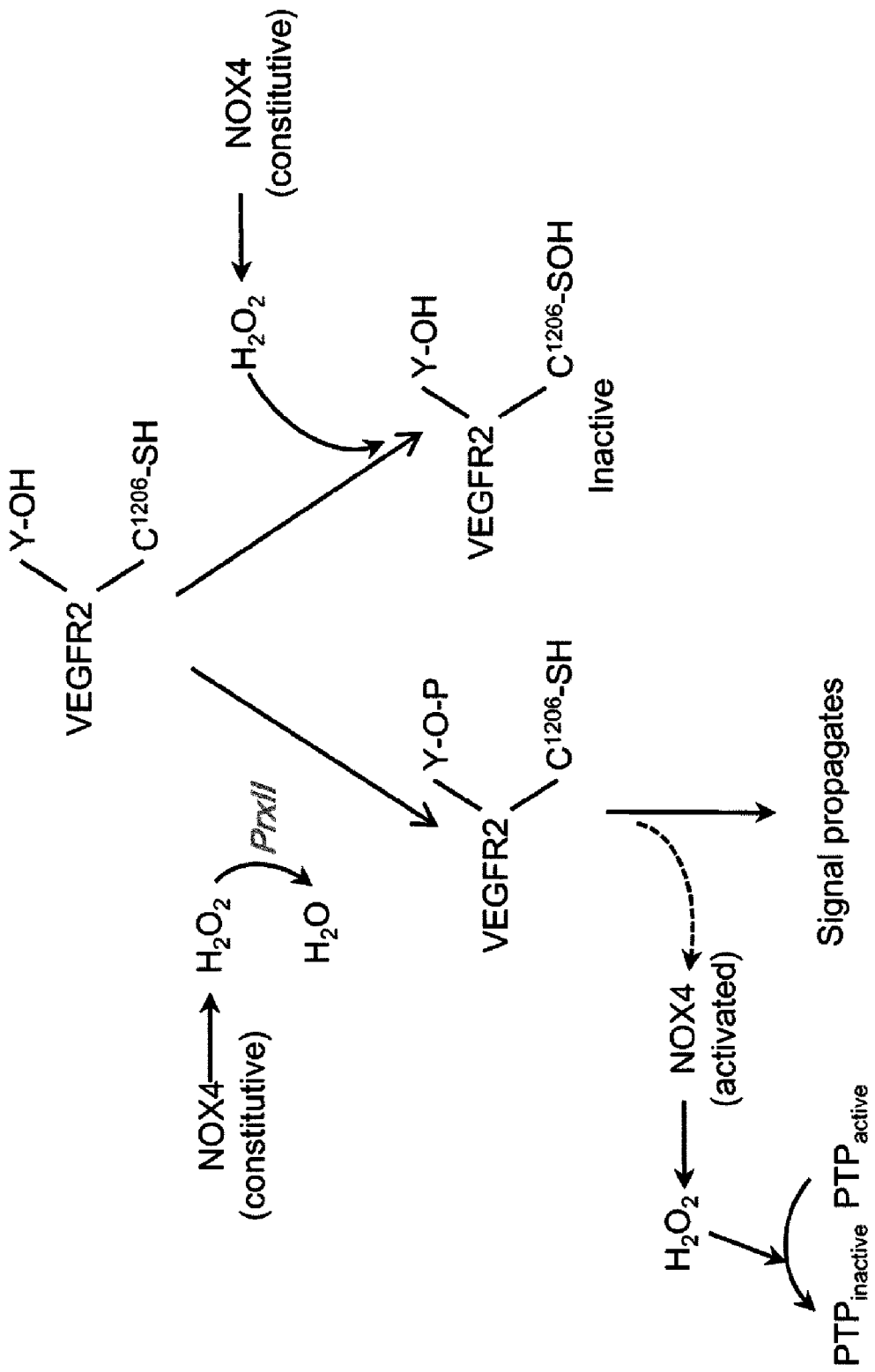

FIGS. 8-10 show that Prx II deficiency reduces angiogenesis in wounded regions and tumors.

FIG. 8 shows, a.-c. microvessel outgrowth from aortic rings of Prx II$^{+/+}$ and Prx II$^{-/-}$ mice. The cells growing out of aortic explants at day 5 were stained with FITC-lectin. Representatives of phase contrast and fluorescence images (a) are shown. The number of sprouts (b) and branch points (c) were counted, from each image (mean±S.D., n=6, *P<0.05, **P<0.01).

d. VEGF-induced neovascularization in the Matrigel plugs implanted to the Prx II$^{+/+}$ and Prx II$^{-/-}$ mice. Angiogenesis is quantified by measuring hemoglobin content in Matrigel plugs (mean±S.D., n=5, *P<0.01). A representative picture of Matrigel plugs is shown.

e. Wound healing in the skins of Prx II$^{+/+}$ and Prx II$^{-/-}$ mice. Representative pictures of wounding areas (Arrows) at 6 and 12 days are shown. The hole diameter was measured by wound perimeter tracing (n=5 mice per group, *P<0.005, **P<0.001).

f. Vessel density at the early wound (6 days). Vessel area represents number of CD31$^+$ pixels per field (n=5 mice per group, *P<0.005). Representative H&E and CD31 staining images are shown.

FIG. 9 shows, a. and b. tumor growth in Prx II$^{+/+}$ and Prx II$^{-/-}$ mice implanted with Lewis lung carcinoma (LLC) and B16F10 melanoma cells. At 22 days, tumor tissues were removed, weighed and photographed with a digital camera. Tumor size is shown by volume (n=16 mice per group, *P<0.05, **P<0.01) and weight (n=10 mice per group, *P<0.01).

c. and d. Vessel density in two-week tumors of similar size. Vessel area represents number of CD31$^+$ pixels per field (n=6 mice per group, *P<0.01). A representative image is shown. In 8e-9d, data are means±S.E.M.

FIG. 10 shows a schematic model for $H_2O_2$ signalosome consisting of Prx II, VEGFR2, and NOX4 in ECs. Since NOX4 is known to be constitutively active, the mechanism of VEGF-dependent NOX4 activation is unknown thus far. Y, C, and P denote tyrosine, cysteine, and phosphate, respectively.

Figure 11:
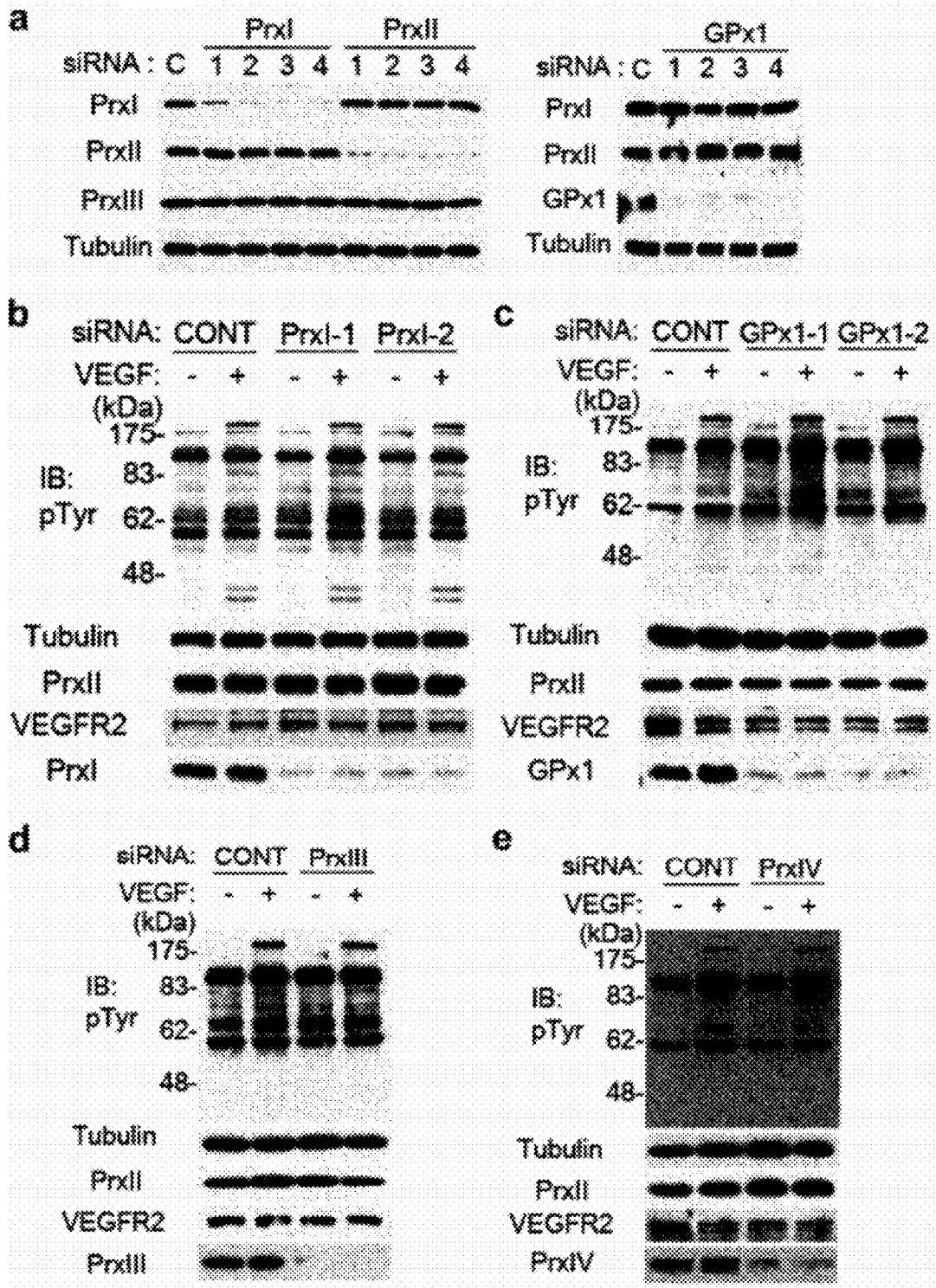

FIG. 11 shows VEGFR tyrosine phosphorylation in HAECs with knockdown of antioxidant enzymes.

a. Knockdown of Prx I, Prx II, and GPxl in HAECs using specific siRNAs. A siRNA specific to firefly luciferase (CONT) was used as control.

b.-e. VEGFR tyrosine phosphorylation in HAECs transfected with siRNAs specific to Prx I (b), GPxl (c), Prx III (d), and Prx IV (e). A representative set of three independent experiments is shown.

Figure 12:
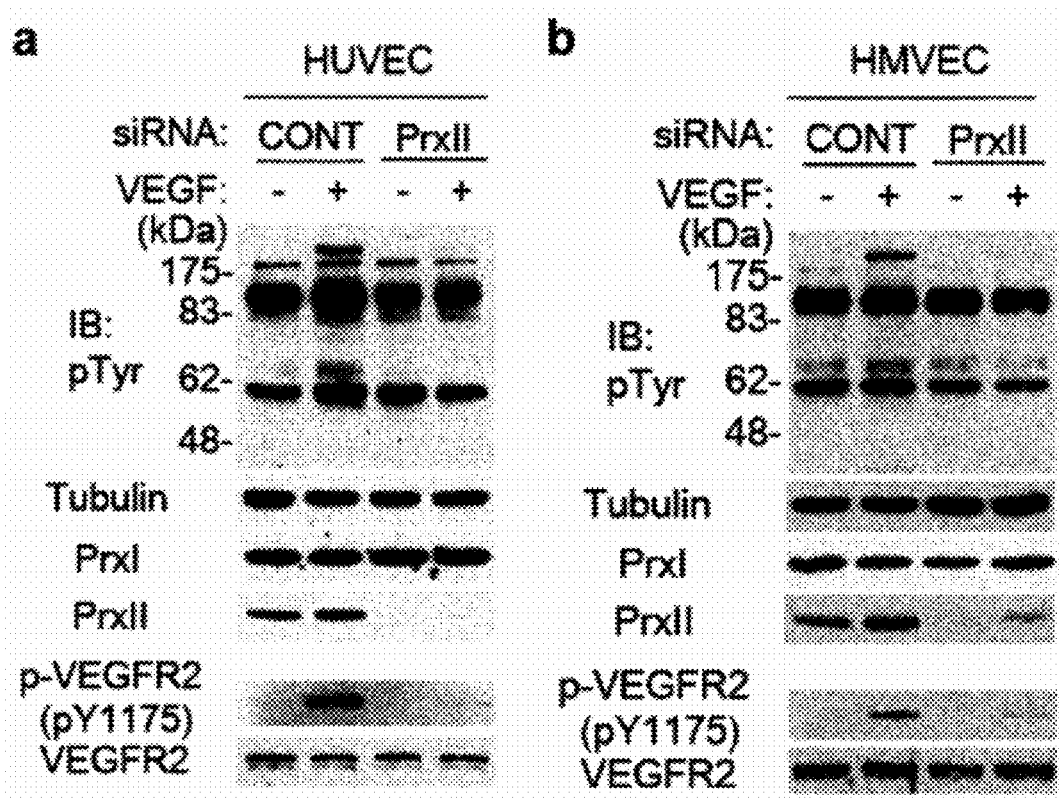

FIG. 12 shows the effect of Prx II knockdown on VEGFR signaling in HUVECs (a) and HMVECs (b).

The HUVECs and HMVECs were transfected with either control siRNA or Prx II siRNA for 24 hrs and then serum-starved in the specified media containing 0.5% FBS for 18 hours. Thereafter, cells were stimulated with VEGF (25 ng/mL) for 10 minutes and then lysed for immunoblotting. A representative set of three independent experiments is shown.

Figure 1:
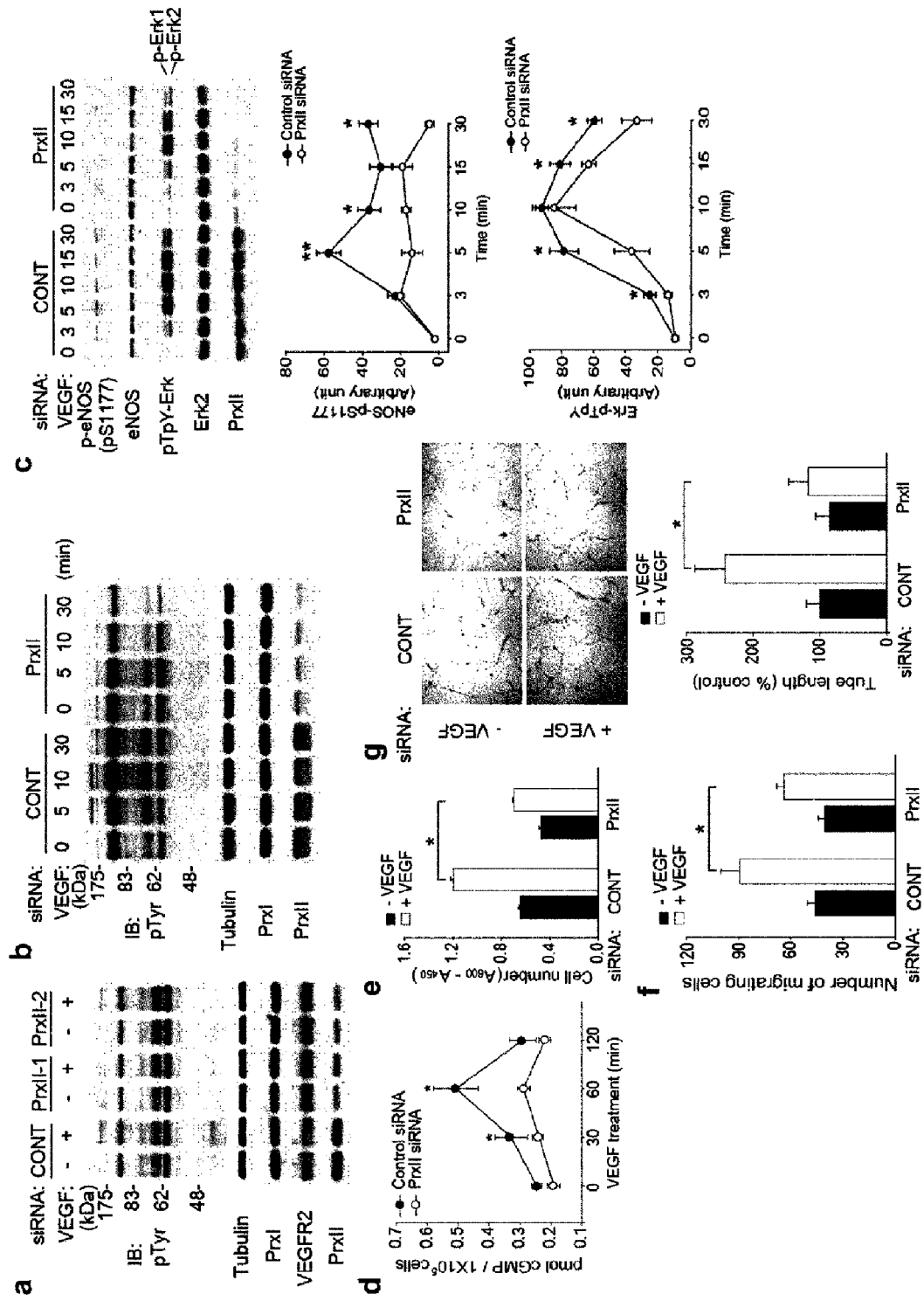
FIG. 1 shows that Prx II knockdown reduces responsiveness of endothelial cell to VEGF.
- a. and b. Immunoblot analysis (IB) of VEGF-induced tyrosine phosphorylation in HAECs (human aortic endothelial cells) with Prx II knockdown. Total tyrosine phosphorylation (pTyr) was detected by anti-phospho-Tyr antibody (4G10).
- c. Activation of endothelial nitric oxide synthase (eNOS) and mitogen-activated protein kinase (MAPK, ERK) in VEGF-treated HAECs. Data in the graphs are means±S.D, of the relative intensities of the phosphospecific bands after being normalized by the intensities of the corresponding non-phospho bands (n=5, *P<0.005, **P<0.002).
- d. Measurement of cyclic GMP levels in HAECs (n=4, *p<0.02).
- e. and f. VEGF-dependent HAEC proliferation (e) and chemotactic migration (f) (n=3, *P<0.005).
- g. VEGF-induced tube formation. Data are given in percent of total tube length per field versus control cells. Bars in the graphs (e-g) show means±S.D.
Figure 13:
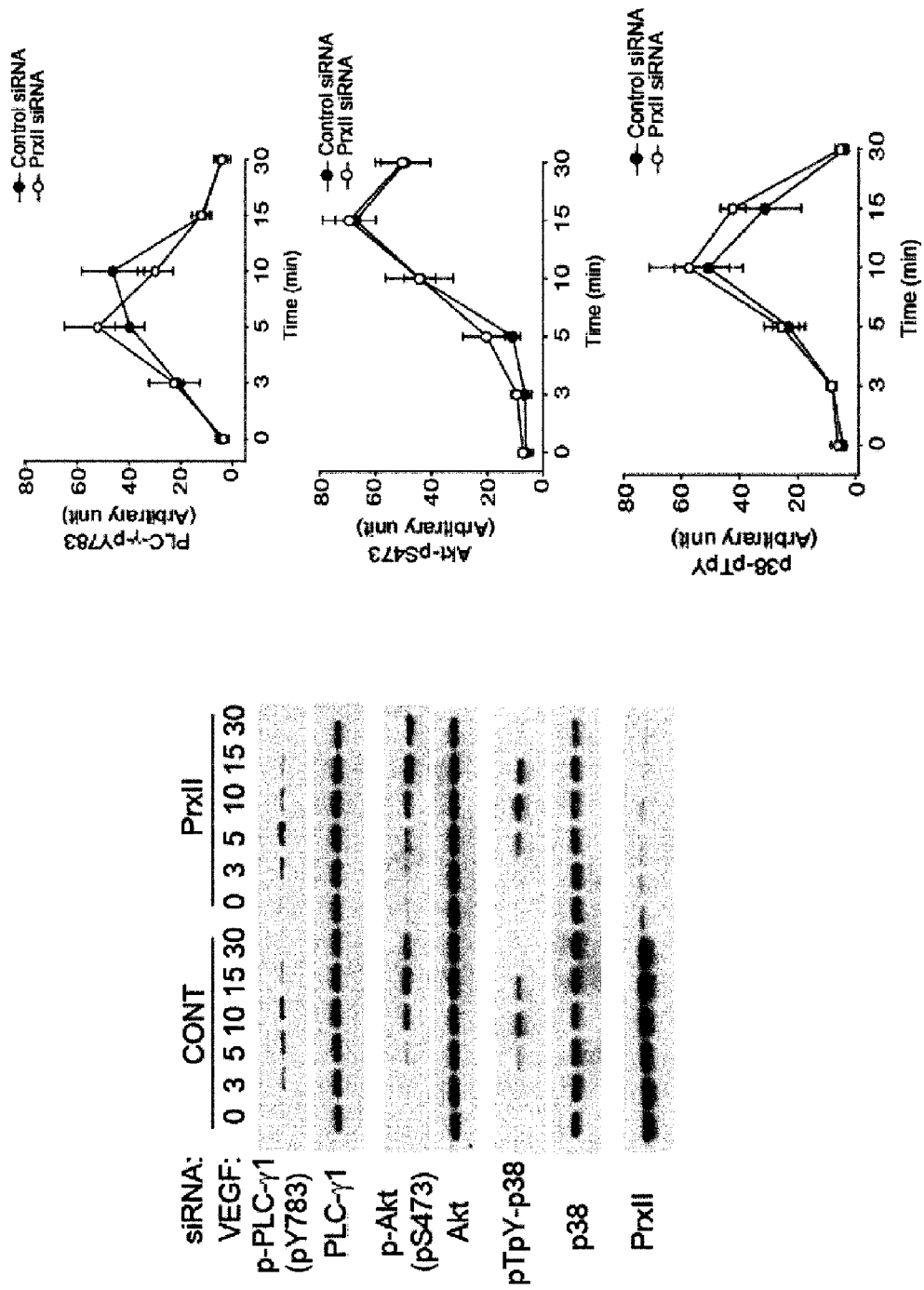

FIG. 13 shows the activation of downstream signaling molecules in VEGF-treated HAECs (related to FIG. 1c). Data in the graphs are means±S.D. of the relative intensities of the phospho-specific bands after being normalized by the intensities of the corresponding non-phospho bands (n=5). A representative blot is shown.

Figure 14:
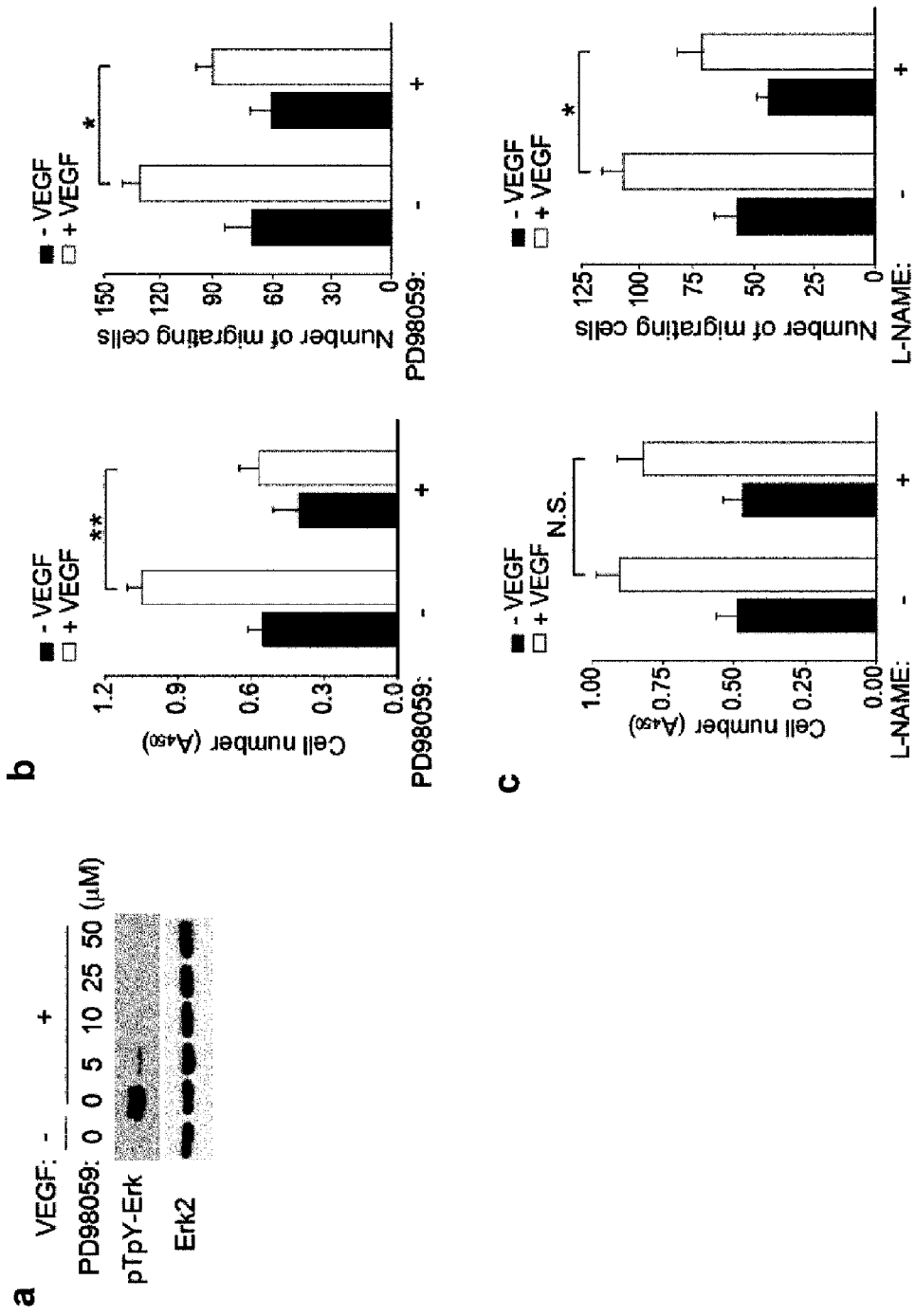

FIG. 14 shows the effect of ERK and eNOS inhibition on EC proliferation and migration in response to VEGF.

a. Titration of MEK1 inhibitor PD98059 for ERK inhibition in HAECs. The optimum concentration of PD98059 was determined by monitoring ERK phosphorylation.

b. and c. VEGF-induced proliferation and migration were measured in HAECs pretreated with either MEK1 inhibitor PD98059 (b, 10 μM) or eNOS inhibitor L-NAME (c, 3 mM) for 1 hour. Data show the means±S.D. (n=3, *P<0.01, **P<0.005; N.S., not significant).

Figure 15:
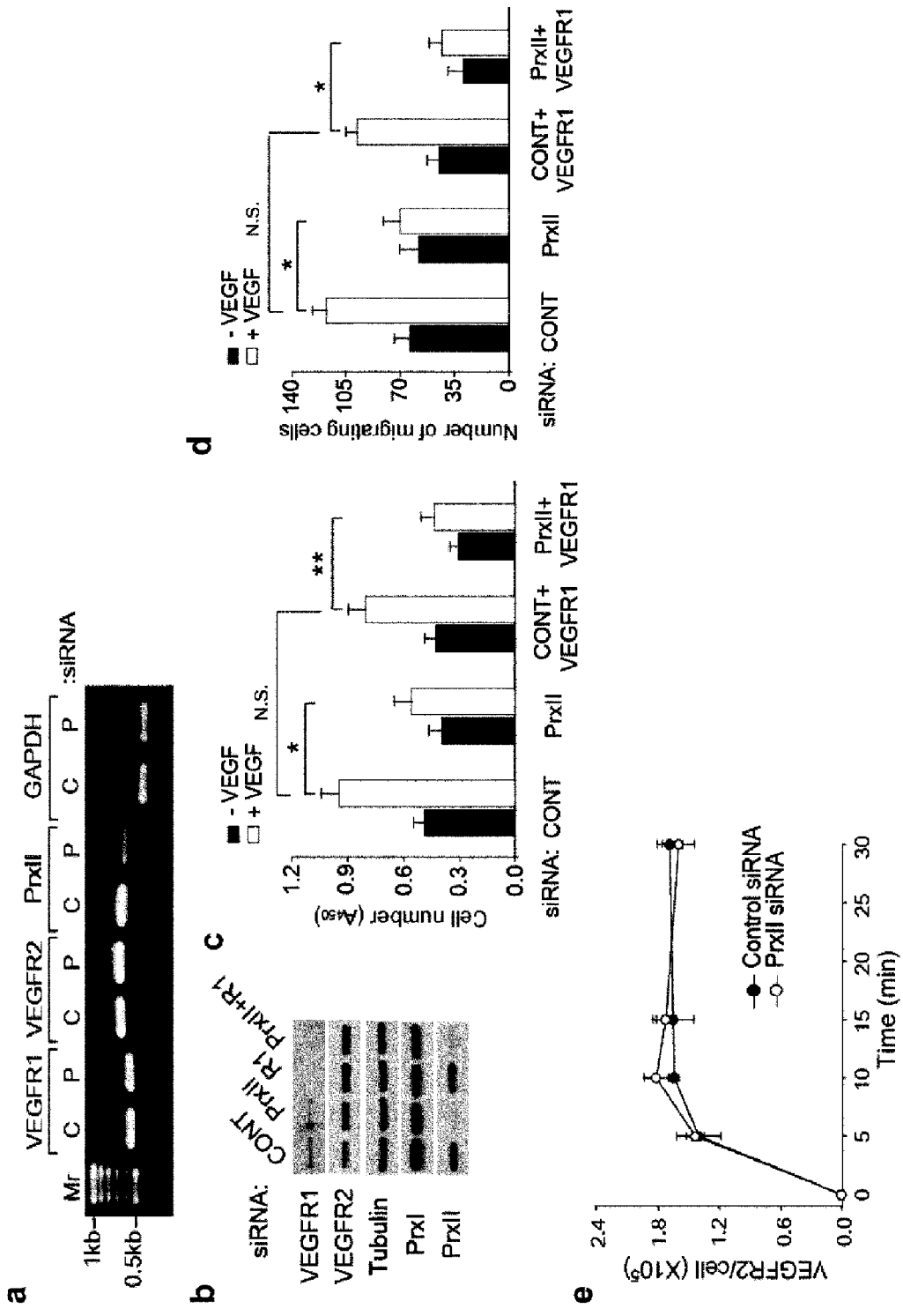

FIG. 15 shows examination of VEGFR1 and VEGF binding in HAECs with the Prx II knockdown.

a. Expression level of VEGFR transcripts in HAECs with the Prx II knockdown. RT-PCR was performed with total RNA mixture extracted from HAECs with control (C) and Prx II (P) knockdown.

b. Protein levels of VEGFRs in HAECs with the Prx II knockdown. HAECs were transfected with Prx II siRNA and/or VEGFR1 (R1) siRNAs for 24 hours and lysed for immunoblotting.

c. and d, VEGF-induced proliferation (c) and migration (d) were measured in HAECs with Prx II and/or VEGFR1 knockdown (n=3, *P<0.01, **P<0.005).

e. The HAECs (5,000 cells) were serum-starved for 18 hours and then incubated with 80 pM $^{125}$I-VEGF for the indicated periods of time. The cells were rinsed three times with phosphate-buffered saline and then the radioactivity levels were measured in γ-scintillation counter (Wallac, MicroBeta® TriLux 1450). The number of VEGFR-2 molecules per cell was calculated using the specific activity of $^{125}$I-VEGFR-2 (3907.2 cpm/fmol). The data shows the means±S.D.

Figure 16:
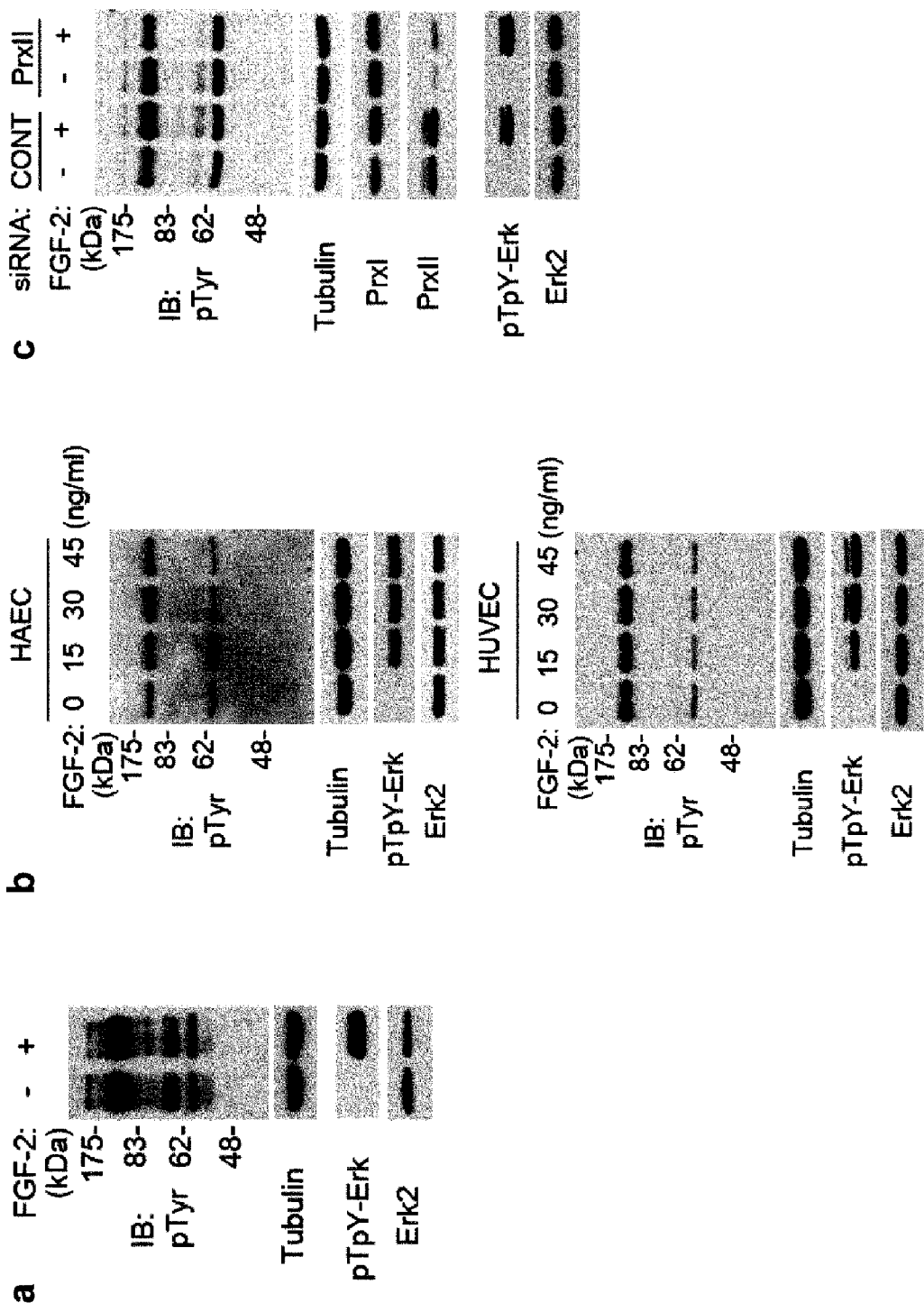

FIG. 16 shows the effect of Prx II knockdown on FGF-2 signaling.

a. FGF-2-induced protein tyrosine phosphorylation and ERK activation in IMR-90 human lung fibroblasts. IMR-90 cells were serum-starved for 24 hours and stimulated with IMR-90 for 10 minutes.

b. Dose dependency of FGF-2 on protein tyrosine phosphorylation and ERK activation in HAECs and HUVECs. Cells were stimulated with indicated doses of FGF-2 for 10 minutes.

c. FGF-2-induced tyrosine phosphorylation in HAECs transfected with either control or Prx II siRNA. A representative set of three independent experiments is shown.

Figure 17:
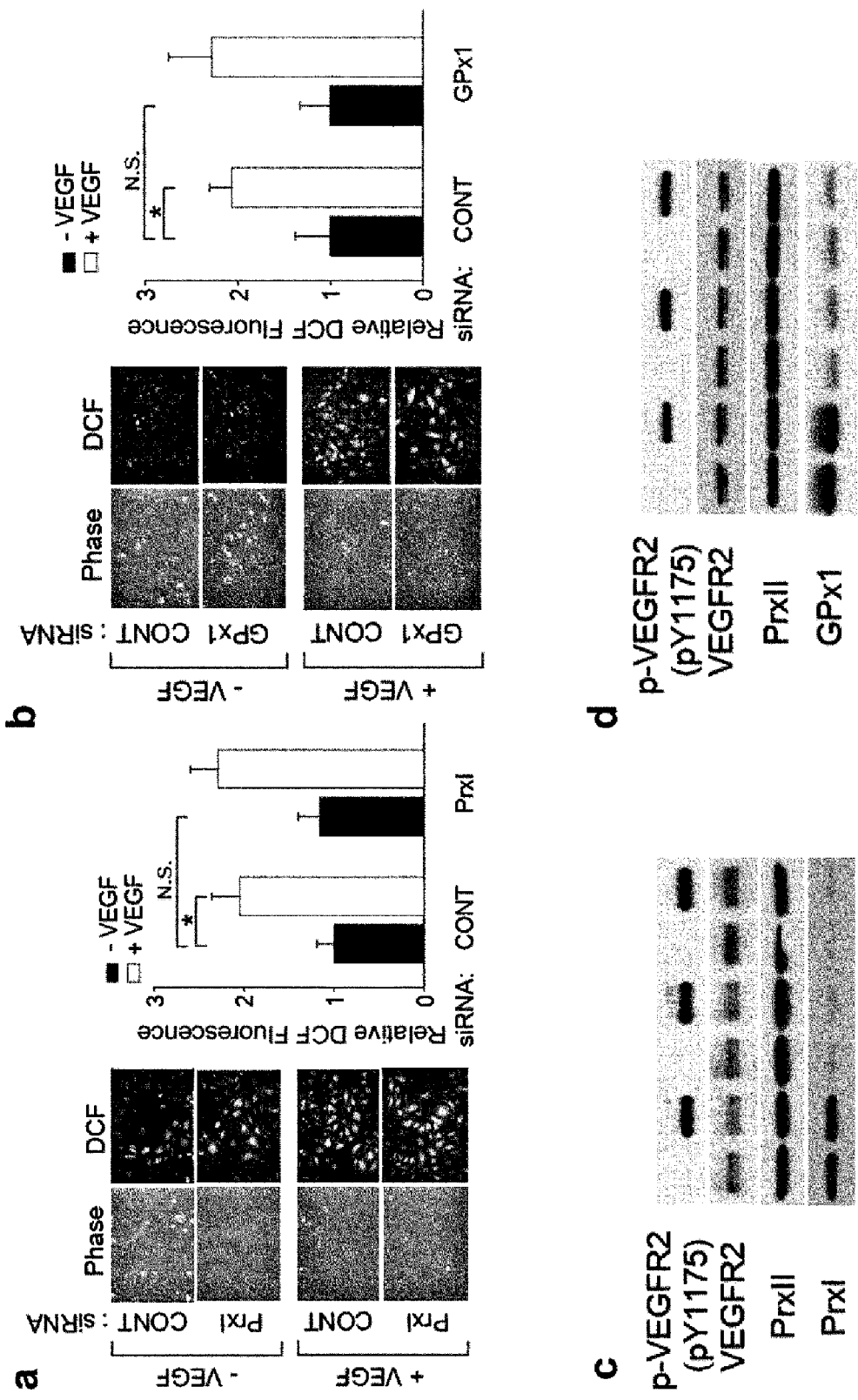

FIG. 17 shows the effect of PrxI and GPXl knockdown on VEGF-induced $H_2O_2$ production VEGFR-2 activation.

Knockdown of Prx I (a and c) and GPxl (b and d) affected neither $H_2O_2$ production nor VEGFR-2 activation induced by VEGF in HAECs. Data in the graph show means±S.D. (n=3, *P<0.005, N.S. not significant). Representative blots from three independent experiments are shown.

Figure 18:
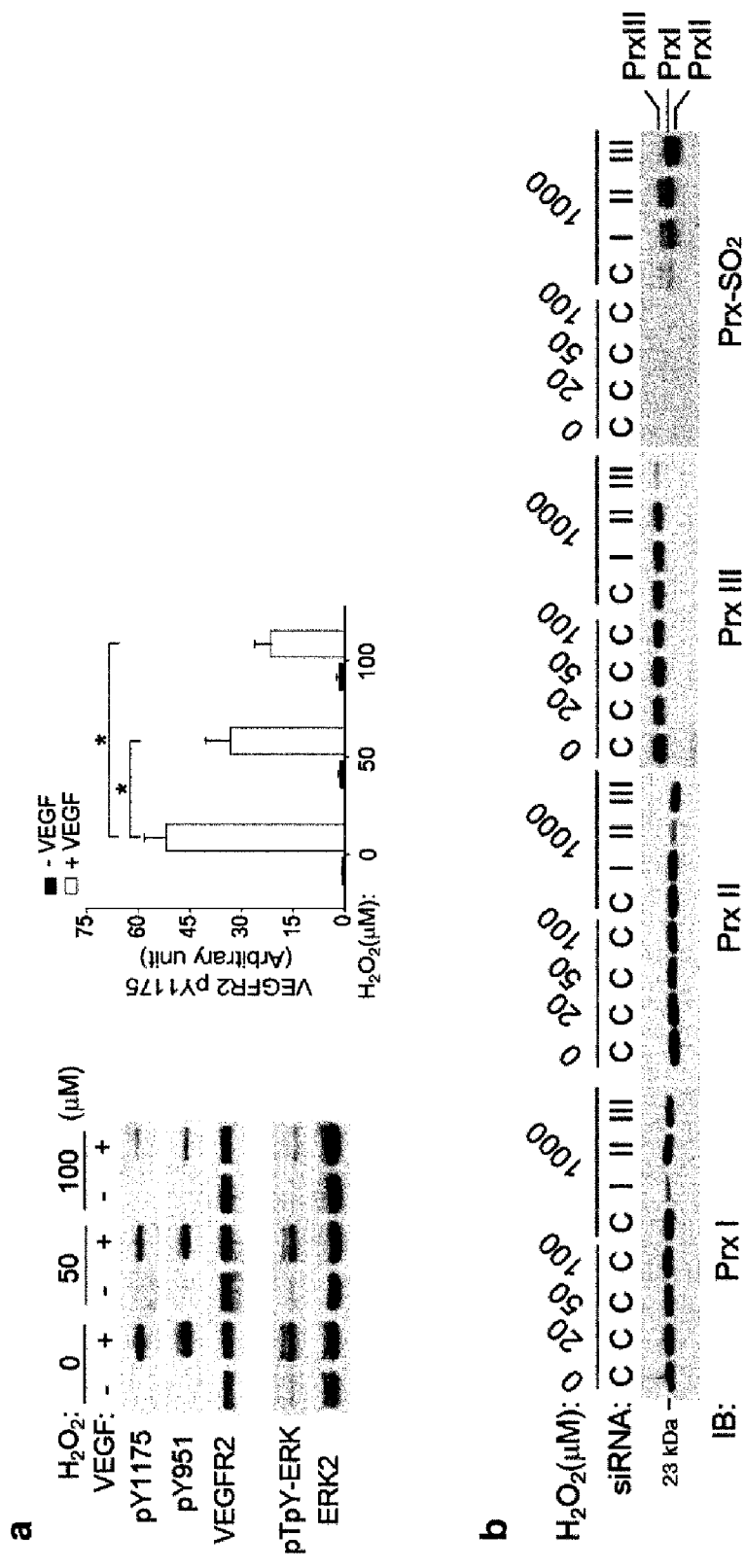

FIG. 18 shows the effect of exogenous $H_2O_2$ on VEGFR-2 activation and 2-cys Prx hyper-oxidation.
 a. $H_2O_2$ reduces VEGFR-2 activation in response to VEGF. HAECs were pretreated with the indicated concentrations of $H_2O_2$ for 10 minutes and then stimulated with VEGF for 5 minutes. Data in the graph are the means±S.D. of the relative intensities of the phospho-VEGFR-2 bands after being normalized by the intensities of the corresponding VEGFR-2 bands (n=3, *P<0.001). The ERK activation was reduced in parallel with the decreased VEGFR-2 phosphorylation.
 b. Micromolar range of $H_2O_2$ did not induce the hyperoxidation of 2-cys Prxs. HAECs were treated with the indicated concentrations of $H_2O_2$ for 10 minutes and subjected to immune-blotting using an antibody specific to the hyperoxidized 2-cys Prx (Prx-$SO_2$). Only 1 mM $H_2O_2$ slightly induced the hyperoxidation of Prx I and Prx III, as identified by transfection of the specific siRNAs (C, control siRNA; I, Prx I siRNA; II, Prx II siRNA; III, Prx III siRNA). Note that the knockdown of one Prx isoform accelerated the hyperoxidation of the other isoforms (see Prx-$SO_2$ blot). A representative set of three experiments is shown.

Figure 19:
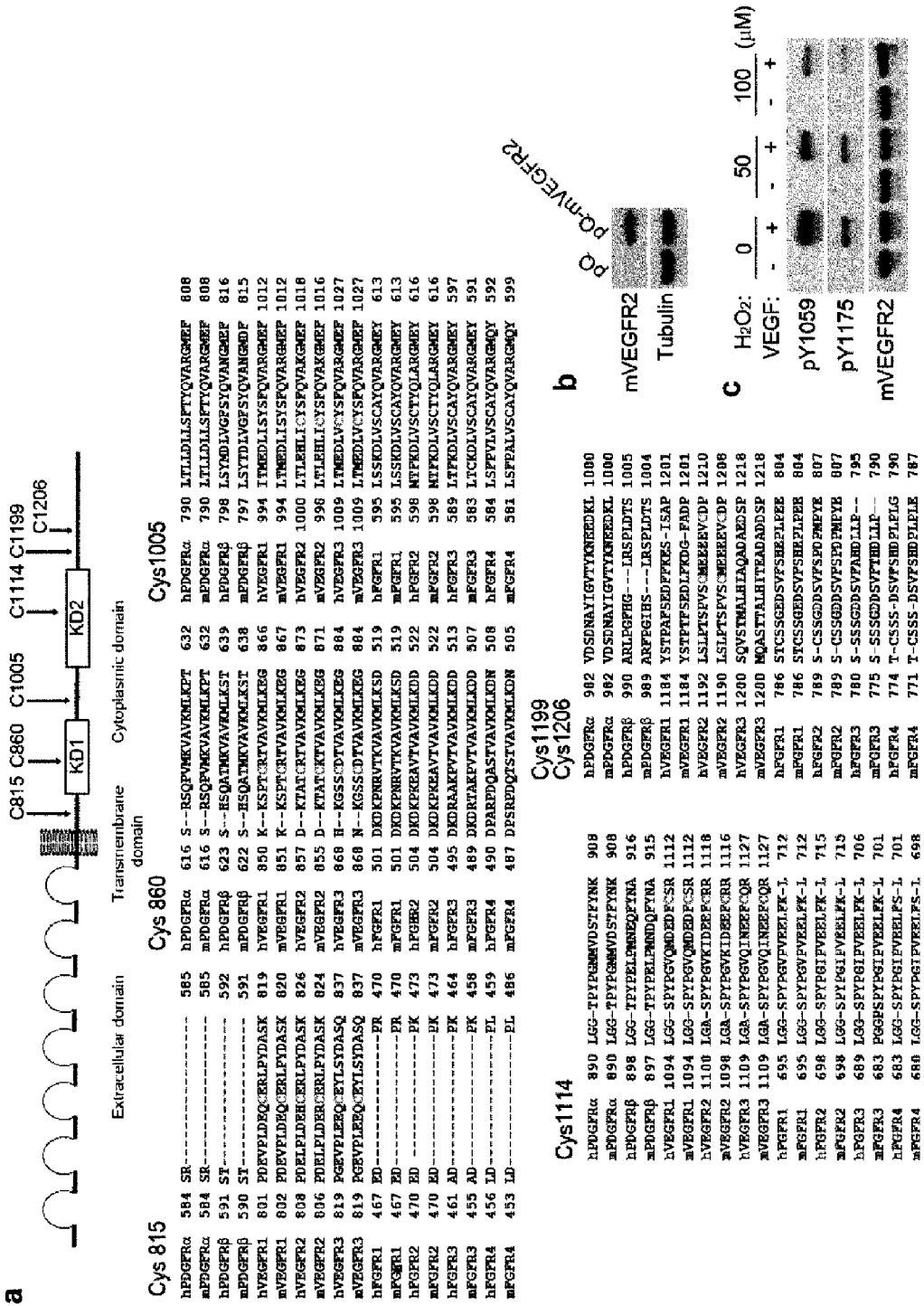
Figure 20:
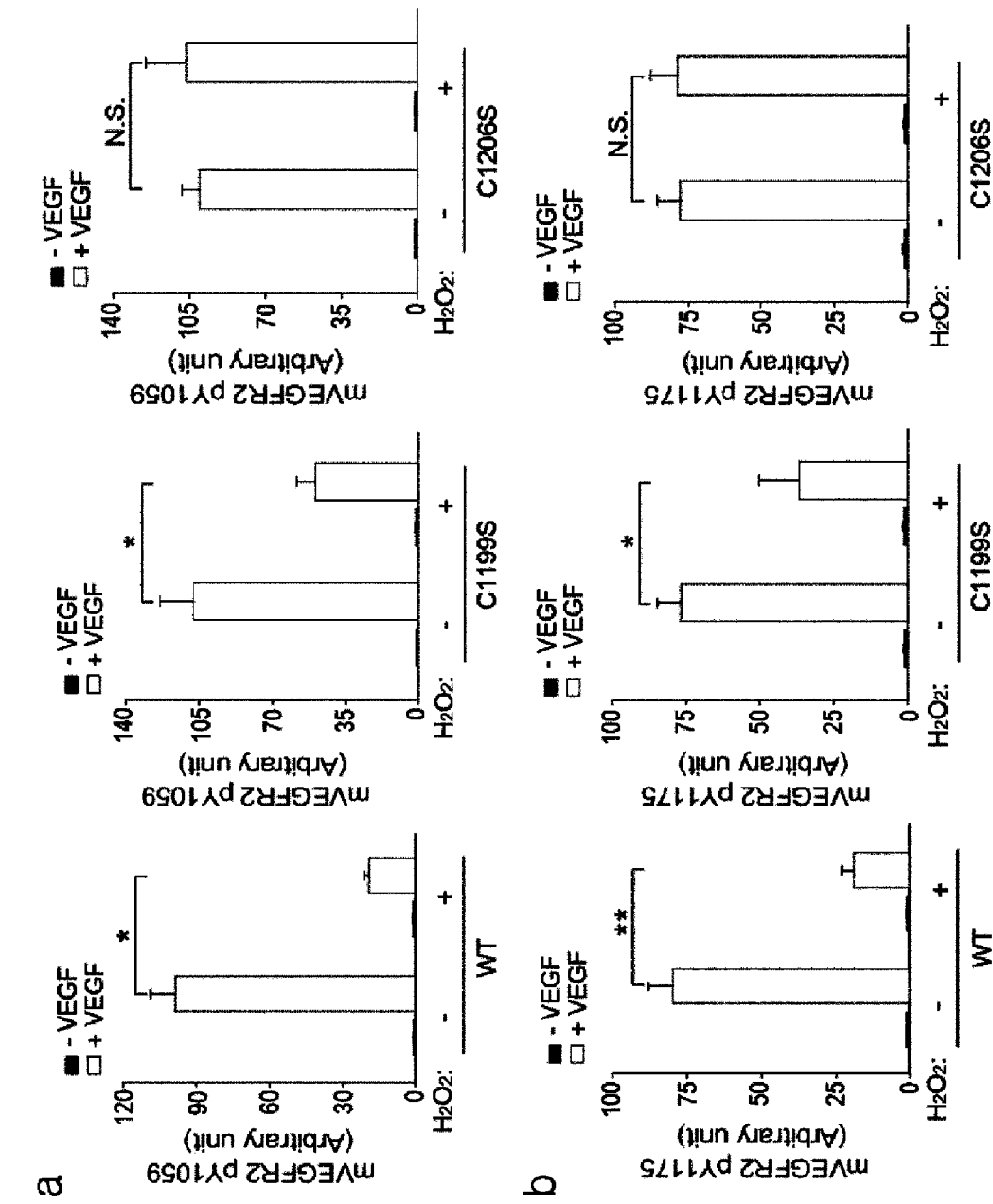

FIGS. 19-20 show that mouse VEGFR-2 activation is oxidation-sensitive.

FIG. 19 shows,
 a. Peptide sequence alignment of RTKs. VEGFR-2 is comprised of an extracellular domain, transmembrane domain, juxtamembrane domain, two separate kinase domains (KD1 and KD2), and C-terminal domain (top). The six cysteine residues conserved in VEGFRs are indicated by arrows. Primary sequences of human (h) and mouse (m) PDGFR, VEGFR, and FGF isoforms around the cysteine residues are aligned (bottom).
 b. Expression of mouse VEGFR-2 (mVEGFR2) in 293T cells.
 c. Effect of exogenous $H_2O_2$ on the VEGF-induced activation of mouse VEGFR-2 exogenously expressed in 293T cells.

FIG. 20 shows,
 a. and b. Quantification of mVEGFR-2 phosphorylation on Y1059 (a) and Y1175 (b). The blots obtained from three experiments were quantified. Data in the graphs are means±S.D. of the relative intensities of the phospho-VEGFR-2 bands after being normalized by the intensities of the corresponding VEGFR-2 bands (n=3, *P< 0.005, **P< 0.001, N.S. not significant).

Figure 21:
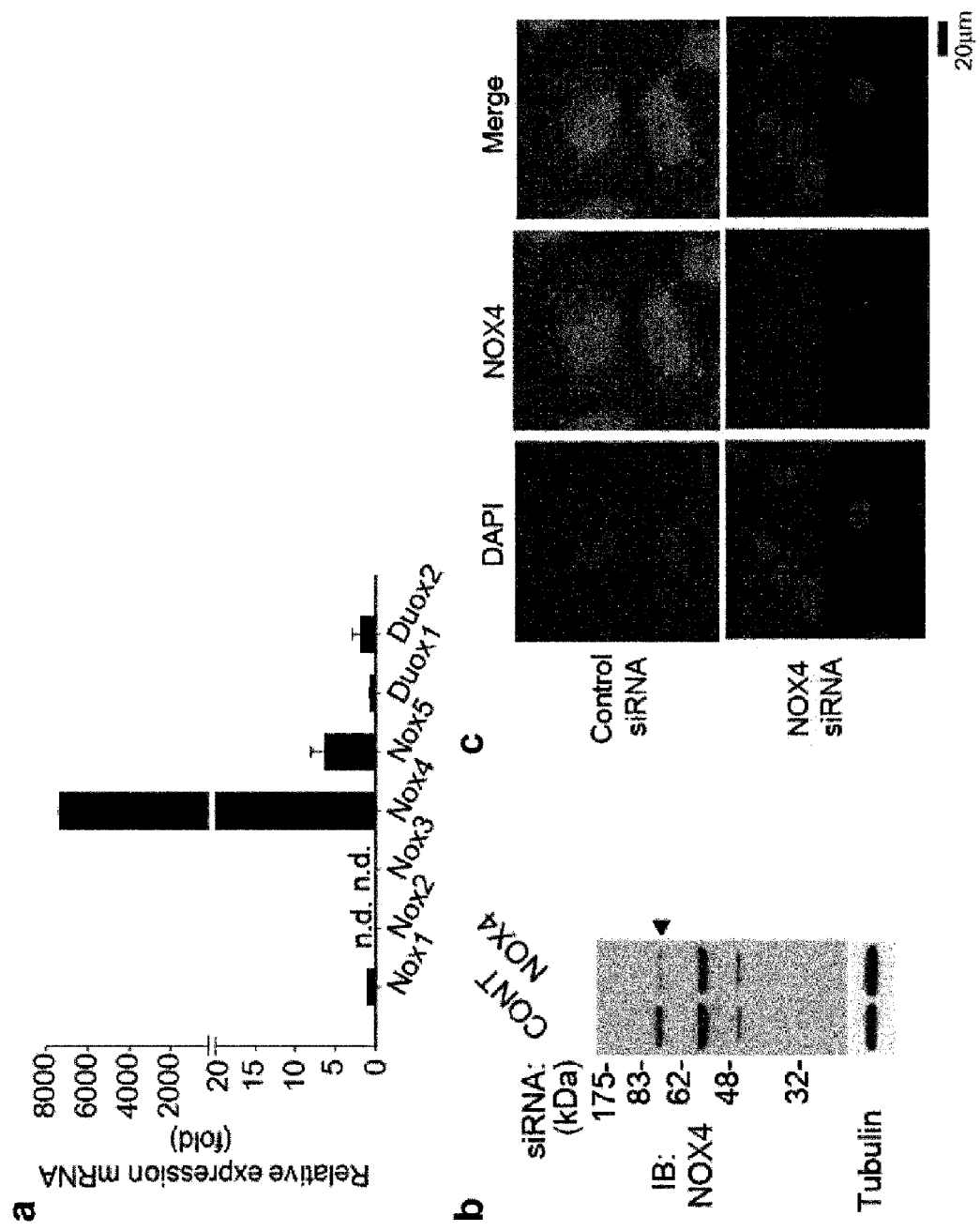

FIG. 21 shows expression of NOX isoforms in HAECs.
 a. The mRNA levels of the NOX isoforms in HAECs were measured by real-time qPCR. Data are represented as fold difference versus the NOX1 mRNA level (n=4, means±S.D.).
 b. Immunoblot detection of NOX4 in the extract of HAECs. The anti-NOX4 rabbit antisera were affinity-purified using antigenic peptide-conjugated agarose beads. The arrowhead indicates endogenous NOX4 proteins.
 c. Immunofluorescence staining of NOX4 proteins in HAECs. The HAECs with control or NOX4 knockdown were fixed with 3.7% paraformaldehyde in PBS and stained with anti-NOX4 antibody (1:300 dilution). Nuclei were labeled with DAPI.

Figure 22:
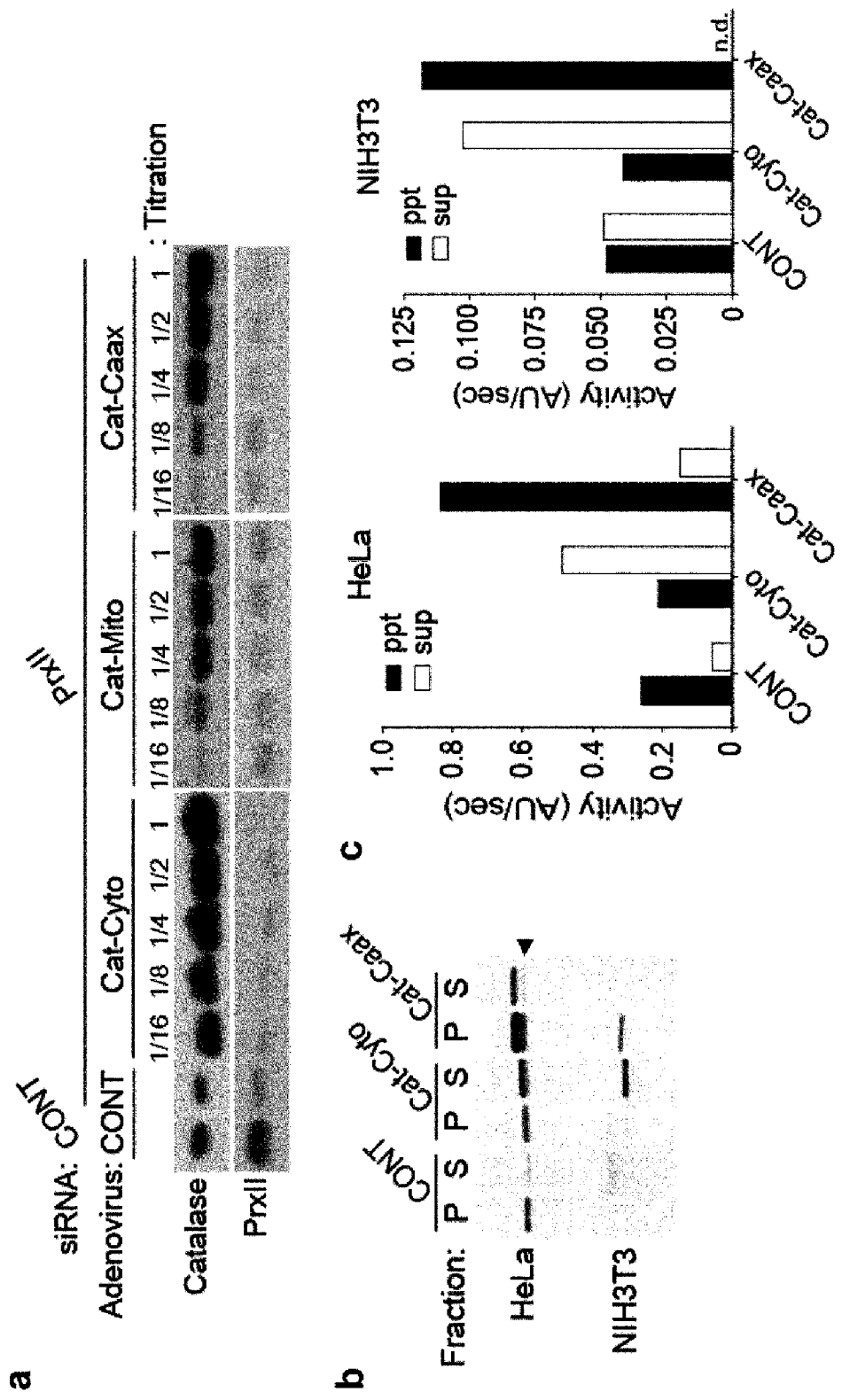
Figure 23:
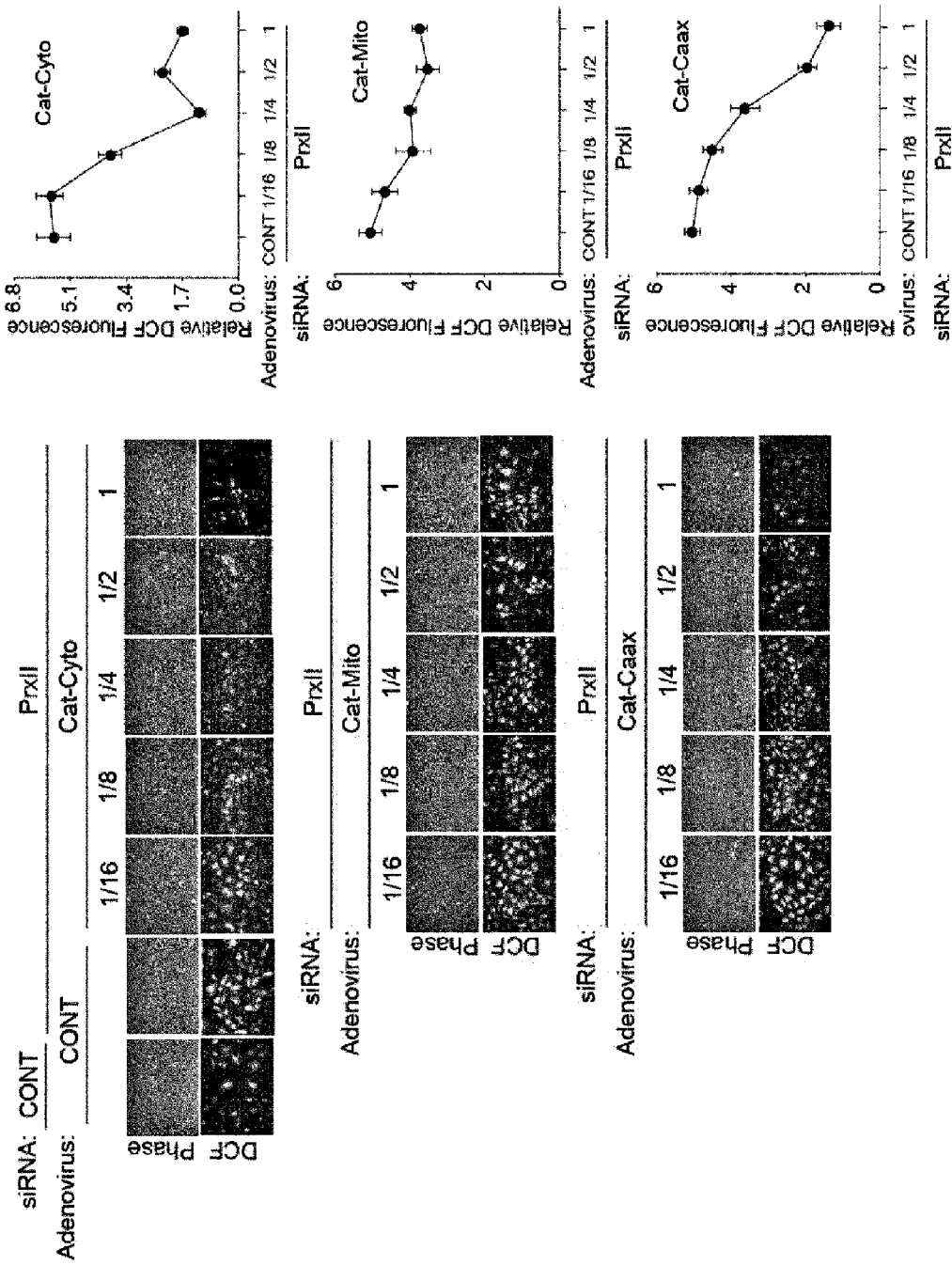

FIGS. 22-23 show targeted expression of human catalase in various cellular compartments.
 FIG. 22 shows,
 a. Adenoviral expression of human catalase targeted to different cellular compartments (Cat-Cyto for cytoplasm, Cat-Mito for mitochondria, Cat-Caax for lipid raft/caveolae in the plasma membrane) in HAECs. Cells were transfected with either control or Prx II siRNA, followed by infection with serial dilution of the indicated adenoviral solutions. The immunoblot analysis of catalase and Prx II expression was performed.
 b. Subcellular fractionation of HeLa and NIH3T3 cells infected with the indicated adenovirus for 24 hrs. The infected cells were lysed in a hypotonic buffer using Dounce homogenizer. After removing unbroken cells by centrifugation at 500×g, the clarified lysates were subjected to ultracentrifugation at 100,000×g. The supernatant (S) and pellet. (P) were collected for cytosol and membrane fractions, respectively. Endogenous catalase in HeLa cells is indicated (arrowhead).
 c. Activity assay of catalase in cytosolic supernatant (sup) and membrane pellet (ppt). Catalase activity was measured spectrophotometrically at 240 nm. in a potassium phosphate buffer (pH 7.0) containing 30 mM $H_2O_2$. n.d., not detected. Blots are representative of three experiments.

FIG. 23 shows elimination by targeted expression of catalase of basal $H_2O_2$ level increased in Prx II siRNA-transfected HAECs. Cells were transfected with Prx II siRNA and infected 24 hours later with a serial dilution of the indicated adenoviruses. Data in the graphs show the means±S.D. of the relative fluorescence level from three experiments.

Figure 24:
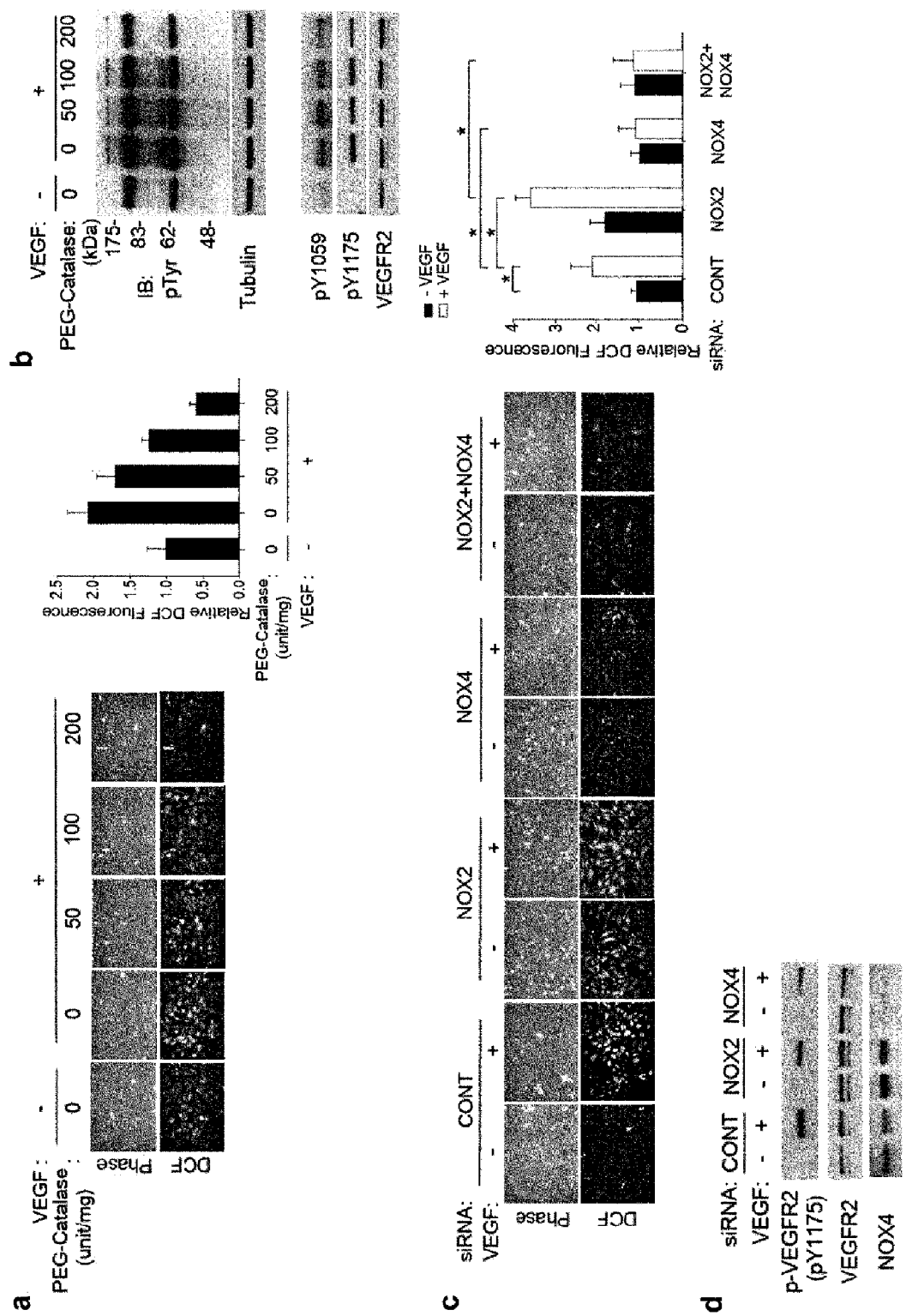

FIG. 24 shows involvement of VEGF-induced $H_2O_2$ production in VEGFR2-mediated signaling, supporting the known fact that $H_2O_2$ production is required for VEGF-mediated signaling.
 a. Elimination of VEGF-dependent intracellular $H_2O_2$ by introduction of catalase. HAECs were pretreated with polyethylene glycol (PEG)-catalase at indicated doses for 18 hours. Bars in the graph are the means±S.D. of the relative DCF fluorescence from 50-80 cells (n=3, *P<0.01).
 b. Reduction of VEGF-dependent tyrosine phosphorylation in HAECs by catalase. The tyrosine phosphorylation signal, albeit weak, was gradually decreased by increasing catalase doses.
 c. Effect of NOX knockdown on VEGF-dependent $H_2O_2$ production. HAECs were transfected with either control or indicated NOX siRNAs. Bars in the graph are the means±S.D. of the relative DCF fluorescence from 50-80 cells (*P<0.01).
 d. Effect of NOX knockdown on VEGFR-2 activation in the HAECs. A representative of three experiments is shown. Note that the endogenous NOX4 level was increased by the NOX2 knockdown.

Figure 25:
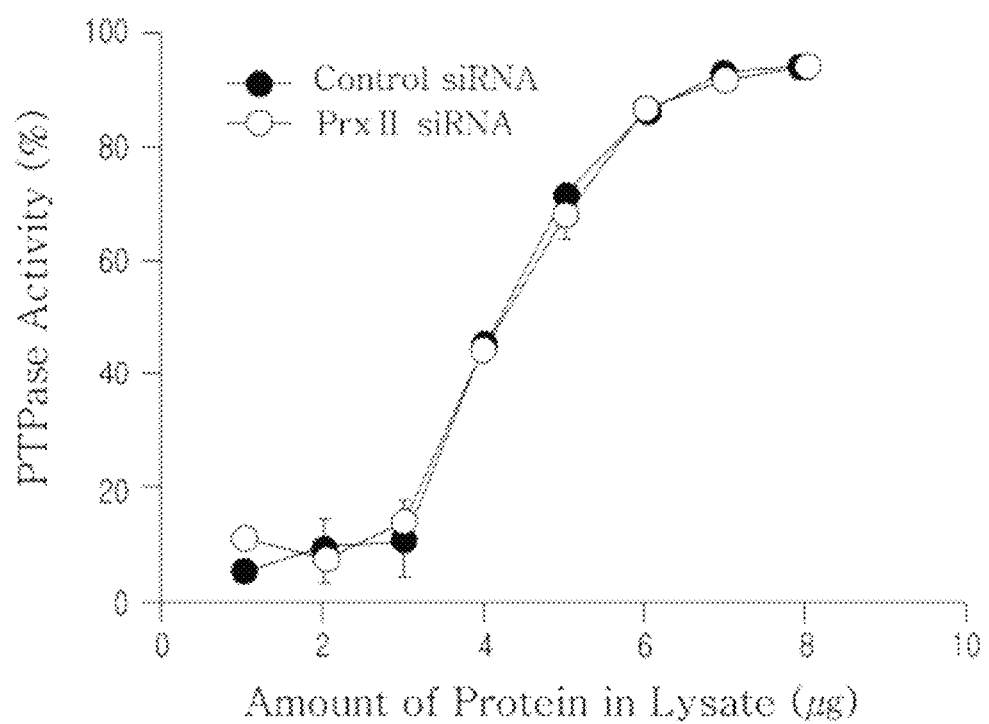

FIG. 25 shows the effect of Prx II knockdown on PTPase (Protein Tyrosine Phosphatase) activity. PTPase activity (Universal tyrosine phosphatase assay kit, Takara Bio., MK-411) was measured, in a 96-well plate coated with poly- (Glu4-pTyr) peptide according to the manufacturer's protocol. PTPase activity was calculated using the following equation:

$$y = 1.390x^{-0.783}$$

(x=PTP activity, y=OD450). Data show the means±S.D. of PTPase activity (n=3).

DETAILED DESCRIPTION OF THE PREFERRED EMBODIMENTS

In order to achieve the above objects, the present invention provides a pharmaceutical composition for inhibiting angiogenesis, comprising an inhibitor of Prx II gene expression or Prx II protein activity as an active ingredient.

Further, the inhibitor of the present invention is identified by a screening method.

The screening method of the present invention may include the steps of (a) analyzing Prx II protein activity or Prx II gene expression after treatment of a test material; and (b) determining the test material as an angiogenesis inhibitor when the Prx II protein activity or the Prx II gene expression after the treatment of the test material is inhibited, compared to the non-treatment of the test material. The Prx II protein activity or the Prx II gene expression can be analyzed in vivo or in vitro.

The screening method of the present invention may include the steps of (a) reacting a test material with a buffer solution containing Prx II protein, thioredoxin (Trx), thioredoxin reductase (TrxR) and NADPH; (b) reacting the reaction product of step (a) with $H_2O_2$ to prepare a first experimental group; (c) reacting a buffer solution containing Prx II protein, thioredoxin (Trx), thioredoxin reductase (TrxR) and NADPH with $H_2O_2$ to prepare a first control group; (d) measuring and comparing the absorbance of the first experimental group and the first control group; and (e) determining the test material as an inhibitor when the absorbance of the first experimental group is lower than that of the first control group.

The screening method of the present invention may also include the steps of (a) reacting a test material with a buffer solution containing Prx II protein, thioredoxin (Trx), thioredoxin reductase (TrxR) and NADPH; (b) reacting the reaction product of step (a) with $H_2O_2$ to prepare a first experimental group; (c) reacting a buffer solution containing Prx II protein, thioredoxin (Trx), thioredoxin reductase (TrxR) and NADPH with $H_2O_2$ to prepare a first control group; (d) measuring and comparing the absorbance of the first experimental group; and the first control group; (e) reacting the test material with a buffer solution containing one or more protein selected, from the group consisting Prx I, III, IV and V, thioredoxin (Trx), thioredoxin reductase (TrxR) and NADPH; (f) reacting the reaction product of step (e) with $H_2O_2$ to prepare a second experimental group; (g) reacting a buffer solution containing one or more protein selected from the group consisting Prx I, III, IV and V, thioredoxin (Trx), thioredoxin reductase (TrxR) and NADPH with $H_2O_2$ to prepare a second control group; (h) measuring and comparing the absorbance of the second experimental group and the second control group; and (i) determining the test material as an inhibitor when there is no difference in absorbance between the second control group; and the second experimental group, while the absorbance of the first experimental group is lower than that of the first control group.

Further, the present invention provides a kit for screening angiogenesis inhibitors comprising a Prx II protein and a reaction buffer solution. The kit of the present invention may further comprise thioredoxin, thioredoxin reductase, NADPH and $H_2O_2$.

Further, the present invention provides a method for inhibiting angiogenesis, comprising the step of administering to a subject in need thereof an inhibitor of Prx II gene expression or Prx II protein activity.

The present invention inhibits expression or activity of intracellular peroxiredoxin II (Prx II) to reduce VEGFR (vascular endothelial growth factor receptor) activation in response to VEGF and VEGF signal transduction, thereby inhibiting angiogenesis. Therefore, various angiogenesis-related diseases, ailments, or conditions can be prevented or treated by the present invention.

Peroxiredoxin (Prx) is a scavenger of hydrogen peroxide and alkyl hydroperoxides in living organisms (Chae, H. Z. et al., Proc. Nat. Acad. Sci., 1994 91: 7017-7021). Six different Prx isoforms (Prx I-Prx VI) are present in various tissues of mammals, and they are known to have antioxidant activity in vivo. In addition, Prxs have been implicated in a number of cellular functions such as cell proliferation and differentiation, enhancement of NK (natural killer) activity, protection of radical-sensitive proteins, heme metabolism and intracellular signaling. Prx II is known to be an intracellular peroxidase that removes endogenous $H_2O_2$ produced in response to growth factors including platelet-derived growth factor (PDGF) and epidermal growth factor (EGF), and it is located in abundance in the cytoplasm of cells, and binds to integral membrane proteins or cell membranes.

According to the present invention, Prx II positively regulates VEGF (vascular endothelial growth factor) signaling in VECs (vascular endothelial cells)

According to a preferred embodiment of the present invention, the Prx II of the present invention has an activity of removing reactive oxygen species (ROS) in the cells, preferably vascular endothelial cells (VECs). Prx II eliminates basal reactive oxygen species (especially, $H_2O_2$) in the cells regardless of VEGF stimulation, thereby inhibiting oxidative inactivation of VEGFR (vascular endothelial growth factor receptor). Thus, VEGF signaling can be regulated by Prx II regulation.

According to a preferred embodiment of the present invention, inhibition of Prx II gene expression or Prx II protein activity reduces VEGF (vascular endothelial growth factor) signaling.

More specifically, inhibition of Prx II gene expression or Prx II protein activity reduces VEGF (vascular endothelial growth factor) signaling by inducing a reduction in activated VEGFR, preferably VEGFR-2 phosphorylation. According to a preferred embodiment of the present invention, phosphorylation of tyrosine residues in VEGFR-2 at positions 951, 1059, 1175, and 1214 is reduced by inhibition of Prx II gene expression or Prx II protein activity, leading to a reduction in VEGFR-2 activity. Thus, a reduction in VEGF activity is caused by inhibition of Prx II gene expression or Prx II protein activity, and consequently, VEGF signaling can be reduced. Importantly, any other isoforms of 2-cys Prxs, Prx I, and Prx III to Prx IV did not show such effect on tyrosine phosphorylation of VEGFR as Prx II. In addition, specific regulatory effect of Prx II on VEGF signaling was also observed in vascular endothelial cells, for example, human umbilical vein endothelial cells and human lung microvascular endothelial cells, which generalizes the regulatory effect of Prx II on VEGF signaling among EC types.

According to a preferred embodiment of the present invention, down-regulation of VEGF signaling by inhibition of Prx II gene expression or Prx II protein activity is mediated by VEGF-A, VEGF-C or VEGF-E, and more preferably VEGF-A.

According to the present invention, the inhibition of Prx II gene expression or Prx II protein activity induces inhibition or reduction of intracellular VEGF signaling, thereby reducing the expression or activity of downstream signaling molecules of the signaling pathway. The inhibition or reduction of VEGF signaling reduces cell proliferation and chemotactic migration, consequently leading to inhibition of angiogenesis.

According to a preferred embodiment of the present invention, the inhibition or reduction of VEGF signaling by inhibition of Prx II gene expression or Prx II protein activity of the present invention inhibits activation of endothelial nitric oxide synthase (eNOS) or ERK (extracellular signal-regulated kinase, MAPK), or reduces VEGF-induced cGMP production.

According to a more preferred embodiment of the present invention, the inhibition of Prx II gene expression or Prx II protein activity of the present invention increases oxidative inactivation of VEGF receptor tyrosine kinase (RTK). More preferably, the above described RTK is VEGFR-2 RTK. VEGFR-1 was not involved in down-regulation of VEGF signaling in ECs by Prx II depletion.

Specifically, the Prx II knockdown resulted in an increase of basal ROS level of vascular endothelial cells, regardless of VEGF stimulation. In contrast, neither Prx I nor GPxl affected basal ROS level. Furthermore, when catalase, an enzyme that reduces $H_2O_2$ to $H_2O_2$, is artificially introduced to examine the actual substrate of Prx II, the level of ROS increased by the Prx II knockdown was returned to the background level, which confirms that $H_2O_2$ was the actual substrate of Prx II. The increased basal $H_2O_2$ level inhibits VEGFR-2 RTK activity. The Prx II knockdown did not alter the protein level and VEGF-VEGFR-2 binding affinity in ECs. In addition, knockdown of Prx II expression aid not affect endogenous PTPase activity.

Meanwhile, upon add-back expression of Prx II, the wild-type Prx II restored VEGFR-2 activation, whereas an inactive cysteine mutant of Prx II did not. This result indicates that the peroxidase activity of Prx II is essential for protecting VEGFR-2 against oxidation.

In the present invention, the oxidative inactivation of VEGFR-2 is induced by ROS-mediated reactive cysteine residues. More specifically, in order to test whether cysteine residues are involved in the redox regulation of VEGFR-2, cysteine residues were labeled with fluorophore-conjugated maleimides. In one specific Example of the present invention, oxidation of cysteine residues of VEGFR-2 remarkably increased by the Prx II knockdown in VECs. In particular, Cys1206 residue is the direct oxidation site for redox regulation of VEGFR-2 RTK activity, and disulfide linkage is formed between Cys1206-sulfenic acid and Cys1199 residue in oxidized VEGFR-2 to stabilize Cys1206-sulfenic acid. Cys1199 residue is essential for reversibility of the oxidation of VEGFR-2 C1206 residue.

In the present invention, it was confirmed that Prx II and VEGFR-2 protein are colocalized in the lipid raft/caveolae, and NOX4 is a major producer of basal $H_2O_2$ in ECs. In the specific Example of the present invention, the double knockdown of Prx II with NOX4 completely rescued VEGFR-2 activation in response to VEGF. When caveolin-1 was knocked down in ECs, VEGFR-2 activation was no longer affected by the Prx II knockdown. In addition, in order to examine that Prx II protects VEGFR-2 from the oxidation by NOX4-derived $H_2O_2$ in ECs regardless of VEGF stimulation due to localized action of $H_2O_2$ in lipid raft/caveolae microdomain, peroxisomal hydrogen peroxide ($H_2O_2$)-scavenging enzyme catalase was artificially modified and introduced into various cells. As a result, the membrane-targeted catalase only rescued the VEGFR-2 activation lost by the Prx II knockdown in ECs. Collectively, these data conclude that the redox sensitivity of VEGFR-2 via unique Cys1206 residue is due to $H_2O_2$ derived from NOX4 present within caveolae, and therefore, protection by Prx II is crucial for VEGFR-2 activation in response to VEGF.

As described above, the inhibitor of Prx II gene expression or Prx II protein activity of the present invention inhibits VEGFR-2 activation, that is, phosphorylation, leading to inhibition of angiogenesis. The inhibition of VEGFR-2 activation inhibits VEGFR-2 downstream signaling, thereby exerting various pharmacological actions. More specifically, the inhibitor of Prx II gene expression or Prx II protein activity of the present invention selectively inhibits VEGF-induced activation of eNOS and ERK, and inhibits the proliferation, migration, and further tube formation of endothelial cells in response to VEGF, consequently leading to inhibition of angiogenesis. The inhibitory effect of Prx II deficiency on VEGF-dependent microvessel outgrowth was demonstrated by ex vivo and in vivo experiments. Specifically, in cutaneously wounded mice, the vessel density in the wounded edge was much less in Prx II−/− mice than the WT mice. In tumor xenograft models, the tumor growth in Prx II−/− mice was slower than that in WT mice.

The diseases, ailments, and conditions to be prevented or treated by the composition of the present invention include various angiogenesis-related diseases. Preferably, the diseases to be prevented or treated by the composition of the present invention include cancer, diabetic retinopathy, retinopathy of prematurity, corneal transplant rejection, neovascular glaucoma, erythrosis, proliferative retinopathy, cancer, psoriasis, hemophilic arthropathy, capillary proliferation in atherosclerotic plaques, keloid, wound granulation, rheumatoid arthritis, ostarthritis, autoimmune diseases, Crohn's disease, atherosclerosis, cat scratch disease, ulcer, cirrhosis, glomerulonephritis, diabetic nephropathy, malignant nephrosclerosis, thrombotic microangiopathy, organ-transplant rejection, glomerulopathy, diabetes, inflammatory diseases, and neurodegenerative diseases.

The autoimmune diseases to be prevented or treated by the composition of the present invention include alopecia areata, ankylosing spondylitis, antiphospholipid syndrome, autoimmune Addison's disease, autoimmune adrenal disease, autoimmune hemolytic anemia, autoimmune hepatitis, autoimmune ovaritis and testitis, autoimmune thrombocytopenia, Behcet's disease, Bullous pemphigoid, cardiomyopathy, celiac sprue-dermatitis, chronic fatigue immune dysfunction syndrome, chronic inflammatory demyelinating polyradiculoneuropathy, Churg-Strauss syndrome, cicatricial pemphigoid, CREST syndrome, cold agglutinin disease, Crohn's disease, discoid lupus, essential mixed cryoglobulinemia, fibromyalgia-fibromyositis, glomerulonephritis, Grave's disease, Guillain-Barre syndrome, Hashimoto's thyroiditis, idiopathic pulmonary fibrosis, idiopathic thrombocytopenic purpuras, IgA nephropathy, juvenile arthritis, lichen planus, lupus erythematosus, Meniere's disease, mixed connective tissue disease, multiple sclerosis, type I or immune-mediated diabetes, myasthenia gravis, pemphigus vulgaris, pernicious anemia, polyarteritis nodosa, polychondritis, autoimmune polyglandular syndrome, polymyalgia rheumatica, polymyositis and dermatomyositis, primary agammaglobulinemia, primary biliary cirrhosis, psoriasis, psoriatic arthritis, Raynaud's phenomenon, Reiter's syndrome, rheumatoid arthritis, Sarcoidosis, scleroderma, stiff-person syndrome, systemic lupus erythematosus, lupus erythematosus, Takayasu's arteritis, temporal arteritis, giant cell arteritis, ulcerative colitis, uveitis, vitiligo and Wegener's granulomatosis, but are not limited thereto.

The inflammatory diseases to be prevented or treated by the composition of the present invention include asthma, encephalitis, inflammatory enteritis, chronic obstructive pulmonary disease, allergy, septic shock, pulmonary fibrosis, undifferentiated spondyloarthropathy, undifferentiated spondylopathy, arthritis, inflammatory osteolysis, and chronic inflammation caused by chronic viral or bacterial infections, but are not limited thereto.

According to a preferred embodiment of the present invention, the cancers to be prevented or treated by the composition of the present invention includes brain cancer, neuroendocrine carcinoma, gastric cancer, lung cancer, breast cancer, ovarian cancer, liver cancer, bronchial cancer, nasopharyngeal cancer, laryngeal cancer, pancreatic cancer, bladder cancer, adrenal gland cancer, colorectal cancer, colon cancer, cervical cancer, prostate cancer, bone cancer, skin cancer, thyroid cancer, parathyroid cancer and ureter cancer, but are not limited thereto.

According to a preferred embodiment of the present invention, the composition of the present invention is a pharmaceutical composition comprising (a) a pharmaceutically effective amount of the above described inhibitor of Prx II gene expression or Prx II protein activity of the present invention; and (b) a pharmaceutically acceptable carrier.

As used herein, the term "pharmaceutically effective amount" means a sufficient amount that will elicit the efficacy or activity of the above described inhibitor of Prx II gene expression or Prx II protein activity.

When the composition of the present invention is formulated into a pharmaceutical composition, the pharmaceutical composition of the present invention includes pharmaceutically acceptable carriers. The pharmaceutically acceptable carriers that are included in the pharmaceutical composition of the present invention may be materials conventionally used in formulations, and include, but are not limited to, lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate and mineral oil. The pharmaceutical composition of the present invention may further include lubricants, wetting agents, sweeteners, flavoring agents, emulsifiers, suspending agents, preservatives and the like, in addition to the above-mentioned ingredients. The suitable pharmaceutically acceptable carriers and preparations are described in detail in Remington's Pharmaceutical Sciences (19$^{th}$ ed., 1995).

The present invention relates to a method for inhibiting angiogenesis, comprising the step of administering to a subject in need thereof an inhibitor of Prx II gene expression or Prx II protein activity, or the pharmaceutical composition of the present invention. The pharmaceutical composition may be conventionally administered by oral or parenteral routes known in the art. Examples of parenteral routes may include intravenous, subcutaneous, intramuscular, intraperitoneal, transdermal, intramucosal and intraocular injections.

The effective dose of the pharmaceutical composition of the present invention may vary depending on various factors such as formulation methods, administration manners, age, weight, sex, pathological conditions, and dietary habits of patients, treatment duration, administration routes, excretion rates and response sensitivity. Preferably, the pharmaceutical composition of the present invention may be administered at a dose of 0.001-100 mg/kg (body weight)/day for adults.

Furthermore, the present invention relates to a use of the inhibitor of Prx II gene expression or Prx II protein activity, or the pharmaceutical composition of the present invention in the preparation of angiogenesis-inhibiting medicines.

Angiogenesis-inhibiting medicines may be prepared by a method comprising: (a) reacting the test material with a buffer solution containing Prx II protein, thioredoxin (Trx), thioredoxin reductase (TrxR) and NADPH; (b) reacting the reaction product of step (a) with $H_2O_2$ to prepare an experimental group; (c) reacting a buffer solution containing Prx II protein, thioredoxin (Trx), thioredoxin reductase (TrxR) and NADPH with $H_2O_2$ to prepare a control group; (d) measuring and comparing the absorbance of the experimental group and the control group; (e) determining the test material as an inhibitor of Prx II protein activity when the absorbance of the experimental group is lower than that of the control group; and (f) preparing angiogenesis-inhibiting medicines using a pharmaceutically effective amount of the inhibitor and a pharmaceutically acceptable carrier.

The pharmaceutical composition of the present invention may be formulated into unit dosage forms, e.g., in multi-dose containers, using pharmaceutically acceptable carriers and/or excipients, according to a method that can be easily practiced by one of ordinary skill in the art to which the invention pertains. The formulations may take such forms as solutions, suspensions, syrups or emulsions in oily or aqueous media, or extracts, powders, granules, tablets, or capsules and may further include dispersing agents or stabilizing agents.

The inhibitor of Prx II gene expression or Prx II protein activity used as an active ingredient in the composition of the present, invention includes antisense oligonucleotides, siRNA oligonucleotides, antibodies, aptamers, single chain variable region fragments, peptides, low-molecular-weight compounds, and natural extracts, but is not limited thereto.

Preferably, the inhibitor of Prx II gene expression is antisense oligonucleotides or siRNA oligonucleotides specifically binding to Prx II gene.

As used herein, the term "antisense oligonucleotide" means DNA or RNA or derivatives thereof containing a nucleic acid sequence complementary to a particular mRNA sequence, and binds to the complementary sequence within mRNA to inhibit translation of mRNA into protein. The antisense oligonucleotide sequence may be a DNA or RNA sequence that is complementary to Prx II mRNA, and is able to bind to Prx II mRNA, and it is able to inhibit translation, cytoplasmic translocation, or maturation of Prx II mRNA or all other activities essential for overall biological functions. The antisense oligonucleotide has a length of 6 to 100 bases, preferably 8 to 60 bases, and more preferably 10 to 40 bases.

The antisense oligonucleotide may be modified at one or more positions of the bases, sugars or backbones in order to have improved effectiveness (De Mesmaeker et al., Curr Opin Struct Biol., 5 (3): 343-55(1995)). The oligonucleotide backbone may be modified, for example, with phosphorothioates, phosphotriesters, methyl phosphonates, short chain alkyl, cycloalkyl, or short chain heteroatomic or heterocyclic inter-sugar linkages. Also, the antisense oligonucleotide may contain one or more substituted sugar moieties. The antisense oligonucleotide may also contain modified bases. Examples of the modified bases include hypoxanthine, 6-methyladenine, 5-methylpyrimidines (especially, 5-methylcytosine), 5-hydroxymethylcytosine (HMC), glycosyl HMC, gentiobiosyl HMC, 2-aminoadenine, 2-thiouracil, 2-thiothymine, 5-bromouracil, 5-hyroxymethyluracil, 8-azaguanine, 7-deazaguanine, N6 (6-aminohexyl) adenine, and 2,6-diaminopurine. In addition, the antisense oligonucleotide of the present invention may be chemically bonded to one or more moieties or conjugates enhancing the activity and cellular uptake of the antisense oligonucleotide. For example, liphophilic moieties include, but are not limited to, a cholesterol moiety, a cholesteryl moiety, cholic acid, a thioether, a thiocholesterol, an aliphatic chain, a phospholipid, a polyamine chain, a polyethylene glycol chain, adamantane acetic acid, a palmityl moiety, an octadecylamine moiety and a hexylamino-carbonyl-oxycholesterol moiety. A method of preparing oligonucleotides including lipid moieties is well known in the art (U.S. Pat. Nos. 5,138,045, 5,218,105 and 5,459,255). The modified oligonucleotide may have enhanced stability in the presence of nucleases and enhanced binding affinity to target mRNA.

The antisense oligonucleotide may be synthesized in vitro by an ordinary method and administered to the body, or may be synthesized in vivo. A method for synthesizing antisense oligonucleotide in vitro employs RNA polymerase I. A method for synthesizing antisense RNA in vivo involves performing transcription of antisense RNA using a vector containing a multicloning site (MCS) in the opposite direction. Such antisense RNA preferably contains a translation stop codon in its sequence to block translation into a peptide sequence.

Design of the antisense oligonucleotide useful in the present invention may be easily performed by the method known in the art with reference to the base sequence of human Prx II (SEQ ID NO. 37) (Weiss, B. (ed.): Antisense Oligodeoxynucleotides and Antisense RNA: Novel Pharmacological and Therapeutic Agents, CRC Press, Boca Raton, Fla., 1997; Weiss, B., et al., Antisense RNA gene therapy for studying and modulating biological processes. Cell. Mol. Life Sci., 55:334-358(1999).

As used herein, the term "siRNA" refers to a nucleic acid molecule that is able to mediate RNA interference or gene silencing (reference: WO 00/44895, WO 01/36646, WO 99/32619, WO 01/29058, WO 99/07409 and WO 00/44914). Since siRNA can suppress the expression of the target gene, it provides an effective way of gene knockdown or genetic therapy. First discovered in plants, worms, fruit flies and parasites, siRNA has been recently developed and used for studies of mammalian cells.

In the case in which the siRNA molecule is used in the present invention, it may have a structure in which its sense strand (a sequence corresponding to the Prx II mRNA sequence) and its antisense strand (a sequence complementary to the Prx II mRNA sequence) form a double strand. Alternatively, it may have a single-stranded structure having self-complementary sense and antisense strands.

The siRNA is not limited to those in which double-stranded RNA moieties constitute complete pairs, but includes the unpaired moieties such as mismatch (corresponding bases are not complementary), bulge (no corresponding base in one chain), etc. The total length of the siRNA may be 10 to 100 bases, preferably 15 to 80 bases, more preferably 20 to 70 bases.

The end of the siRNA may be either blunt or cohesive as long as it is capable of suppressing the expression of the Prx II gene via RNA interference (RNAi). The cohesive end may be either 3'- or 5'-cohesive end.

In the present invention, the siRNA molecule may have a short nucleotide sequence (e.g., about 5-15 nucleotides) inserted between the self-complementary sense and antisense strands. In this case, the siRNA molecule formed from the expression of the nucleotide sequence forms a hairpin structure via intramolecular hybridization, resulting in a stem-and-loop structure overall. The stem-and-loop structure is processed in vitro or in vivo to give an activated siRNA molecule capable of mediating RNAi. The siRNA of the present invention may be selected from the group consisting of SEQ ID NOS. 1 to 4.

As used herein, the term "aptamer" refers to a nucleic acid molecule having a binding affinity for a particular target molecule. The aptamer can also inhibit the activity of a particular target molecule by binding to the particular target molecule. The aptamer of the present invention may be an RNA, a DNA, a modified nucleic acid or a mixture thereof. The aptamer of the present invention can also be in a linear or circular form. The aptamer of the present invention is not particularly limited to its length. Typically, it may have a length of approximately 15-200 nucleotides, for example, approximately 100 nucleotides or less, preferably approximately 80 nucleotides or less, more preferably approximately 60 nucleotides or less, and most preferably approximately 45 nucleotides or less. The aptamer of the present invention may also have a length of approximately 18, 20 or 25 nucleotides or more. When the total number of nucleotides is smaller, chemical synthesis and mass-production will be easier, and there is a major advantage in terms of cost. Chemical modification is also easy, stability in the body is high, and toxicity is low.

The aptamer of the present invention can be prepared by utilizing the SELEX method or an improved version thereof [for example, Ellington et al., Nature, 1990 346, 818-822; Tuerk et al., Science, 1990 249, 505-510]. The SELEX method is a method of selecting an oligonucleotide specifically binding to the target molecule from, an oligonucleotide pool having 10-14 different, nucleotide sequences. The oligonucleotide used has a random sequence of about 40 residues, which is flanked by primer sequences. This oligonucleotide pool is allowed to mix with a target, molecule, and only the RNA that has bound to the target molecule is collected using a filter or the like. The oligonucleotide collected is amplified by RT-PCR, and this is used as a template for the next round. By repeating this operation about 10 times, an aptamer that binds specifically to the target molecule can be acquired. By increasing the number of rounds or using a competing substance, an aptamer exhibiting a stronger binding potential for the target molecule is concentrated and selected. Hence, by adjusting the number of rounds of SELEX and/or changing the competitive condition, aptamers with different binding forces or binding modes, and aptamers with the same binding force or binding mode but different base sequences can be obtained in some cases. The SELEX method includes a process of amplification by PCR; by causing a mutation by using manganese ions or the like in the process, it is possible to perform SELEX with higher diversity.

In addition to the known SELEX method, aptamers can be also obtained using the Cell-SELEX method for complex targets, living cells or tissues (Guo et al. Int. J. Mol. Sci., 9(4): 668, 2008), and the Cell-SELEX method has the advantage of direct selection of aptamers against disease without previous knowledge of the target molecule on the surface. Moreover, the Cell-SELEX method is advantageous over the conventional SELEX method in that a functional approach for the target protein in its physiological state is possible during the selection procedure because it may not show its intrinsic properties, when isolated.

Meanwhile, an aptamer binds to the target molecule in a wide variety of binding modes, such as ionic bonds based on the negative charge of the phosphate group, hydrophobic bonds and hydrogen bonds based on ribose, and hydrogen bonds and stacking interaction based on nucleic acid bases. In particular, ionic bonds based on the negative charge of the phosphate group, which are present in the same number as the number of constituent nucleotides, are strong, and bind to lysine and arginine being present on the surface of the positive charge of protein. For this reason, nucleic acid bases not involved in the direct binding to the target molecule can be substituted. In particular, because the region of the stem structure has already formed base pairs and faces the inside of the double helical structure, nucleic acid bases are unlikely to bind directly to the target molecule. Therefore, even when a base pair is replaced with another base pair, the activity of the aptamer often does not decrease. In structures wherein no base pairs are formed, such as loop structures, provided that the nucleic acid base is not involved in the direct binding to the target molecule, base substitution is possible. For example, at the 2'-position of ribose, a hydroxy group is substituted by any atom or group. Examples of the atom or group may include hydrogen atom, fluorine atom or —O-alkyl group (e.g., —O—$CH_3$), —O-acyl group (e.g., —O—CHO), and amino group (e.g., —$NH_2$). The aptamer, unless the functional group involved in the direct binding to the target molecule is substituted or deleted, often retains the activity thereof.

In addition, aptamers are easily modifiable because they permit chemical synthesis. For aptamers, by predicting the secondary structure using the MFOLD program, or by predicting the steric structure by X-ray analysis or NMR analysis, it is possible to predict to some extent which nucleotide can be substituted or deleted, and where to insert a new nucleotide. A predicted aptamer with the new sequence can easily be chemically synthesized, and it can be determined whether or not the aptamer retains the activity using an existing assay system.

The aptamer of the present invention may be one wherein a sugar residue (e.g., ribose) of each nucleotide has been modified to increase the binding activity, stability, drug deliverability and the like. As examples of the modification in a sugar residue, replacement of the oxygen atom at the 2'-position, 3'-position and/or 4-'-position of the sugar residue with another atom, and the like can be mentioned. As the kind of the modification, fluorination, O-alkylation (e.g., O-methylation, O-ethylation), O-arylation, S-alkylation (e.g., S-methylation, S-ethylation), S-arylation, and amination (e.g., —NH) can be mentioned. Such alterations in the sugar residue can be performed by a method known per se (e.g., Sproat et al., Nucle. Acid. Res, 1991 19, 733-738; Cotton et al., Nucl. Acid. Res. 1991 19, 2629-2635; Hobbs et al., Biochemistry 1973 12, 5138-5145).

The aptamer of the present invention may also have a nucleic acid base (e.g., purine or pyrimidine) altered (e.g., by chemical substitution) to increase binding activity. As examples of such alterations, pyrimidine alteration at the 5-position, purine alteration at the 6- and/or 8-position(s), alteration with an extracyclic amine, substitution with 4-thiouridine, and substitution with 5-bromo or 5-iodo-uracil can be mentioned.

The phosphate group contained in the aptamer or the present invention may be altered to confer resistance to nuclease and hydrolysis. For example, the P(O)O group may be substituted with P(O)S (thioate), P(S)S (dithioate), P(O)$NR_2$ (amidate), P(O)R, R(O)OR', CO or $CH_2$ (formacetal) or 3'-amine (—NH—$CH_2$—$CH_2$—) [wherein each unit of R or R' is independently H or a substituted or unsubstituted alkyl (e.g., methyl, ethyl)]. The joining group is, for example, —O—, —N— or —S—, and nucleotides can bind to an adjoining nucleotide via these joining groups.

The alterations may also include alterations such as capping at 3' and 5'. An alteration can further be performed by adding to an end a polyethyleneglycol, amino acid, peptide, inverted dT, nucleic acid, nucleosides, Myristoyl, Lithocolic-oleyl, Docosanyl, Lauroyl, Stearoyl, Palmitoyl, Oleoyl, Linoleoyl, other lipids, steroids, cholesterol, caffeine, vitamins, pigments, fluorescent substances, anticancer agents, toxins, enzymes, radioactive substances, biotin and the like. For such alterations, see, for example, U.S. Pat. Nos. 5,660,985 and 5,756,703.

In addition, aptamers are attached to the surface of liposomes or nanoparticles to deliver an anticancer agent, a toxin, a tumor suppressor gene, and a siRNA (small interfering RNA) encapsulated in the liposomes or nanoparticles to the target cell.

In the present invention, the inhibitor of Prx II protein, in particular, its activity is preferably an antibody, a peptide, a low-molecular-weight compound, or a natural extract that specifically binds to Prx II.

The antibody that specifically binds to Prx II protein to inhibit its activity is a polyclonal or monoclonal antibody, and preferably a monoclonal antibody. The antibody against Prx II protein may be prepared by the typical method known in the art, for example, a fusion method (Kohler and Milstein, European Journal of Immunology, 6:511-519(1976)), a recombinant DNA method (U.S. Pat. No. 4,816,56) or a phage antibody library method (Clackson et al, Nature, 352:624-628 (1991) and Marks et al, J. Mol. Biol., 222:58, 1-597(1991)). The general procedures for antibody production are described in Harlow, E. and Lane, D., Using Antibodies: A Laboratory Manual, Cold Spring Harbor Press, New York, 1999; Zola, H., Monoclonal Antibodies: Manual of Techniques, CRC Press, Inc., Boca Raton, Fla., 1984; and Coligan, Current Protocols In immunology, Wiley/Greene, N.Y., 1991, which are incorporated herein by references. For example, the preparation of hybridoma cell lines for monoclonal antibody production is done by fusion of an immortal cell line and the antibody-producing lymphocytes. This can be done by techniques well known in the art. Polyclonal antibodies may be prepared by injection of the Prx II protein antigen to suitable animal, collecting antiserum containing antibodies from the animal, and isolating specific antibodies by any of the known affinity techniques.

In the present invention, the antibody may include a single chain variable region fragment (scFv). The single chain variable region fragment may consist of "light chain variable region (VL)-linker-heavy chain variable region (VH)". The linker means an amino acid sequence having a predetermined length, which functions to connect variable regions of the heavy chain and light chain.

The peptide that specifically binds to Prx II to inhibit its activity may be obtained by the typical method known in the art, for example, by phage display (Smith G P, "Filamentous fusion phage: novel expression vectors that display cloned antigens on the virion surface". Science 228 (4705):1315-1317 (1985); Smith G P, Petrenko V A, "Phage display". Chem. Rev. 97 (2) :391-410(1997)).

The low-molecular-weight compound inhibiting Prx II activity may be easily obtained by the screening method described below.

According to another embodiment, the present invention provides a method for screening angiogenesis inhibitors, comprising the steps of (a) analyzing Prx II protein activity or Prx II gene expression after treatment of a test material; and (b) determining the test material as an angiogenesis inhibitor when the Prx II protein activity or the Prx II gene expression after the treatment of the test material is inhibited, compared to the non-treatment of the test material. The Prx II protein activity or the Prx II gene expression can be analyzed in vivo or in vitro.

The method of screening angiogenesis inhibitors that inhibit Prx II protein activity of the present invention may be performed by screening a material that inhibits the activity of Prx II protein or binds to Prx II protein. In this case, any of the isolated form of Prx II and the Prx II protein included in the cell may be used as the Prx II protein. Specifically, the method of screening angiogenesis inhibitors of the present invention may include the steps of (a) reacting a test material with a buffer solution containing Prx II protein, thioredoxin (Trx), thioredoxin reductase (TrxR) and NADPH; (b; reacting the reaction product of step (a) with $H_2O_2$ to prepare an experimental group; (c) reacting a buffer solution containing Prx II protein, thioredoxin (Trx), thioredoxin reductase (TrxR) and NADPH with $H_2O_2$ to prepare a control group; (d) measuring and comparing the absorbance of the experimental group and the control group; and (e) determining the test material as an inhibitor when the absorbance of the experimental group is lower than that of the control group. The thioredoxin and thioredoxin reductase are preferably derived from yeast.

Further, to screen the specific Prx II inhibitors, one or more selected from the group consisting of Prx I (base sequence: SEQ ID NO. 38), III (base sequence: SEQ ID NO. 39), IV (base sequence: SEQ ID NO. 40), and V (base sequence: SEQ ID NO. 41) are subjected to the above steps, and the test material can be determined, as an angiogenesis inhibitor, when there is no difference in absorbance between the control group and the experimental group performed with one or more selected from the group consisting of Prx I, III, IV and V. Specifically, the screening method of the present invention may also include the steps of (a) reacting a test material with a buffer solution containing Prx II protein, thioredoxin (Trx), thioredoxin reductase (TrxR) and NADPH; (b) reacting the reaction product of step (a) with $H_2O_2$ to prepare a first experimental group; (c) reacting a buffer solution containing Prx II protein, thioredoxin (Trx), thioredoxin reductase (TrxR) and NADPH with $H_2O_2$ to prepare a first control group; (d) measuring and comparing the absorbance of the first experimental group and the first control group; (e) reacting the test material with a buffer solution containing one or more protein selected from the group consisting Prx I, III, IV and V, thioredoxin (Trx), thioredoxin reductase (TrxR) and NADPH; (f) reacting the reaction product of step (e) with $H_2O_2$ to prepare a second experimental group; (g) reacting a buffer solution containing one or more protein selected from the group consisting Prx I, III, IV and V, thioredoxin (Trx), thioredoxin reductase (TrxR) and NADPH with $H_2O_2$ to prepare a second, control group; (h) measuring and comparing the absorbance of the second experimental group and the second control group; and (i) determining the test material as an inhibitor when there is no difference in absorbance between the second control group and the second experimental group, while the absorbance of the first experimental group is lower than that of the first control group. The absorbance can be measured at 340 nm.

The screening method of the present invention may be carried out by various processes, especially by a high throughput method through diverse binding assays known to those skilled in the art.

In the screening method of the present invention, the test material or Prx II protein may be labeled with a detectable label. For example, the detectable label includes, but is not limited to, a chemical label (e.g., biotin), an enzyme label (e.g., horseradish peroxidase, alkaline phosphatase, peroxidase, luciferase, β-galactosidase and β-glucosidase), a radio-active label (e.g., $C^{14}$, $I^{125}$, $P^{32}$ and $S^{35}$), a fluorescence label (e.g., coumarin, fluorescein, FITC (fluoresein Isothiocyanate), rhodamine 6G, rhodamine B, TAMRA (6-carboxy-tetramethyl-rhodamine), Cy-3, Cy-5, Texas Red, Alexa Fluor, DAPI (4,6-diamidino-2-phenylindole), HEX, TET, Dabsyl and FAM), a luminescent label, a chemiluminescent label, FRET (fluorescence resonance energy transfer) label or a metal label (e.g., gold and silver).

For using the detect ably labeled Prx II protein or test material, a binding of Prx II protein with the test material may be analyzed through the signal generated by the label. If alkaline phosphatase is used as a label, bromo-chloro-indolylphosphate (BCIP), nitro blue tetrazolium (NBT), naphthol-AS-B1-phosphate and ECF (enhanced chemifluorescence) may be used as a substrate. If horseradish peroxidase is used as a label, chloronaphtol, aminoethylcarbazol, diaminobenzidine, D-luciferin, lucigenin (bis-N-methylacridinium nitrate), resorufin benzyl ether, luminol, Amplex Red reagent (10-acetyl-3,7-dihydroxyphenoxazine), HYR (p-phenylenediamine-HCL and pyrocatechol), TMB (tetramethylbenzidine), ARTS (2,2'-Azine-di[3-ethylbenzthiazoline sulfonate]), OPB (o-phenylenediamine) and naphtol/pyronin may be used as a substrate.

Alternatively, the binding of Prx II protein with the test material may be measured without the labeling of the interactants. For example, a microphysiometer may be used to analyze the binding of Prx II protein with the test material. The microphysiometer is a device for determining the cell's environment-acidifying rate using LAPS (light-addressable potentiometric sensor). The change of acidifying rate may be used as an indicator for the binding of Prx II protein with the test material (McConnell et al., Science 257:1906-1912 (1992)).

The binding capacity of the test material to Prx II protein may be determined by real-time BIA (bimolecular interaction analysis) (Sjolander & Urbaniczky, Anal. Chem., 63:2338-2345(1991), and Szabo et al., Curr. Opin. Struct. Biol. 5:699-705(1995)). BIA is a real-time analyzing technique for the specific interaction without the labeling of interactants (e.g., BIAcore™). The change of SPR (surface plasmon resonance) is used as an indicator of real-time reaction between the molecules.

Further, the screening method of the present invention may be performed according to a two-hybrid or three-hybrid method (U.S. Pat. No. 5,283,317; Zervos et al., Cell 72, 223-232, 1993; Madura et al., J. Biol. Chem. 268, 12046-12054, 1993; Bartel et al., BioTechniques 14, 920-924, 1993; Iwabuchi et al., Oncogene 8, 1693-1696, 1993; and WO 94/10300). In this case, Prx II protein can be used as a "bait" protein. According to this method, a substance, in particular, a protein binding to Prx II protein can be screened. The two-hybrid system is based on the modularity of transcription factors that consist of splittable DNA-binding and activating domains. Briefly, this technique employs two DNA constructs. For example, in one construct, a Prx II-encoding polynucleotide is fused with a DNA binding domain-encoding polynucleotide of a known transcription factor (e.g., GAL-4). In the other construct, a DNA sequence encoding the protein to be analyzed ("prey" or "sample") is fused with a polynucleotide encoding the activating domain of the known transcription factor. When the bait and the prey interact to form a complex in vivo, the DNA-binding and activating domains of the transcription factor are brought in proximity and transcription of reporter genes (e.g., LacZ) occur. The detection of the expression of the reporter gene confirms that the analyte protein binds with the Prx II protein, meaning that it can be utilized as an angiogenesis inhibitor.

According to the method of the present invention, first, the test material to be analyzed is contacted with the Prx II protein. In the context related to the screening method of the present invention, the term "test material" refers to an unknown substance which is screened to test whether it affects the activity of Prx II protein. The test material may be a chemical, a peptide or a natural extract, but is not limited thereto. The test sample analyzed by the screening method of the present invention may be an individual compound or a mixture of compounds (e.g., natural extract, or cell or tissue culture). The test material may be obtained from a library of synthetic or natural compounds. The method for obtaining the library of such compounds is known in the art. A library of synthetic compounds is commercially available from Maybridge Chemical Co. (UK), Comgenex (USA), Brandon Associates (USA), Microsource (USA) and Sigma-Aldrich (USA), and a library of natural compounds is commercially available from Pan Laboratories (USA) and MycoSearch (USA). The test material may be obtained through various known combinational library methods. For example, it may be acquired by a biological library method, a spatially-addressable parallel solid phase or solution phase library method, a synthetic library method requiring deconvolution, a "1-bead/1-compound" library method, and a synthetic library method using affinity chromatography selection. The methods for obtaining the molecular libraries are described in DeWitt et al., Proc. Natl. Acad. Sci. U.S.A. 90, 6909, 1993; Erb et al. Proc. Natl. Acad. Sci. U.S.A. 91, 11422, 1994; Zuckermann et al., J. Med. Chem. 37, 2678, 1994; Cho et al., Science 261, 1303, 1993; Carell et al., Angew. Chem. Int. Ed. Engl. 33, 2059, 1994; Carell et al., Angew. Chem. Int. Ed. Engl. 33, 2061; Gallop et al., J. Med. Chem. 37, 12 33, 1994.

Subsequently, the activity of the Prx II protein treated with the test material is measured. If down-regulation of the activity of the Prx II protein is observed as the result thereof, the rest material may be decided as an angiogenesis inhibitor.

If the screening method of the present invention is performed by analyzing the expression of Prx II gene, the measurement of the expression level of Prx II gene can be carried out by a variety of methods known in the art. For example, RT-PCR (Sambrook et al., Molecular Cloning. A laboratory Manual, 3rd ed. Cold Spring Harbor Press (2001)), Northern blotting (Peter B. Kaufma et al., Molecular and Cellular Methods in Biology and Medicine, 102-108, CRC press), hybridization using cDNA microarray (Sambrook et al., Molecular Cloning. A Laboratory Manual, 3rd ed. Cold Spring Harbor Press (2001)) or in situ hybridization (Sambrook et al., Molecular Cloning, A Laboratory Manual, 3rd ed. Cold Spring Harbor Press (2001)) may be used.

If the analysis is performed according to RT-PCT protocol, total RNA is first isolated from cells treated with a test material to be analyzed, and a first cDNA strand is then synthesized using oligo dT primer and reverse transcriptase. Then, PCR amplification is performed using the first cDNA strand, as a template and a Prx II gene-specific primer set. Finally, the PCR amplified products are resolved by electrophoresis and bands are analyzed for assessing the expression level of the Prx II gene.

The change in the amount of the Prx II protein may be measured by various immunoanalysis techniques known in the art. For example, the change in the amount, of the Prx II protein may be measured by radioactivity immunoanalysis, radioactive immunoprecipitation, immunoprecipitation, enzyme-linked immunosorbent assay (ELISA), capture-ELISA, inhibition or competition assay, or sandwich immunoanalysis, but is not limited thereto.

According to a preferred embodiment of the present invention, the angiogenesis inhibitor found by the above described screening method can be used for the treatment or prevention of cancer, diabetic retinopathy, retinopathy of prematurity, corneal transplant rejection, neovascular glaucoma, erythrosis, proliferative retinopathy, psoriasis, hemophilic arthropathy, capillary proliferation in atherosclerotic plaques, keloid, wound granulation, rheumatoid arthritis, ostarthritis, autoimmune diseases, Crohn's disease, atherosclerosis, cat scratch disease, ulcer, cirrhosis, glomerulonephritis, diabetic nephropathy, malignant nephrosclerosis, thrombotic microangiopathy, organ-transplant rejection, glomerulopathy, diabetes, inflammation or neurodegenerative diseases, but is not limited thereto.

Further, the present invention relates to a kit for screening angiogenesis inhibitors for performing the screening method. The kit may include Prx II protein and a reaction buffer solution, and further include thioredoxin, thioredoxin reductase, NADPH and $H_2O_2$. The thioredoxin and thioredoxin reductase may be derived from yeast. In addition, the kit may further include EDTA for Prx reaction, and a HEPES-NaOH buffer solution as the reaction buffer solution (pH 6.0-8.0). $H_2O_2$ is included for detection of the reaction product. In order to enhance the reaction stability, glycerol may be further included, in addition to the above components. Korean Patent Publication No. 10-2006-0020140 by the present inventors is incorporated herein as a reference. In order to screen Prx II-specific inhibitors, one or more selected, from the group consisting of Prx I, III, IV and V may be further included as a control group in the kit.

Throughout this application, various patents and publications are referenced and citations are provided in parentheses. The disclosure of these patents and publications in their entities are hereby incorporated by reference into this application in order to more fully describe this invention and the state of the art to which this invention pertains.

Hereinafter, the present invention will be described in more detail with reference to Examples. It would be obvious to those skilled in the art that these Examples are for illustrative purposes only, and the present invention is not intended to be limited thereby.

Antibodies

Antibodies against pS1177-eNOS, eNOS, pY783-PLCγγ1, pTpY-p38, p38, pTpY-ERK, pYVEGFR-2 (pY951 and pYH75) and flotillin-2 were purchased from Cell Signaling Technology. Antibodies for Flk-1 (sc-504, sc-6251), Fit-1 (sc-316), and ERE 2 (sc-154-G) were purchased from Santa Cruz Biotechnology. Anti-phosphotyrosine (4G10), anti-pY1214-KDR and anti-pY1059-KDR antibodies were purchased from Upstate Biotechnology. Antibodies against caveolin-1 were purchased from BD Bioscience. Anti-α-tubulin was purchased from Sigma-Aldrich. Alexa Fluor 488-conjugated rabbit anti-goat and Alexa Fluor 568-conjugated rabbit anti-mouse secondary antibodies were purchased from Invitrogen. Rabbit, polyclonal antibodies against catalase, Prx III, Prx IV, GPxl, and hyperoxidized 2-cys Prxs were obtained from AbFrontier Co. Rabbit polyclonal antisera against Prx I and Prx II were produced and affinity-purified using agarose beads conjugated with antigen recombinant proteins. Rabbit antibody specific to NOX4 was produced by immunization with a mixture of three different peptides derived from human NOX4 protein sequence. The anti-NOX4 rabbit antisera were affinity-purified using antigenic peptide-conjugated agarose beads.

Cell Culture

Human aortic endothelial cell (HAEC), human aortic smooth muscle cell (HASMC), human umbilical vein endothelial cell (HUVEC), and human lung blood microvascular endothelial cell (HMVEC) were purchased from Clonetics-Eio Whittaker. HAECs and HUVECs were grown at 37° C. in a humidified, incubator containing 5% $CO_2$ in Endothelial Basal Medium (EBMTM-2) SingleQuotes® with full supplements (Clonetics-BioWhittaker; Cat no. cc-4176 for HAEC and HUVEC, Cat no., cc-4147 for HAMEC). SMCs were grown in Smooth Muscle Cell Basal Medium (SmBMTM) SingleQuots® with full supplements (Cat no. cc-4149). Cells with typical passage number of 7 to 8 were used for the study.

For isolation of mouse aortic endothelial cells (MAECs), the thoracic aortas harvested from eighteen-week-old mice were used. After removing fatty tissue, the aorta was cross-sectioned into 2-3 mm rings with micro-spring scissors. The aorta pieces were subsequently placed on 300 μL of liquefied Matrigel (BD Bioscience cat #354234) on 24-well dishes and incubated at 37° C. for 7 days until endothelial, sprouts developed. Aortic rings were removed carefully at this point, without disturbing the endothelial sprouts, and the isolated cells were selected, and passaged with Dispase (BD Bioscience cat#354235). Then, the cells were plated onto a 0.1% gelatin-coated culture plate, and cultured for an additional 4 days. Cells used in all the experiments did not exceed passage 3. The purity of the isolated cells was confirmed by CD31 staining.

siRMAs and Transfection

Sequences of the four siRNA duplexes for human Prx II were 5'-CGCUUGUCUGAGGAUUACGUU-3' (#1, SEQ ID NO. 1), 5'-AGGAAUAUUUCUCCAAACAUU-3' (#2, SEQ ID NO. 2), 5'-GACGCUUGUCUGAGGAUUAUU-3' (#3, SEQ ID NO. 3) and 5'-UCAAAGAGGUGAAGCUGUCUU-3' (#4, SEQ ID NO. 4). The Prx II siRNA duplex #1 was mainly used for the study. Sequences of the four siRNA duplexes for human Prx I were 5'-ACUCAACUGC-CAAGUGAUUUU-3' (#1, SEQ ID NO. 5), 5'-CCACG-GAGAUCAUUGCUUUUU-3' (#2, SEQ ID NO. 6), 5'-GGUCAAUACACCUAAGAAAUU-3' (#3, SEQ ID NO. 7) and 5'-UAUGCCAGAUGGUCAGUUUUU-3' (#4, SEQ ID NO. 8); those for human GPxl, 5'-GCAAGGUACUACU-UAUCGAUU-3' (#1, SEQ ID NO. 9), 5'-UGAAUUCCCU-CAAGUACGUUU-3' (#2, SEQ ID NO. 10), 5'-GGAGAACGCCAAGAACGAAUU-3' (#3, SEQ ID NO. 11) and 5'-GCAACCAGUUUGGGCAUCAUU-3' (#4, SEQ ID NO. 12). A Prx III-specific siRNA was previously described in Chang, T. S. et al., (J Biol Chem 2004 279 (40), 41975-41984). The firefly luciferase siRNA were purchased or synthesized from Dharmacon. SiRNA duplexes for human VEGFR-1 (Cat No. sc-29319), VEGFR-2 (Cat No. sc-29318), and Prx IV (Cat. No. sc-40835) was purchased from Santa Cruz Biotechnology. The sequence of siRNA specific to human NOX4 was 5'-GUCAACAUCCAGCU-GUACC-3' (SEQ ID NO. 13). Human caveolin-1 siRNA, 5'-GCAUCAACUUGCAGAAAGAUU-3' (SEQ ID NO. 14) was purchased from Qiagen. Unless otherwise stated, the endothelial cells (ECs) were transfected with the siRNA duplexes for 24 hrs using lipofectamine RNAi MAXTM (Invitrogen). Then, the cells were serum-starved for an additional 18 hrs in media containing 0.5% fetal bovine serum before VEGF stimulation.

Endothelial Cell Function Assays

For proliferation assay, the HAECs were seeded at a density of 4000 cells/well in a final volume of 80 μL onto 96-well plates containing siRNA-transfection reagent mixtures. After a 24-hr transfection, the cells were serum-starved, for 24 hrs, and then placed in EBM-2 basal medium supplemented with VEGF-A165 (25 ng/mL, Cat no. 293-VE, R&D systems) for an additional 24 hrs. The extent of cell proliferation was measured using a WST-1 cell proliferation assay kit (Roche Diagnostics, USA) and the cell number was expressed as absorbance at 450 nm averaged from triplicate wells after subtracting the turbidity at 600 nm.

The migration assay was performed in 24-well Transwell culture chambers. The bottom of the filter was coated with gelatin B (1 mg/mL) and air-dried for 1 hr. HAECs ($6 \times 10^3$) were added to the upper chambers, which contained transfection complexes. After 24 hrs, the transfected. HAEC were serum-starved overnight. Solutions of VEGF-A (25 ng/mL) were prepared, in basal media with 0.5% BSA and added to the bottom chambers. The upper chamber wells were filled with each basal media containing 0.5% BSA. Transwell chambers were incubated at 37° C./5% $CO_2$ for 8 hrs. After incubation, the non-migrated cells were removed from the top of the filters, and the cells that migrated onto the bottom of filters were fixed and stained with 0.6% hematoxylin and 0.5% eosin. The stained cells were photographed and counted. The number of migrating cells was averaged from duplicate wells.

For tube formation, the HAECs (50,000 cells/well) were placed on 12-well culture dishes coated with growth factor-reduced Matrigel matrix (BD Bioscience, cat #354230). Cells were cultured for 18 hrs in the EBM-2 media containing 0.5% serum medium in the presence or absence of VEGF-A (25 ng/mL). Thereafter, the cell images were taken from five random visual fields per sample and the total length of the tubes were quantitatively analyzed using an Image-Pro Plus version 6.2 (Media Cybernetics).

Immunoprecipitation, In Vitro Kinase Assay, and Immunoblot Analyses

At the appropriate time, the culture media were aspirated and cells were lysed in extraction buffer (TEB) containing 20 mM Hepes (pH 7.0), 1% Triton X-100, 150 mM NaCl, 10% glycerol, 1 mM EDTA, 2 mM EGTA, 1 mM DTT, 5 mM $Na_3VO_4$, 5 mM NaF, 1 mM AEBSF, aprotinin (5 μg/mL), and leupeptin (5 μg/mL). After brief centrifugation, the protein content of samples was quantified using the Bradford reagent (Bio-Rad). For immunoprecipitation, the resulting supernatants (120 μg proteins) were pre-cleaned with 10 μL of protein-A/G Sepharose 4 Fast Flow beads (Amersham Biosciences) for 1 hr, incubated overnight with 2 μg of the indicated antibodies, and further incubated at 4° C. for 3 hrs with 20 μL of protein-A/G Sepharose beads. Immunocomplexes were washed three times with 1 mL of TEB and then subjected to either in vitro kinase assay or immunoblotting.

The in vitro kinase assay was done as previously described in Choi, M. H. et al., (Nature 2005 435 (7040), 347-353). Briefly, the immunocomplexes precipitated with rabbit anti-flk-1(sc-504) antibody were incubated with 30 μL of kinase buffer (20 mM HEPES pH 7.5, 20 mM $MgCl_2$, 20 mM β-glycerophosphate, and 200 μM $Na_3VO_4$) containing 5 μg of $\gamma$-$^{32}$[P]-ATP and 0.5 μg GST-PLCγ1 at 30° C. for 10 minutes. The reaction was stopped by the addition of a SDS sample buffer. The samples were then boiled and separated on SDS denaturing gel. The gel was vacuum-dried and subjected to autoradiography.

For immunoblotting, cell lysates or the immunoprecipitates were mixed with 5× Laemmli sample buffer and boiled for 5 minutes. The samples were separated on a SDS denaturing gel and then electrophoretically transferred onto nitrocellulose membranes, which were subsequently subjected to immunoblotting. In order to block non-specific binding, the membrane was reacted with TBS (Tris-buffered saline; TBST) containing 0.5% Tween-20 and 5% nonfat milk at room temperature for 1 hour. The above described blots were reacted with each primary antibody in TBST containing 5% nonfat milk or BSA at 4° C. for overnight. After washing with TBST, the blots were reacted with horseradish peroxidase-conjugated goat anti-mouse immunoglobulin (IgG; 1:5000 dilution) or goat anti-rabbit IgG (1:3000 dilution) at room temperature for 45 minutes. Protein bands were detected using an Amersham ECLTM detection system (GE healthcare). When necessary, the membranes were stripped by shaking them for 60 minutes at 37° C. in 67 mM Tris (pH 6.7), 2% SDS, 100 mM 2-mercaptoethanol and reprobed. with the appropriate pan antibody.

Protein Tyrosine Phosphatase (PTP) Analysis

All steps were performed in an anaerobic incubator, and the reagents were degassed before analysis. A Universal tyrosine phosphatase assay kit (cat. MK-411) purchased, from TAkak Bio. was used to analyze PTP activity. Briefly, each lysate was serially diluted 20-fold using a phosphatase reaction solution. For three independent experiments, a standard control group and serial dilutions of each sample were added to PTP substrate-fixed wells. Addition of the diluted samples induces dephosphorylation. After washing and blocking, anti-phosphotyrosine-HRP was added to each well, and reacted. Absorbance was measured in the substrate-reacted well at 450 nm.

Detection and Measurement of Reactive Oxygen Species

HAECs were rinsed with Endothelial Basal Medium without phenol red (EBM, Lonza) and immediately incubated with 5 µM 5,6-chloromethyl-2',7'-dichlorodihydrofluorescein diacetate (CM-$H_2$DCFDA) (Molecular Probe) at 37° C. for 5 minutes. After briefly washing the cell with EBM, the fluorescence images were taken by fluorescence microscope (Axiovert 200 Basic standard, Zeiss, Germany). The relative DCF fluorescence was calculated by averaging the levels of fluorescence from 50-80 cells after subtracting the background fluorescence.

Reverse Transcription-PCR

Total RNA was isolated from HAECs using Trizol (Invitrogen), and the cDNA was synthesized using M-MLV Reverse Transcriptase (Promega). RT-PCR was performed using the following primers: for human Prx II, (sense) 5'-CCGCTCGAGATGGCCTCCGGTAACGCG-3' (SEQ ID NO. 15) and (antisense) 5'-CGGGATCCCTAATTGT-GTTTGGAGAA-3' (SEQ ID NO. 16); for human VEGFR-1, (sense) 5'-ATTTGTGATTTTGGCCTTGC-3' (SEQ ID NO. 17) and (antisense) 5'-CAGGCTCATGAACTTGAAAGC-3' (SEQ ID NO. 18); for human VEGFR2, (sense) 5'-GTGAC-CAACATGGAGTCGTG-3' (SEQ ID NO. 19) and (antisense) 5'-CCAGAGATTCCATGCCACTT-3' (SEQ ID NO. 20); for GAPDH, (sense) 5'-TTCATTGACCTCAACTA-CAT-3' (SEQ ID NO. 21) and (antisense) 5'-GAGGGGC-CATCCACAGTCTT-3' (SEQ ID NO. 22).

For real-time quantitative PCR (qPCR), 8 µL of the 10-fold diluted HAEC cDNA was mixed with 10 µL of the SYBR Green Master Mix (Applied Biosystems) and 1 µL of each primer (10 µM). The PCR reactions were performed in triplicate for 40 cycles (95° C. for 15 seconds and 60° C. for 1 minutes) in a 7300 Real Time PCR System (Applied Biosystems). After completing the reaction cycles, the melting point was checked for specificity. The PCR data were quantified as a $2^{-\Delta\Delta Ct}$ value relative to that of endogenous β-actin.

The gene-specific primers for human NOX isoforms were obtained from Qiagen: hNOX1 (QT00025585), hNOX2 (QT01751869), hNOX3 (QT00044737), hNOX4 (QT00057498), hNOX5 (QT00021924), hDUOX1 (QT00038346) and hDUOX2 (QT00012236); specific primers for 3-actin were (sense) 5'-TGGATCAGCAAGCAG-GAGTAT-3' (SEQ ID NO. 23) and (antisense) 5'-GCATTTGCGGTGGCAGAT-3' (SEQ ID NO. 24).

Site-Directed Mutagenesis

A plasmid containing a full-length cDNA of mouse VEGFR-2 (mVEGFR2) was purchased from Open Biosystems (mRNA accession number, BC020530). The coding sequence of mVEGFR-2 was subcloned into pBluescript SK- (Stratagene) after amplification by a polymerase chain reaction using the forward and reverse primers (5'-AAT-CACGCGGCCGCACCATGGAGAGCAAGGCGCTGCT-AGC-3' (SEQ ID NO. 25) and 5'-AATCACCTCGAGAA-CAGGAGGTGAGCGCAGTGTGG-3' (SEQ ID NO. 26), wherein the NotI and XhoI sites are underlined, respectively) followed by restriction enzymatic digestion and ligation. A tandem hemagglutinin (HA) epitope tag (3×) was added to a carboxyl-terminus of mVEGFR-2 using SalI and XhoI sites.

Site-directed mutagenesis for Cys-to-Ser substitution was subsequently performed using the QuickChange kit (Stratagene) with the following primers: 5'-TTGCCCTTGGAT-GAGCGCTCTGAACGCTTGCCTTATGAT-3' (SEQ ID NO. 27) for C815S, 5'-GACAAGACAGCGAGTTC-CAAAACAGTAGCCGTCAAG-3' (SEQ ID NO. 28) for C860S, 5'-ACCTTGGAGCATCTCATCTCTTACAGCT-TCCAAGTGGCT-3' (SEQ ID NO. 29) for C1005S, 5'-GGGTCAAGATTGATGAAGAATTTTCTAG-GAGATTGAAAGAAGGAACTAG-3' (SEQ ID NO. 30) for C1114S, 5'-GCCTACCTCACCTGTTTCCTCTATGGAG-GAAGAGGAAGTGTG-3' (SEQ ID NO. 31) for C1199S, and 5'-GTATGGAGGAAGAGGAAGTGTCCGAC-CCCAAATTCCATTATGAC-3' (SEQ ID NO. 32) for C1206S, wherein the substituted bases are underlined. The NotI/XhoI fragments including the coding sequences of mVEGFR-2 wild type (WT) and CS mutants with in-frame HA tag were subcloned into pQ-CXIX retroviral expression vector (Clontech). All the constructs were verified by nucleotide sequencing. To enhance the transfection efficiency, the pQ vectors were linearized by digesting with PvuI.

Fluorescence Labeling of Reactive Cysteine Thiols

To monitor the redox state of VEGFR-2, HAECs were transfected with either control or Prx II siRNAs for 24 hrs and deprived of serum for 18 hrs. The cells were rinsed briefly with cold phosphate-buffered saline, frozen in liquid nitrogen, and then transferred to an anaerobic chamber. The cells were lysed in TEB containing 100 µM of Cy3-maleimide (GE Healthcare) and incubated at room temperature for 30 minutes to label the reduced thiols. After the reaction was quenched with 1 mM DTT, equal amounts of the Cy3-maleimide labeled samples were subjected to immunoprecipitation with an anti-VEGFR-2 antibody. The immunoprecipitates were reduced by incubating with 5 mM DTT for 20 minutes and washed three times with TEB. The immunoprecipitates were re-labeled with 100 µM of Cy5-maleimide (GE Healthcare) for 30 minutes at room, temperature and washed with TEB. The double-labeled, immunoprecipitates were boiled in a 2× sample buffer and separated on SDS-PAGE gel. The fluorescence images were taken using a Typhoon 9400 variable mode imager (GE Healthcare) and the levels of fluorescence were quantified by ImageQuant version 5.2 (Molecular Dynamics).

For 293T cells transfected with pQ plasmids encoding mVEGFR-2, the detection of $H_2O_2$-dependent cysteine oxidation was performed by the same labeling procedure, except using anti-HA antibody for precipitating the mVEGFR-2.

Recombinant Virus Production

For production of Prx II-expressing retrovirus, full-length cDNAs of human Prx II wild-type and C52S/C172S (CS) mutant, both with a Myc epitope tag, were cloned between the NotI and XhoI sites of pQ vector. The 293T cells seeded at a density of $7 \times 10^6$ cells per 15 cm. dish in DMEM supplemented with 10% FBS and 1% penicillin/streptomycin and then transfected with 20 μg each of gag/pol, VSV-G, and retroviral plasmids by the calcium phosphate method. Approximately 6 hrs after transfection, the medium was replaced with a fresh growth medium. The retrovirus-containing supernatant was collected twice at 24 hrs and 48 hrs after transfection, filtered by a 0.45 μm syringe filter to remove cell debris, and then stored at −80° C. until used. Recombinant adenoviral plasmids were produced by a bacterial homologous recombination system (He, T. C. et al., Proc Natl Acad Sci USA 1998 95 (5), 2509-2514). The cytosol-targeted human catalase (Cat-Cyto) with the carboxyl-terminal peroxisomal targeting sequence (-Lys-Ala-Asn-Leu-COOH) deleted was PCR-cloned from HeLa cDNA library using forward and reverse primers (5'-GGGGTAC-CATGGCTGACAGCCGG-3' (SEQ ID NO. 33) and 5'-GCG-GCAAGGGAGTAATCTAGAGC-3' (SEQ ID NO. 34) (wherein KpnI and XbaI sites are underlined). The PCR product was subcloned into pShuttle-CMV vectors. The mitochondrial-targeted human catalase (Cat-Mito) was PCR-cloned by the same strategy, except the forward primer 5'-CCCAAGCTTGCTGACAGCCGG-3' (SEQ ID NO. 35) (the HindIII site underlined). Subsequently, a pair of synthetic oligonucleotides encoding the mitochondrial targeting sequence (MTS) of human superoxide dismutase-2 were ligated in the 5' position to the amino-terminus of catalase in-frame using KpnI and HindIII sites. The membrane-targeted human catalase (Cat-Caax) was also PCR-cloned using the same strategy, except the reverse primer 5'-GCG-GCAAGGGAGTGCAAGTGTGTGCTCTC-CTAATCTAGAAAC-3' (SEQ ID NO. 36) with the lipidation sequence (CAAX box, -Cys-Lys-Cys-Val-Leu-Ser-) of H-Ras italicized and the Xba I site underlined. The pShuttle-CMV vectors encoding the modified catalases were linearized with PmeI and electroporated into BJ583 bacterial cells to obtain the recombinant adenoviral plasmids. The adenoviral production, purification, and titration were performed as previously described in He, T. C. et al., Proc Natl Acad Sci USA 95 (5), 2509-2514 (1998).

VEGF Binding Assay

HAECs ($5 \times 10^3$ cells/well) were cultured on 96-well plate and serum-starved for 18 hours. The cultured cells were placed in a binding buffer (25 mM HEPES (pH 7.4), 0.1% BSA in serum free DMEM), and then treated with $^{125}$I-labeled VEGF (80 pM; PerkinElmer Life Science). After four washes with a cold binding buffer, the cells were solubilized with 0.1 N NaOH. The receptor-bound radioactivity was determined using a gamma counter.

Preparation of Detergent-Insoluble Membrane

HAECs ($5 \times 10^7$) were washed twice with ice-cold MBS (25 mM 2-(N-morpholino)-ethanesulfonic acid (MES), pH 6.5, 0.15 M NaCl) and scraped off the dish in MBS. The suspension was adjusted to 0.2% Triton X-100 in a Bounce homogenizer at 4° C. by the addition of 2% Triton X-100 in MBS. After incubation for 10 minutes at 4° C., the cells were homogenized and mixed with 2 mL of 80% sucrose prepared in MBS at the bottom of an ultracentrifuge tube. A 5-30% discontinuous sucrose gradient was formed above (4 mL of 5% sucrose/4 mL of 30% sucrose, both in MBS lacking detergent), and ultracentrifugation was performed for 18 hrs at 39,000 rpm in an SW41 rotor (Beckman Instruments, Palto Alto, Calif., USA). Twelve 1 mL fractions were collected and used for SDS-PAGE analyses followed by immunoblotting.

Immunogold-Transmission Electron Microscopy

HAECs ($6 \times 10^7$ cells) were harvested and fixed for 5 minutes at room temperature in PBS with 0.5% glutaraldehyde. After rinsing with cold distilled water, they were dehydrated through an ethanol series at 4° C. They were infiltrated with an LR White resin (London Resin, Berkshire, England) at 4° C. and embedded in LR White resin in gelatin capsules. Polymerization of the resin was carried out at 50° C. for 24 hrs. Serial sections (120-200 sections per one sample), each 70 nm in thickness, were attached to formvar-coated nickel grids. Sections were incubated in 50 mM glycine for 5 minutes at room temperature. After rinsing with PBS, sections were incubated in 3% BSA for 30 minutes at room temperature. They were then incubated with the primary antibodies (rabbit polyclonal Prx II [LF-PA0091] and mouse monoclonal Flk-1 [sc-6251], diluted 1:100 in PBS) for 2 hrs at room temperature. After washing five times with Tween-PBS (PBS plus 0.5% Tween-20), sections were treated with the anti-rabbit or antimouse IgG+IgM antibodies conjugated with 20 nm- or 40 nm-diameter colloidal gold, respectively, (BE International, UK, diluted 1:20 in PBS) for 2 hours at room temperature. After washing three times with Tween-PBS, sections were washed three times with distilled water and stained with 4% uranyl acetate for 5 minutes and with lead citrate for 5 minutes. To examine the specificity of the primary antibody, treatment of sections were performed with the same procedure without the primary antibody. For double staining, primary and secondary antibody reactions were repeated for the second antigen. Finally, samples were observed with a Tecnai G2 Spirit Twin transmission electron microscope (FEI Company, USA) and a JEM ARM 1300S high-voltage electron microscope (JEOL, Japan).

Aortic Ring Assay

Thoracic aortic rings (1-mm thick) were placed on top of 250 μL of growth factor-reduced Matrigel (BD Bioscience cat #354230) and overlaid with 200 μL of EBM-2 containing 2% FBS with or without VEGF-A (25 ng/mL). The medium was replaced 3 times a week. Microvessel outgrowth was visualized by a time-lapse contrast microscopy and by a laser confocal microscopy after staining with FITC-conjugated BS-1 lectin (Sigma). The numbers of spouting vessels and branch points from each aortic ring were counted using Image-Pro Plus version 6.2 (Media Cybernetics).

Matrigel Plug Assay

Prx II$^{+/+}$ and Prx II$^{-/-}$ littermate mice (7-8 weeks old) were injected subcutaneously with 400 μL of Matrigel supplemented with 100 ng of VEGF-A. Each mouse received two Matrigel implants with VEGF-A and without VEFG-A. The mice were sacrificed 7 days later, and Matrigel plugs were carefully dissected and cleaned of surrounding adherent tissues. The plugs were photographed, with an Olympus Digital Still camera c-5060 for histological studies. The plugs were digested using 5 mL of Drabkin's reagent (Sigma) for measuring the hemoglobin content.

Animals and Treatment

The 8-week-old male Prx II$^{-/-}$ knockout mice and wild-type controls were bred in a pathogen free animal facility. All animal experiments were performed in compliance with the institutional guidelines (Ewha Womans University, Korea) for the care and use of laboratory animals. For a tumor xenograft model, the mice were anesthetized by inhalation of isoflurane gas, and then subcutaneously injected with B16F10 melanoma cells ($5 \times 10^5$ cells) or Lewis lung carcinoma (LLC) cells ($5 \times 10^5$ cells) suspended in 200 μL of PBS. After injection, the diameters of the growing tumors was measured using a caliper and then the volume was calculated according to the formula $V = a \times b^2 / 2$, wherein a and b denote the longer and shorter superficial diameters, respectively. The wound healing model was previously described in Cho, C. H. et al., (Proc Natl Acad Sci USA 2006 103 (13), 4946-4951). Briefly, the two full-thickness wounds were created on the back skin of each of five 8-week-old male Prx II knockout mice or wild-type control groups, using 4 mm skin biopsy punches (Stiefel Laboratories, Germany). The wounds were photographed with an SP-570UZ digital camera (Olympus). Skin-hole diameters (in mm) were calculated from wound perimeter tracings using photographic analysis with the ImageJ program (NIH). Wounds from at least five animals per time point were collected at 6 and 12 days after wounding.

Morphometric Analyses

The mice were anesthetized on the indicated days. Mouse tissues were fixed by systemic vascular perfusion with heparinized saline containing 1% paraformaldehyde in PBS, then removed and whole-mounted or embedded in OCT compound.

The frozen tissues were cross sectioned at 20 μm in thickness in a Cryo chamber (Leica). After blocking with 5% normal goat serum (Vector Laboratories) in PBST (0.3% Triton X-100 in PBS) for 1 hour at room temperature, the sectioned tissues were incubated overnight at 4° C. with an anti-mouse CD31 antibody, hamster clone 2H8 (Chemicon). After several PBST washes, the samples were incubated for 2 hours at room temperature with Cy3-conjugated anti-hamster IgG antibody (Jackson ImmunoResearch). For control experiments, the primary antibody was omitted. Fluorescent, signals were visualized and digital images were obtained on three random fields per tissue section at a screen magnification of ×100, each 1.25 mm² in area, using a LSM 510 Meta confocal microscope equipped with argon and helium-neon lasers (Carl Zeiss). The morphometric measurements of blood vessels were made on tissue sections with CD31+ pixels using photographic analysis with the ImageJ program (NIH).

Statistics

Data were analyzed by the Student's t-test on SigmaPlot 8.0 software, and statistical significance (P value) was determined. A P<0.05 was considered to be significant.

Results

Prx II Positively Regulates VEGF Signaling

The three known cytosolic antioxidant enzymes were found to be expressed in human aortic ECs (HAECs) (FIG. 11a). Thus, the present inventors examined which enzyme affects VEGF-mediated signaling in HAECs by using a small interfering RNA (siRNA)-mediated knockdown strategy. A set of four siRNAs targeting Prx I, Prx II, or GPxl efficiently reduced the expression of its target protein by 85-95% (FIG. 11a), When the three enzymes were knocked down by transfecting with at least two different siRNAs, the knockdown of Prx II expression only resulted in the reduction of protein tyrosine phosphorylation in response to VEGF when compared to that in control cells (FIG. 1a and FIGS. 11b and 11c). The Prx II knockdown also lowered the tyrosine phosphorylation throughout the VEGF treatment (FIG. 1b). In addition, neither of the other typical 2-cys Prxs, Prx III (mitochondrial form) and Prx IV (extracellular form), showed a similar effect on VEGF-induced tyrosine phosphorylation (FIGS. 11d and 11e). These results indicate that among cellular antioxidant enzymes the Prx II action is highly specific. Furthermore, the VEGF-induced tyrosine phosphorylation was also down-regulated by the Prx II knockdown in HUVECs and HMVEC, which generalizes the positive regulatory effect of Prx II on VEGF signaling among EC types (FIG. 12).

Next, the present inventors examined the activation of major VEGF-mediated signaling pathways. Of the five molecules examined, activation of endothelial nitric oxide synthase (eNOS) and a mitogen-activated protein kinase ERK were significantly down-regulated by the Prx II knockdown in HAECs compared to those in control cells (FIG. 1c and FIG. 13). Consistent with the reduced eNOS activation, the VEGF-induced cGMP production was also significantly reduced by the Prx II knockdown in HAECs (FIG. 1d). Since the ERK and eNOS activation sufficiently reduced the EC proliferation and/or migration in response to VEGF (FIG. 14), the present inventors performed the in vitro cell assays. Indeed, the Prx II knockdown led to a significant reduction of the proliferation, chemotactic migration, and further tube formation of HAECs in response to VEGF compared to those in control cells (FIGS. 1e-1g).

To ensure the selective effect, of Prx II on VEGF-VEGFR-2 signaling, the present inventors carried out several control experiments.

Firstly, the present inventors examined a mechanism that Prx II-regulated endogenous ROS regulates VEGFR phosphorylation in VECs. Considering that the VEGF165 used in this study binds to both VEGFR-1 and VEGFR-2 in VECs, and VEGFR-1 is known to be a decoy receptor for VEGF, the present inventors examined ROS-mediated VEGFR-1 expression in Prx II-depleted VECs. As a result, no difference was shown in the VEGFR-1 expression between the control group and Prx II-depleted VECs. In addition, Prx II knockdown had no effect on VEGF-dependent proliferation and migration of HAECs (FIGS. 15a-15d). This result indicates that VEGFR-1 was not involved in down-regulation of VEGF signaling by Prx II depletion.

Secondly, they examined the fibroblast growth factor-2 (FGF-2) belonging to the VEGF/PDGF family that strongly activates ERK in ECs. Indeed, FGF-2 induced marked activation of ERK in ECs as well as in fibroblasts, even though it poorly induced tyrosine phosphorylation (FIGS. 16a and 16b). Nonetheless, the Prx II knockdown did not impede ERK activation induced by FGF-2 in ECs (FIG. 16c).

Collectively, these results demonstrate that Prx II selectively regulates VEGF-VEGFR-2 signaling in ECs.

Prx II Protects VEGFR-2 Tyrosine Kinase from Oxidative Inactivation

Figure 2:
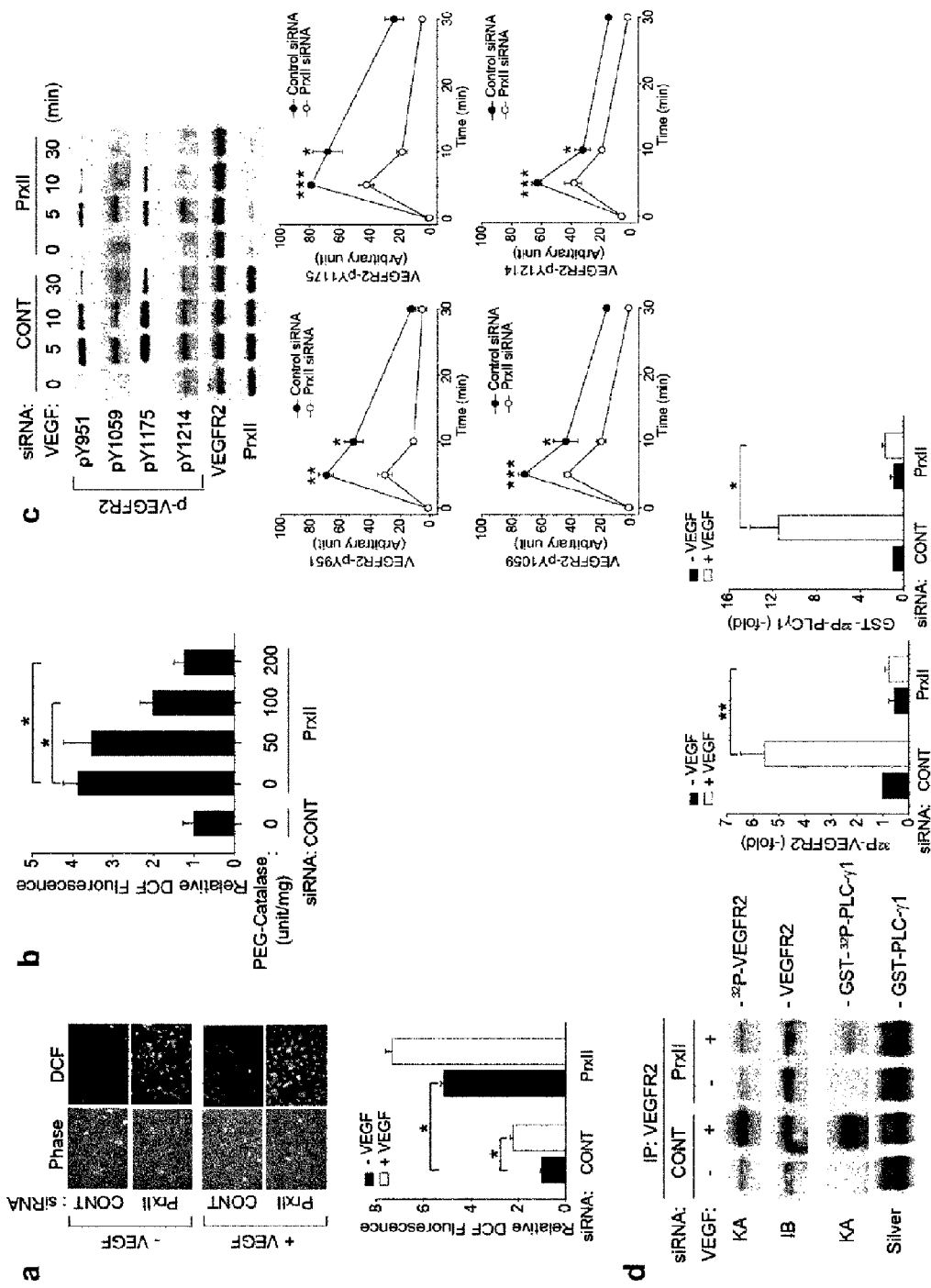
FIGS. 2-3 show that VEGFR-2 receptor tyrosine kinase is inactivated by $H_2O_2$.

Since this study dealt with the cytosolic peroxidase enzymes, the present inventors examined the change of intracellular ROS level in response to VEGF using an oxidant-sensitive fluorescent dye, 5,6)-chloromethyl-2',7'-dihydro-chlorofluorescein diacetate (CM-$H_2$DCFDA). Whereas VEGF treatment resulted in only a two-fold increase of ROS in control cells, the Prx II knockdown unexpectedly resulted in an approximately five-fold increase of basal ROS level (FIG. 2a). In contrast, neither Prx I nor GPxl affected in basal and VEGF-induced ROS production (FIG. 17). Furthermore, the introduction of catalase, an enzyme that reduces $H_2O_2$ to $H_2O$ in peroxisome, returned the level of ROS increased by the Prx II knockdown to the background level (FIG. 2b), which confirms that $H_2O_2$ was the actual substrate of Prx II. Thus, the results indicate that Prx II is a primary peroxidase enzyme suppressing the basal $H_2O_2$ level in HAECs. Thus, the results indicate that Prx II is a primary peroxidase enzyme suppressing the basal $H_2O_2$ level in HAECs.

Consequently, Prx II depletion increases the basal level of $H_2O_2$, but reduces VEGF-induced EC activation. This result is distinct, from the known fact that $H_2O_2$ production is required in VEGF-mediated signaling. To link these two outcomes induced by Prx II depletion, the present inventors first examined the level of VEGFR-2 autophosphorylation using the site-specific phosphoantibodies. As a result, the autophosphorylation of VEGFR-2 on all four known tyrosine residues induced by VEGF stimulation was appreciably reduced by the Prx II knockdown as compared to that of the control siRNA (FIG. 2c). A clear difference was observed in the phosphorylations of Y951 and Y1175 among the four tyrosine residues, and the same result occurred in HUVECs and HMVECs (FIG. 12), again confirming the positive regulatory role of Prx II in VEGF-VEGFR-2 signaling conserved between ECs.

As shown in the quantification of $^{125}$I-VEGF binding to VECs, since the Prx II knockdown did not alter the protein level and binding affinity of VEGF-VEGFR-2 in ECs, the present inventors reasoned that VEGFR-2 RTK activity may be impaired by $H_2O_2$ oxidation. Thus, they performed in vitro kinase assays using VEGFR-2 and GST-PLCγ1 as substrates. Notably, the VEGF-induced activation of VEGFR-2 RTK was almost completely abolished by the Prx II knockdown in HAECs compared to that in control cells (FIG. 2d). In contrast, endogenous PTPase activity was not affected by the knockdown of Prx II expression (FIG. 26).

Figure 3:
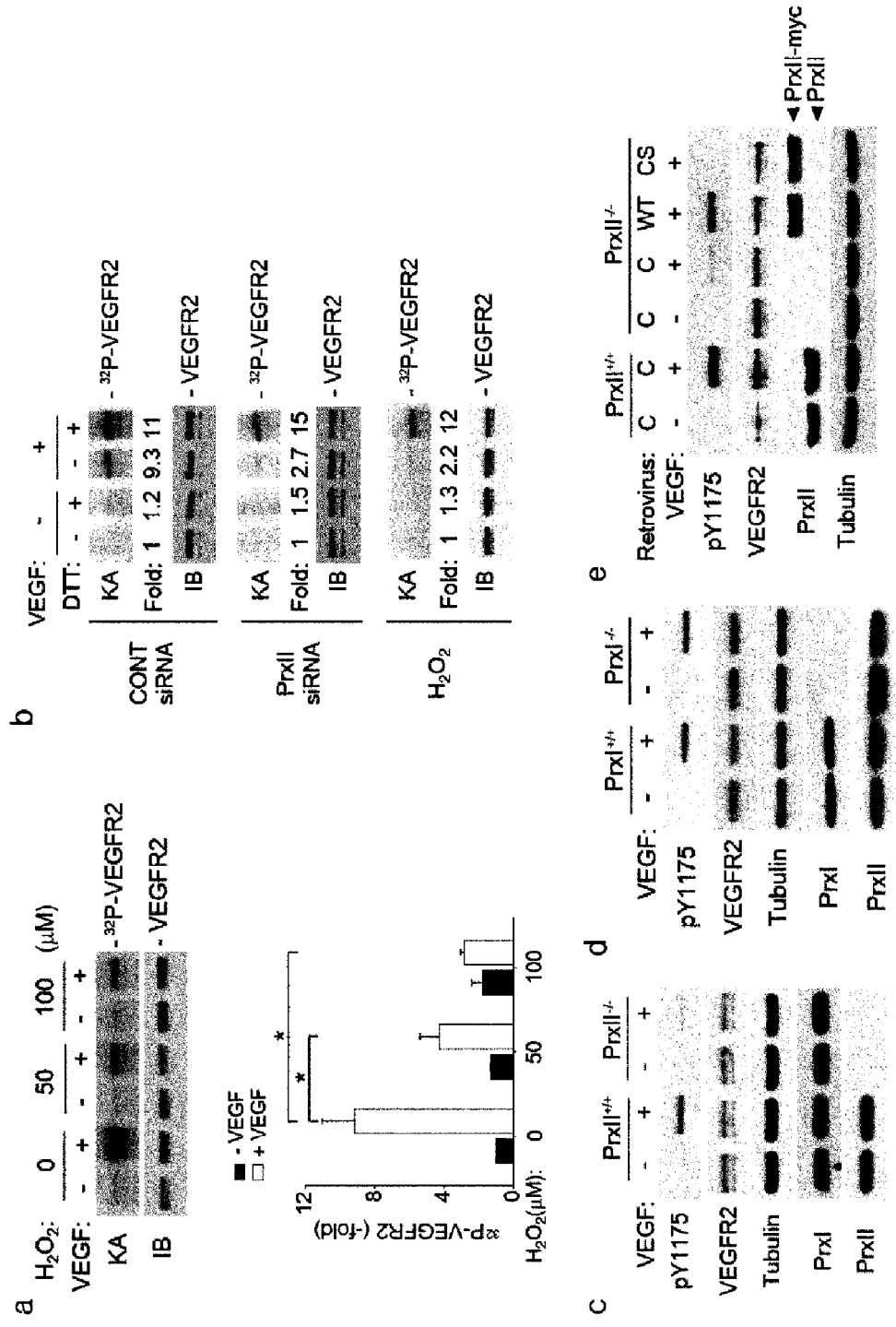

This result indicates that the elevated basal $H_2O_2$ impeded VEGFR-2 activation. To test whether it is possible with exogenous oxidant, the HAECs were directly treated with $H_2O_2$ solution at various concentrations. The pretreatment of $H_2O_2$ suppressed VEGF-dependent induction of VEGFR-2 RTK activation in a dose-dependent manner, as shown by in vitro kinase assay and VEGFR phosphorylation (FIGS. 3a and 18a). Since the 2-cys Prxs were shown to be inactivated by $H_2O_2$-mediated hyperoxidation in various cancer cells, the present inventors checked the oxidation state of Prx II using antibody specific to the hyper oxidized 2-cys Prxs (anti-Prx-$SO_2$ antibody). Exogenously-added $H_2O_2$ at micromolar concentrations up to 100 μM did not induce hyperoxidation of 2-cys Prxs (FIG. 18b). Even at millimolar concentration, $H_2O_2$ only slightly induced the hyperoxidation of Prx I and Prx III, but not Prx II. These data together demonstrate that exogenous $H_2O_2$ directly targets VEGFR2, not Prx II.

To further elucidate the chemical nature of VEGFR-2 oxidation, the VEGFR-2 was immunoprecipitated from HAECs either transfected with Prx II siRNA or treated with $H_2O_2$ and then incubated with the reducing agent dithiothreitol (DTT). As a result, DTT reduction fully restored the RTK activation that had been abolished by the Prx II knockdown or $H_2O_2$ treatment, which became similar to the activated RTK level in DTT-treated control sample (FIG. 3b). This result clearly indicates that the $H_2O_2$-mediated oxidation of VEGFR-2 is reversible.

To confirm in vivo the selective regulatory role of Prx II in endothelial VEGFR-2 signaling observed by RNA interference, the present inventors prepared the mouse aortic ECs (MAEC) from PrxI$^{-/-}$ and Prx II$^{--}$ mice. Consistent with the in vitro data, VEGFR-2 phosphorylation was markedly reduced in Prx II$^{-/-}$ MAECs, but not in Prx I$^{-/-}$ MAECs, compared to wild-type (WT) littermate cells (FIGS. 3c and 3d).

Moreover, when the Prx II$^{-/-}$ MAECs were rescued by an add-back expression of human Prx II, the wild-type Prx II restored VEGFR-2 activation in response to VEGF; whereas an inactive cysteine mutant of Prx II did not (FIG. 3e). This result indicates that, the peroxidase activity of Prx II is essential for protecting VEGFR-2 against, oxidation.

Cys1206 is the Site for Redox Regulation of VEGFR-2 RTK Activity

Figure 4:
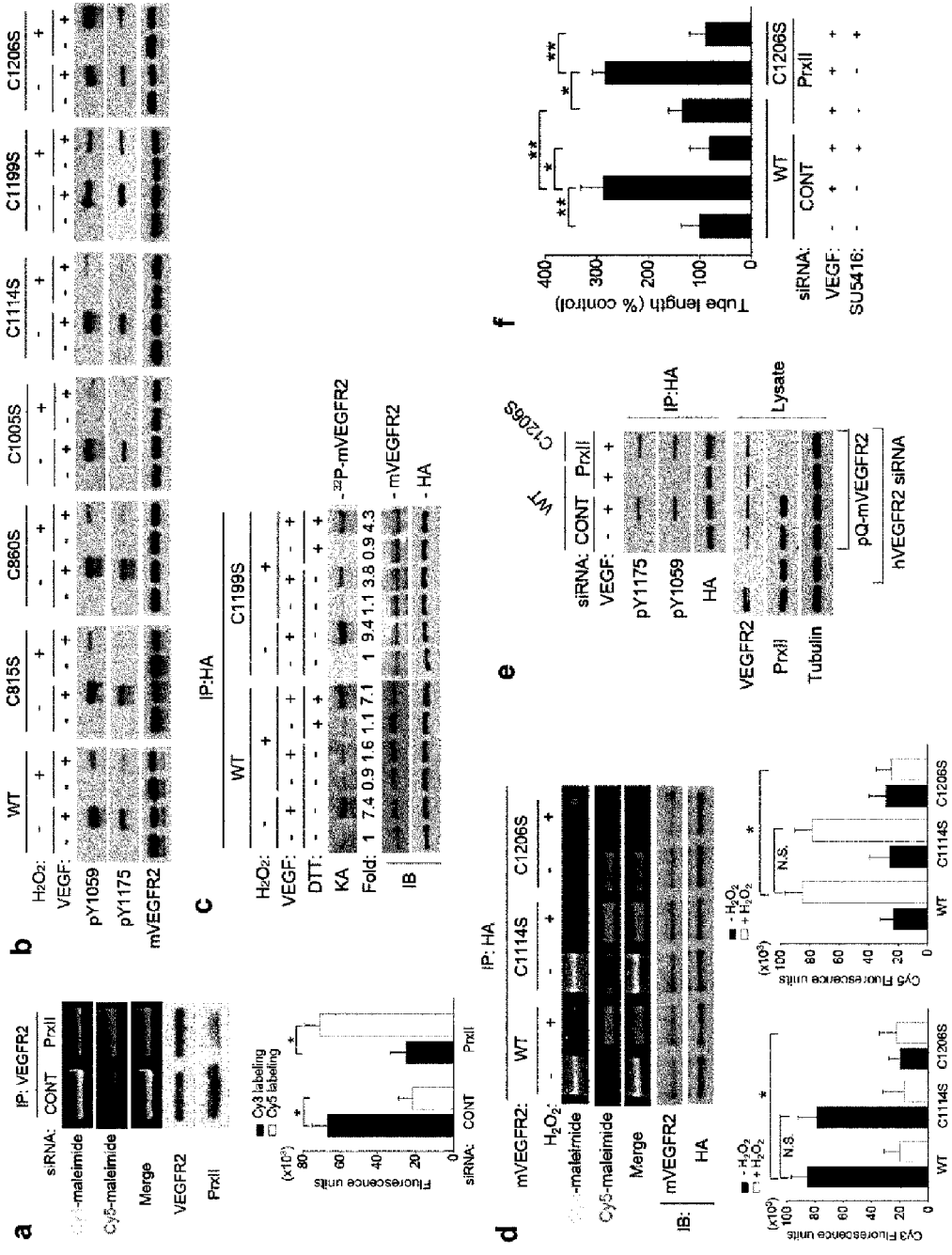
FIGS. 4-5 show that Cys1206 is responsible for oxidative inactivation of VEGFR2.

Because the redox regulation of a signaling protein or enzyme involves the $H_2O_2$-mediated oxidation of reactive cysteine residues contained therein, the present inventors tested whether this is the case for VEGFR-2 by differential fluorescence labeling of cysteine residues. The maleimide conjugated with fluorescent dyes (Cy3 and Cy5) was used for labeling the thiol group of reactive cysteine residues at neutral pH. The level of Cy3-maleimide labeling representing the extent of the reduced cysteine thiols was reduced by the Prx II knockdown; whereas the level of Cy5-maleimide representing the extent of the oxidized cysteine thiols was increased three-fold (FIG. 4a). This result briefly indicates the presence of reactive cysteine residue(s) in VEGFR2.

Considering that VEGF-VEGFR-2 interaction was unchanged by the Prx II knockdown, it was hypothesized that the reactive cysteine(s) must be in the cytoplasmic domain of VEGFR2. Therefore, the amino acid sequences of PDGFR/VEGFR/FGFR RTKs were aligned for searching the candidate cysteine residues present in the VEGFRs (FIG. 19a). The six cysteine residues including Cys815, Cys860, Cys1005, Cys1114, Cys1199 and Cys1206 (numbering in mouse VEGFR2) were uniquely found in the cytoplasmic domain of VEGFRs.

The Cys-to-Ser (CS) mutants of mouse VEGFR-2 (mVEGFR2) were produced and tested for susceptibility to the $H_2O_2$-mediated oxidation in 293T cells (FIG. 19b). The control experiment showed that the wild type (WT) of mVEGFR-2 expressed in 293T cells was inactivated by $H_2O_2$ in a dose-dependent manner (FIG. 19c) similar to the endogenous human VEGFR-2 in HAECs. The 293T cells expressing WT and CS mutants of mVEGFR-2 were pretreated with or without $H_2O_2$ and subsequently stimulated with VEGF. None of the cysteine mutations influenced VEGF-induced VEGFR-2 activation per se (FIG. 4b). Upon oxidative challenge, only C1206S mutant was completely resistant to $H_2O_2$-mediated inactivation, while the WT and the other CS mutants were sensitive to it (FIG. 4b). By quantifying the phosphorylation levels of VEGFR2-WT, -C1199S, and -C1206S, it was found that C1199S mutant partially responded to VEGF stimulation in the presence of $H_2O_2$. Therefore, the present inventors checked whether the oxidation of C1199S mutant is reversible. Unlike the WT, the RTK activity of the oxidized C1199S mutant was not restored by DTT reduction (FIG. 4c), suggesting that the Cys1199 residue is essential for reversibility of VEGFR-2 C1206 oxidation.

Figure 5:
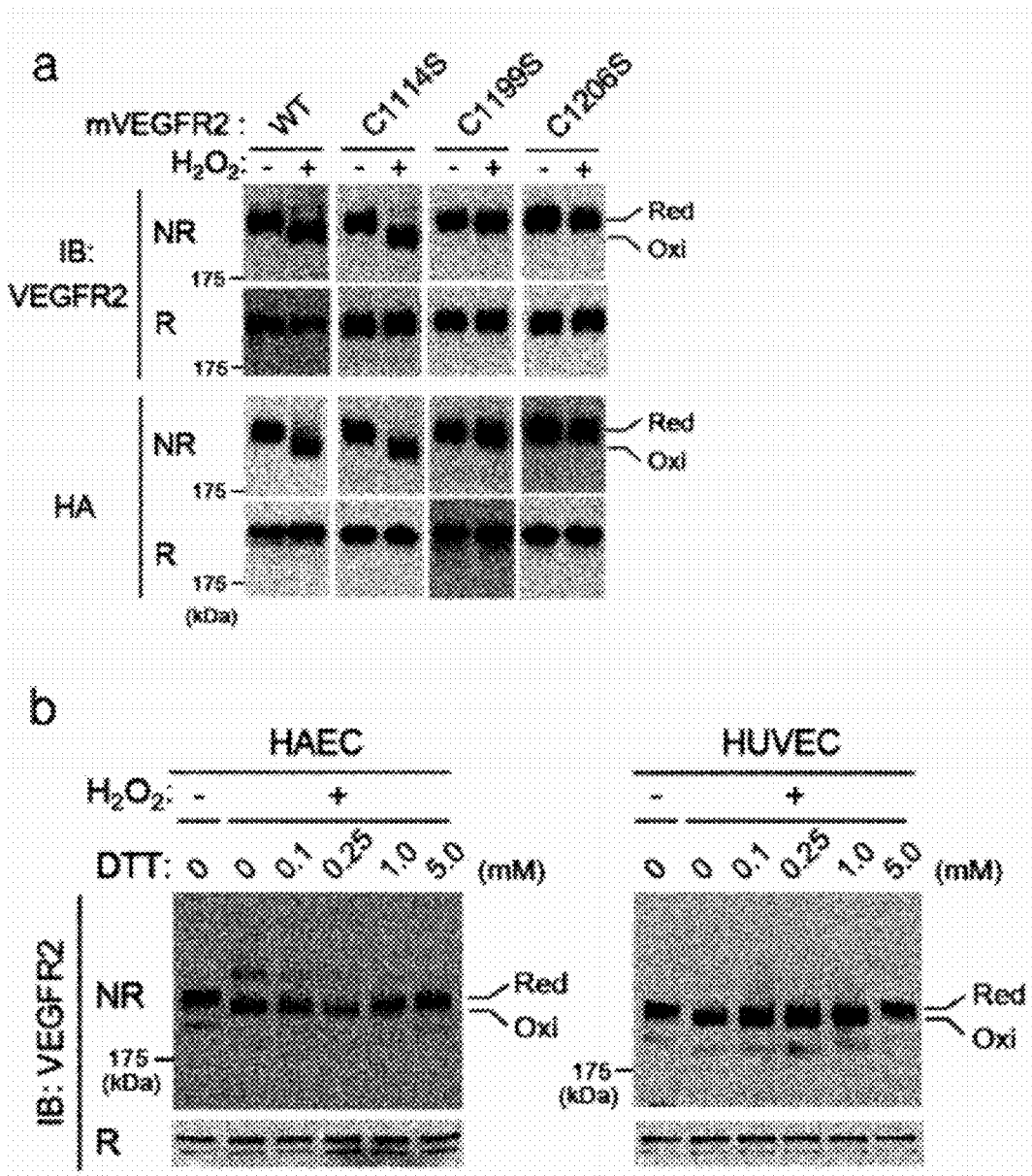

In order to demonstrate a scenario that the C1199 residue may act as a resolving residue that forms disulfide linkage with C1206-sulfenic acid (—SOH), electrophoretic mobility of mVEGFR-2 WT and CS mutants on a non-reduced denaturing gel was examined. When 293T cells expressing mVEGFR-2 protein were treated with exogenous $H_2O_2$, the mobilities of WT and C1144S mutants were faster than a non-treated sample (FIG. 5a). The same results are observed in the immunoblotting of mVEGFR-2 protein using HA-tag. Therefore, the above results indicate that the oxidized VEGFR-2 protein contained an intra-chain disulfide linkage. However, only C1199S and C1206S mutants did not show detectable change in mobility, indicating that the disulfide linkage is formed between C1206-sulfenic acid and Cys1199 residue in oxidized VEGFR2. in order to examine this in endogenous VEGFR2, the present inventors treated HAECs with exogenous $H_2O_2$. In immunoblotting analysis, the high-mobility form of VEGFR-2 was seen in the $H_2O_2$-treated sample, compared to the non-treated sample, indicating that it becomes a reduced form with the increasing concentrations of the reducing agent dithiothreitol (DTT) (FIG. 5b). There was no detectable band corresponding to the size of the VEGFR-2 dimer having an intra-chain disulfide linkage.

Moreover, the present inventors again carried out the fluorescent labeling of cysteine thiols in the mVEGFR-2 WT and CS mutants in order to validate that Cys1206 is the only reactive cysteine residue (FIG. 4d). Consistent with the result obtained from HAECs, the level of Cy3 labeling in the WT was reduced after $H_2O_2$ treatment and the level of Cy5 labeling was opposite. As expected, the C1114S mutant was essentially the same as the WT. In contrast, both Cy3 and Cy5 labeling in C1206S mutant was almost the baseline level. Thus, the data clearly indicate that Cys1206 is the only cysteine thiol reacting with maleimide as well as $H_2O_2$.

Next, the present inventors tested whether the C1206S mutant is functional in HAECs with the Prx II knockdown. The mVEGFR-2 WT and C1206S mutant were expressed in HAECs where endogenous human VEGFR-2 had been knocked down. Whereas the mVEGFR-2 WT was not activated by VEGF stimulation in HAECs with the Prx II knockdown, the C1206S mutant was activated as much as the WT was in control cells (FIG. 4e). Furthermore, the C1206S mutant effectively mediated VEGF-induced tube formation in HAECs with the Prx II knockdown just as the WT did in control stimulated cells (FIG. 4f). The tube formation by both VEGFR-2 WT and C1206S mutant was completely blocked by a VEGFR-2 RTK inhibitor SU5416, indicating that VEGFR-2 RTK activity was essential. Clearly, these results indicate that the C1206 residue is not involved in normal VEGFR-2 activation but in redox control of VEGFR-2 RTK activity as a direct oxidation site.

Prx II/VEGFR2/Nox4 are Spatially Co-Localized in Lipid Raft/Caveolae

Figure 6:
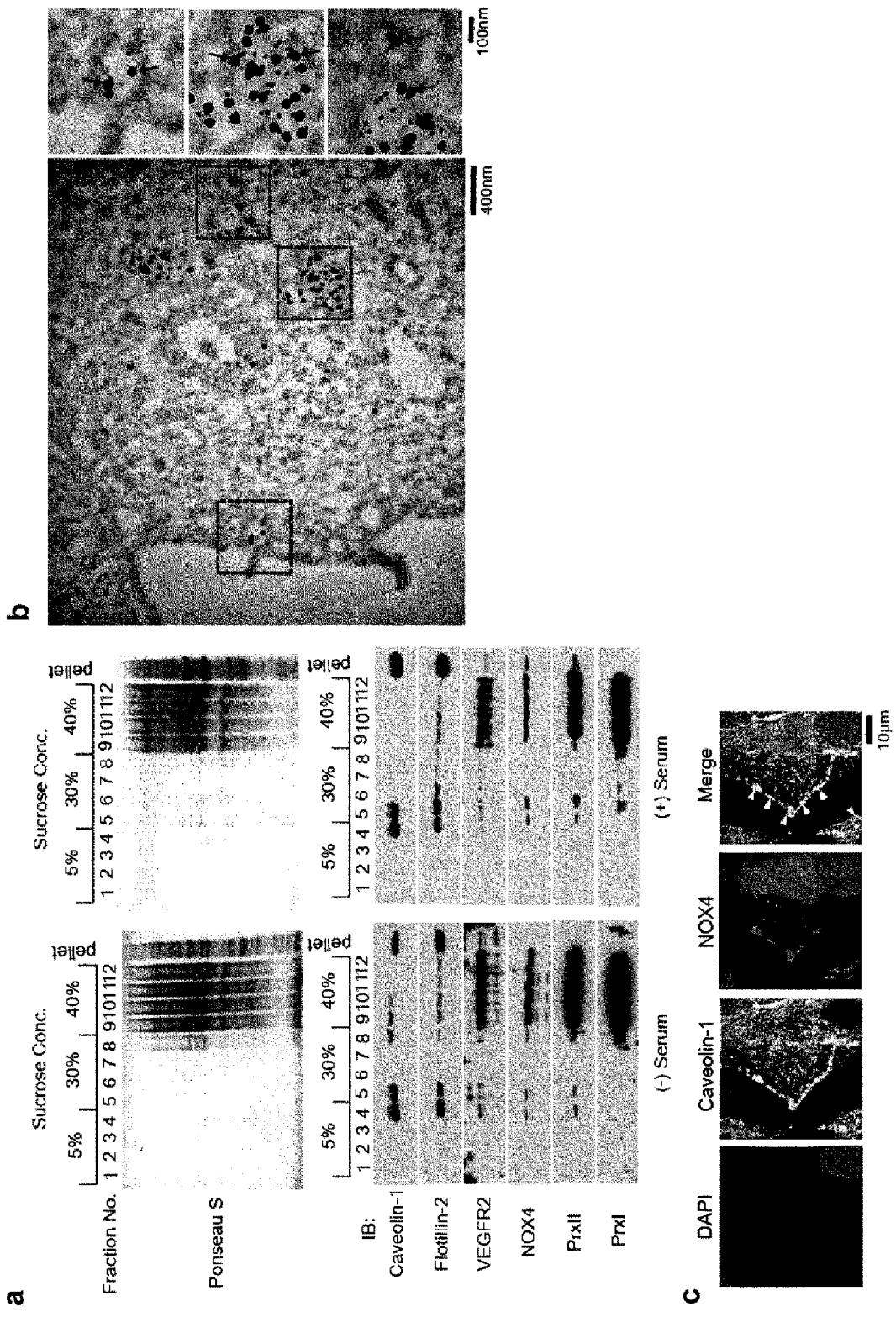
FIGS. 6-7 show that Prx II, VEGFR2, and NOX4 are co-localized in lipid raft/caveolae.

To understand the microenvironment. in which Prx II protects the VEGFR-2 against oxidation, the present inventors investigated the subcellular localization of Prx II and VEGFR-2 along with NOX enzyme as an $H_2O_2$ generator. Several previous studies have implicated that a portion of Prx II and VEGFR-2 is distributed in the lipid raft/caveolae of various cell types. To confirm this, they obtained the detergent-insoluble membranous fractions from HAECs grown in the absence and presence of serum supplemented with VEGF-A (FIG. 6a). The detergent-insoluble light fractions (fraction numbers 4 and 5) were enriched with the lipid raft/caveolae as indicated by marker proteins (caveolin-1 and flotillin-2). Indeed, a significant amount of Prx II and VEGFR-2 were detected in the lipid raft/caveolae fractions of ECs regardless of serum treatment (FIG. 6a). In contrast, Prx I appeared in the lipid raft/caveolae fractions after serum stimulation. To microscopically verify the membrane localization of the Prx II along with VEGFR2, they carried out an immunogold staining experiment with transmission electron microscopy. The Prx II was labeled with a secondary antibody containing 20-nm gold particles, whereas the VEGFR-2 was labeled with a secondary antibody containing 40-nm gold particles. Results showed that the two gold particles were found in the invaginated structures of the cell membrane as well as in the intracellular vesicular/vacuolar structures (FIG. 6b). Furthermore, most 40-nm particles were closely associated with one or two 20-nm particles, directly proving co-localization of Prx II and VEGFR-2 proteins. It is noteworthy that many of the Prx II molecules, known as a cytosolic protein, are found in the intracellular membranous structures in HAECs.

Next, the present inventors determined the subcellular distribution of NOX enzyme. The real-time PCR confirmed that the major NOX isoform in HAECs is NOX4, since its mRNA level was three orders of magnitude higher than those of other isoforms (FIG. 21a). Therefore, the present inventors produced NOX4-specific antibody to identify the location of NOX4. NOX 4 antibody specifically recognizes endogenous NOX4 proteins by immunoblotting and immunostaining (FIGS. 21b and 21c). Recently, a number of studies have shown that NOX4 is located in mitochondria and nuclei. Consistent with this, it was found that a large portion of NOX4 proteins was detected in the nuclei and perinuclear region at punctate fashion representing mitochondrial localization.

More importantly, the immunoreactive signals found in the plasma membrane were co-localized with caveolin-1 (FIG. 6c). This is new evidence showing the localization of NOX4 in lipid raft/caveolae.

Next, the present inventors investigated how these redox enzymes are correlated to each other in lipid raft/caveolae. When either NOX2 or NOX4 expression was knocked down together with Prx II in the HAECs, only the NOX4 knockdown returned the basal $H_2O_2$ level enhanced by the Prx II knockdown to the background level. This result indicates that NOX4 is the major producer of basal $H_2O_2$ in HAECs.

More definitively, the double knockdown of Prx II with NOX4, not NOX2, completely rescued VEGFR-2 activation in response to VEGF (FIG. 7b). it should be noted that the NOX2 knockdown resulted in a compensatory induction of NOX4 expression, which might cause an additional decrease of VEGFR-2 phosphorylation. Therefore, the results concluded that Prx II protects VEGFR-2 from the oxidation by NOX4-derived $H_2O_2$ in quiescent ECs. Then, to determine whether lipid raft/caveolae structure is crucial for such redox circuitry, caveolin-1 knockdown or cholesterol sequestration was used. When caveolin-1 was knocked down in HAECs, VEGFR-2 activation was no longer affected by the Prx II knockdown (FIG. 7c). The treatment of a cholesterol-binding agent, methyl-β-cyclodextrin (MβCD), also restored VEGFR-2 activation in HAECs with the Prx II knockdown at a level as good as those in the control cells (FIG. 4g). To further accentuate the role of Prx II in caveolae microdomain, the present inventors designed a displacement experiment in which an unrelated peroxidase, catalase, is targeted to various cellular compartments in Prx II-depleting ECs (FIG. 22a). For lipid raft/caveolae targeting, the peroxisomal targeting sequence (-KANL-COOH) at the C-terminus of catalase was replaced with the peptide sequence (6 amino acids) including a palmitoylation site and CAAX motif of H-Ras protein 22 (FIGS. 22b and 22c). When the Prx II knockdown cells were infected with these catalase-encoding adenoviruses, the cytosol- and membrane-targeted catalase, not the mitochondrial-targeted one, effectively eliminated the cellular $H_2O_2$ elevated by Prx II knockdown in a viral titer-dependent manner (FIGS. 7e and 23). However, when the VEGFR-2 activation was examined, the membrane-targeted catalase only rescued the VEGFR-2 activation lost by the Prx II knockdown in HAECs (FIG. 7f), indicating that independent of VEGF-induced $H_2O_2$ production for VEGF-mediated signaling, Prx II protects VEGFR-2 from the oxidation by NOX4-derived $H_2O_2$ in ECs regardless of VEGF stimulation, which is the localized action of $H_2O_2$ in lipid raft/caveolae microdomain.

Collectively, these data lead to the conclusion that the redox sensitivity of VEGFR-2 via unique Cys1206 residue is due to $H_2O_2$ derived from NOX4 present within caveolae, and therefore, protection by Prx II is crucial for VEGFR-2 activation in response to VEGF.

Deficiency of Prx II Suppresses Angiogenesis

Since the presence of Prx II was a prerequisite for VEGFR-2 activation, Prx II deficiency was assumed to negatively affect the VEGF-induced angiogenesis. To assess this, the present inventors first measured an angiogenic activity of Prx II$^{-/-}$ MAECs in ex vivo systems. The aortic ring assay was performed on Matrigel supplemented with or without VEGF. The microvascular endothelia were growing out of the aortic explants due to VEGF treatment, as identified with FITC-conjugated BS-1 lectin (FIG. 8a). The number of sprouts and branching points in the microvessels induced by VEGF treatment was significantly less in Prx II$^{-/-}$ aortic explants than those in WT explants (FIGS. 8b and 8c). This result indicates that Prx II deficiency impeded VEGF-dependent microvessel outgrowth. The angiogenic ability of MAECs was also examined in the Matrigel plugs subcutaneously implanted in WT and Prx II$^{-/-}$ mice. As represented by the amount of hemoglobin retained in the plugs, the VEGF-induced vessel formation in Prx II$^{-/-}$ mice was severely impaired compared to those in WT mice (FIG. 8d). This result was consistent with the amount of CD31$^+$ cells in the plugs.

Next, the present inventors examined the effect of Prx II deficiency on in vivo angiogenesis models. For cutaneous wounding, full-thickness excisional wounds were made in the back skins of WT and Prx II$^{-/-}$ mice. Wound closure was slower in skins of Prx II$^{-/-}$ mice than in WT mice (FIG. 8e). The CD31 staining of wounded area (at 6 days after injury) showed that the vessel density in the wounded edge was much less in Prx II$^{-/-}$ mice than the WT mice (FIG. 8f).

Since the cancer cells robustly produce VEGF to recruit angiogenic vessel and induce EC migration, leading to angiogenesis in cancer tissue, the present inventors tested the pro-angiogenic effect of Prx II in a tumor xenograft model. The Lewis lung carcinoma (LLC) and B16 melanoma cells were subcutaneously implanted into the WT and Prx II$^{-/-}$ mice. The tumor growth in Prx II$^{-/-}$ mice was slower than that in WT littermates, as evidenced by approximately 40-50% reduction in tumor volume and weight at three weeks after injection (FIGS. 9a and 9b). Moreover, when the vessel density was examined in the two week tumors of similar size (for LLC tumors, 165±42 mg in WT mice and 130±24 mg in Prx II$^{-/-}$ mice; for B16F10 tumors, 150±34 mg in WT mice and 100±26 mg in Prx II$^{-/-}$ mice), it was markedly less in the tumors grafted to Prx II$^{-/-}$ mice than WT littermates (FIGS. 9c and 9d), indicating that reduced angiogenic ability of Prx II$^{-/-}$ MAECs actually retarded tumor growth. To examine whether this tumor growth inhibition is caused by reduction of angiogenesis, immunofluorescence staining of the frozen sections of the collected tumor mass was performed using an endothelial cell marker CD31. A remarkable reduction of CD31$^+$ VEC was observed in the melanoma formed in Prx II$^{-/-}$ mouse, compared to that in the WT control group, indicating that Prx II-deficient endothelial cells do not migrate even though VEGF is secreted from the tumor tissue. That is, they show low reactivity to VEGF.

Collectively, the ex vivo and in vivo evidence strongly suggests that endothelial Prx II is a proangiogenic element that protects VEGFR-2 against oxidative inactivation, Screening of Angiogenesis Inhibitor Human aortic endothelial cells were cultured in a moist atmosphere containing 5% $CO_2$ at 37° C. When EC (HAEC) and SMC (HASMC) were used, they were cultured in EBM-2 and SmBM media, respectively. The cells cultured to passage 7 were treated with the test materials (e.g., chemical, peptide, or natural extract), and then incubated. Thereafter, the activity of Prx II protein and the expression of Prx II gene were analyzed in each cell. At this time, if the above described material inhibited, the activity or expression of Prx II, it was determined as an angiogenesis inhibitor.

In order to measure the changes in the activity of Prx II protein in vivo, the ROS levels were measured in the control cells and the test material-treated cells. Cells were then washed with Phenol Red free basal EBM (Lonza), and reacted with 5 μM 5,6-chloromethyl-2',7'-dichlorodihydrofluorescein diacetate (CM-H$_2$DCFDA) (Molecular Probe) at 37° C. for 5 minutes. The cells were washed with Phenol Red free EBM, and analyzed using a fluorescence microscope (Axiovert 200 Basic standard, Zeiss, Germany). If the activity of Prx II protein is reduced by the test material, the fluorescence level is increased in the test material-treated cells, compared to the control group. If the activity of Prx II protein is increased by the test material, the fluorescence level is reduced in the test material-treated cells. When the changes in the activity of Prx II protein were measured in vitro, each cell was homogenized in 20 mL of 20 mM HEPES-NaOH buffer solution (1 mM EDTA, 1 mM DTT, 1 mM AEBSF, pepstatin 1 μg/mL, leupeptin 5 μg/mL, aprotinin 5 μg/mL, pH 7.0). The homogenized suspension was centrifuged at 15,000×g and 4° C. for 30 minutes to collect the supernatant. The supernatant was mixed with DEAE-sepharose (200 μL resin) pre-equilibrated with buffer B (20 mM HEPES-NaOH, pH 7.0 and 1 mM EDTA) in a 1.5 mL centrifuge tube. The resin was washed twice with 1 mL of buffer B, and eluted with a linear gradient from 100 to 500 mM NaCl in buffer B to obtain fractions. Prx II was obtained by immunoblotting using antibodies against Prx II. 10 μg of the obtained Prx II was mixed with 2.5 μM yTrx1 (yeast-derived thioredoxin), 400 nM yTrxR (yeast-derived thioredoxin reductase), 200 μMNADPH, 1 mM EDTA, and 50 μL of a HEPES-NaOH buffer solution (50 mM; pH 6.0-8.0), and 100 μM $H_2O_2$ was added thereto. Subsequently, absorbance was monitored at 340 nm using an Agilent UV8453 spectrophotometer (Hewlett Packard, USA) at 30° C. for 3 minutes to measure NADPH oxidation. If the activity of Prx II protein is reduced by the test material, the absorbance is reduced in the test material-treated cells, compared to the control group. If the activity of Prx II protein is increased by the test material, the absorbance is increased in the test material-treated cells. In order to screen a material specifically inhibiting Prx II, steps (a) to (f) were further performed for Prx I, III, IV and V. If there was no difference in the absorbance between the control group and the experimental groups performed with Prx I, III, IV and V, the test material was determined as an angiogenesis inhibitor.

In order to measure the Prx II expression at a gene level, mRNAs were extracted from the control group and the test material-treated groups and each cDNA was synthesized. PCR well known in the art was performed using the synthesized cDNA as a template to detect the Prx II gene. The specificity and optimality of the PCR primer set were determined by BLAST (http://blast.ncbi.nlm.nih.gov/Blast.cgi) and oligonucleotide properties calculator (http://www.basic.northwestern.edu/biotools/oligocalc.html). PCR amplification was performed in 20 μL of reaction solution containing 1 μL of cDNA (10 ng), 10 mM Tris HCl (pH 9.0), 40 mM KCl, 250 dNTPs, 1U of Taq polymerase, 1.5 mM MgCl$_2$ and 10 pmole of each primer. PCR reaction conditions include initial denaturation at 95° C. for 5 minutes, 25-30 cycles of denaturation at 95° C. for 30 seconds, annealing at 58-65° C. for 30 seconds, extension at 72° C. for 30 seconds, and additional extension at 72° C. for 7 minutes. PCR amplification was performed in a PTC-220 DNA Engine Dyad PCR Cycler (MJ Research Inc., Waltham, Mass., USA). The PCR product was electrophoresed on a 2% SeaKem LE agarose gel (FMC Bioproducts, Philadelphia, Pa., USA), and visualized by EtBr staining. If the Prx II expression is increased by the test material, the PCR product of Prx II is increased in the test material-treated cells, compared to the control group. If the Prx II expression is reduced by the test material, the PCR product of Prx II is reduced in the test material-treated cells.

In order to measure the Prx II expression at a protein level, the culture media were aspirated at the appropriate time, and the control cells and the test material-treated cells were lysed in an extraction buffer containing 20 nM Hepes (pH 7.0), 1% Triton X-100, 150 mM NaCl, 10% glycerol, 1 mM EDTA, 2 mM EGTA, 1 mM DTT, 5 mM $Na_3VO_4$, 5 mM KaF, 1 mM AEBSF, aprotinin (5 μg/mL), and leupeptin (5 μg/mL). The protein content of each sample was quantified using the Bradford reagent (Bio-Rad). 15 μg was taken from each sample, and electrophoresed on a 10% SDS polyacrylamide gel (SDS-PAGE). The separated protein was transferred from the gel onto nitrocellulose membrane using a tris-glycine buffer. In order to block non-specific binding, the membrane was reacted with TBS (Tris-buffered saline; TBST) containing 0.5% Tween-20 and 5% nonfat milk at room temperature for 1 hour. The above described blots were reacted with each primary antibody in TBST containing 5% nonfat milk or BSA at 4° C. for overnight. After washing with TBST the blots were reacted with horseradish peroxidase-conjugated goat anti-mouse immunoglobulin (IgG; 1:5000 dilution) or goat anti-rabbit IgG (1:3000 dilution) at room temperature for 45 minutes. Prx II protein bands were detected using an Amersham ECLTM detection system (GE healthcare). For standardization of the detected signals, the immunoblots were stripped by shaking them for 60 minutes at 37° C. in 67 mM Tris (pH 6.7), 2% SDS, 100 mM 2-mercaptoethanol and reprobed with a tubulin antibody. If the amount of Prx II protein is increased by the test material, the strength of the Prx II band is increased in the test material-treated cells, compared to the control group. If the amount of Prx II protein is reduced by the test material, the strength of the Prx II band is reduced in the test material-treated cells, compared to the control group.

The specific embodiments of the present invention were described in detail, and it will be apparent by a person having an ordinary skill in the art that the detailed descriptions are only preferred embodiments and the scope of the present invention is not limited thereto. Therefore, the scope of the present invention should be determined by the accompanying claims and their equivalents.

Effect of the Invention

Features and advantages of the present invention can be summarized as follows:
(a) According to the present invention, an inhibitor of Prx II gene expression or Prx II protein activity increases oxidative inactivation of VEGF receptor tyrosine kinase (RTK), thereby reducing VEGF signaling.
(b) a novel angiogenesis inhibitor can be screened using the inhibitor of Prx II gene expression or Prx II protein activity.
(c) therefore, the method of the present invention can be used for the prevention or treatment of various diseases, ailments, and conditions related to angiogenesis.

What is claimed is:

1. A method for inhibiting angiogenesis in a vascular endothelial cell of a subject, comprising administering to said subject an inhibitor of Prx II (peroxiredoxin II), wherein said inhibitor is selected from the group consisting of an antisense oligonucleotide, an siRNA and an aptamer, and wherein said inhibitor inhibits angiogenesis in said vascular endothelial cell.

2. The method according to claim 1, wherein said inhibitor reduces VEGF-A (vascular endothelial growth factor A) induced activation of VEGFR-2 (vascular endothelial growth factor receptor:-2).

3. The method according to claim 1, wherein said inhibitor increases oxidative inactivation of VEGFR-2.

4. The method according to claim 1, wherein said subject suffers from an angiogenesis related-disease selected from the group consisting of: cancer, diabetic retinopathy, retinopathy of prematurity, corneal transplant rejection, neovascular glaucoma, erythrosis, proliferative retinopathy, psoriasis, hemophilic arthropathy, capillary proliferation in atherosclerotic plaques, keloid, wound granulation, vascular adhesions, rheumatoid arthritis, ostarthritis, autoimmune diseases, Crohn's disease, restenosis, atherosclerosis, intestinal adhesions, ulcer, cirrhosis, glomerulonephritis, diabetic nephropathy, malignant nephrosclerosis, thrombotic microangiopathy, organ-transplant rejection, glomerulopathy, diabetes, inflammatory diseases or neurodegenerative diseases.

5. The method according to claim 1, wherein said inhibitor inhibits proliferation of said vascular endothelial cell.

6. The method according to claim 1, wherein said inhibitor inhibits migration of said vascular endothelial cell.

7. The method according to claim 1, wherein said siRNA is selected from the group consisting of SEQ ID NOs. 1 to 4.

8. The method according to claim 1, wherein said inhibitor increases the intracellular level of $H_2O_2$.

9. The method according to claim 1, wherein said subject has a cancer selected from the group consisting of: brain cancer, neuroendocrine carcinoma, gastric cancer, lung cancer, breast cancer, ovarian cancer, liver cancer, bronchial cancer, nasopharyngeal cancer, laryngeal cancer, pancreatic cancer, bladder cancer, adrenal gland cancer, colorectal cancer, colon cancer, cervical cancer, prostate cancer, bone cancer, skin cancer, thyroid cancer, parathyroid cancer and ureter cancer.

* * * * *

SEQUENCE LISTING

```
<160> NUMBER OF SEQ ID NOS: 41

<210> SEQ ID NO 1
<211> LENGTH: 21
<212> TYPE: RNA
<213> ORGANISM: Artificial Sequence
<220> FEATURE:
<223> OTHER INFORMATION: siRNA for human PrxII

<400> SEQUENCE: 1
cgcuugucug aggauuacgu u                                          21

<210> SEQ ID NO 2
<211> LENGTH: 21
<212> TYPE: RNA
<213> ORGANISM: Artificial Sequence
<220> FEATURE:
<223> OTHER INFORMATION: siRNA for human PrxII

<400> SEQUENCE: 2
aggaauauuu cuccaaacau u                                          21

<210> SEQ ID NO 3
<211> LENGTH: 21
<212> TYPE: RNA
<213> ORGANISM: Artificial Sequence
<220> FEATURE:
<223> OTHER INFORMATION: siRNA for human PrxII

<400> SEQUENCE: 3
gacgcuuguc ugaggauuau u                                          21

<210> SEQ ID NO 4
<211> LENGTH: 21
<212> TYPE: RNA
<213> ORGANISM: Artificial Sequence
<220> FEATURE:
<223> OTHER INFORMATION: siRNA for human PrxII

<400> SEQUENCE: 4
```
ucaaagaggu gaagcugucu u          21

<210> SEQ ID NO 5
<211> LENGTH: 21
<212> TYPE: RNA
<213> ORGANISM: Artificial Sequence
<220> FEATURE:
<223> OTHER INFORMATION: siRNA for human Prx I

<400> SEQUENCE: 5
acucaacugc caagugauuu u          21

<210> SEQ ID NO 6
<211> LENGTH: 21
<212> TYPE: RNA
<213> ORGANISM: Artificial Sequence
<220> FEATURE:
<223> OTHER INFORMATION: siRNA for human Prx I

<400> SEQUENCE: 6
ccacggagau cauugcuuuu u          21

<210> SEQ ID NO 7
<211> LENGTH: 21
<212> TYPE: RNA
<213> ORGANISM: Artificial Sequence
<220> FEATURE:
<223> OTHER INFORMATION: siRNA for human Prx I

<400> SEQUENCE: 7
ggucaauaca ccuaagaaau u          21

<210> SEQ ID NO 8
<211> LENGTH: 21
<212> TYPE: RNA
<213> ORGANISM: Artificial Sequence
<220> FEATURE:
<223> OTHER INFORMATION: siRNA for human Prx I

<400> SEQUENCE: 8
uaugccagau ggucaguuuu u          21

<210> SEQ ID NO 9
<211> LENGTH: 21
<212> TYPE: RNA
<213> ORGANISM: Artificial Sequence
<220> FEATURE:
<223> OTHER INFORMATION: siRNA for human GPx1

<400> SEQUENCE: 9
gcaagguacu acuuaucgau u          21

<210> SEQ ID NO 10
<211> LENGTH: 21
<212> TYPE: RNA
<213> ORGANISM: Artificial Sequence
<220> FEATURE:
<223> OTHER INFORMATION: siRNA for human GPx1

<400> SEQUENCE: 10
ugaauucccu caaguacguu u          21

<210> SEQ ID NO 11
<211> LENGTH: 21
<212> TYPE: RNA

```
<213> ORGANISM: Artificial Sequence
<220> FEATURE:
<223> OTHER INFORMATION: siRNA for human GPx1

<400> SEQUENCE: 11
ggagaacgcc aagaacgaau u                                              21

<210> SEQ ID NO 12
<211> LENGTH: 21
<212> TYPE: RNA
<213> ORGANISM: Artificial Sequence
<220> FEATURE:
<223> OTHER INFORMATION: siRNA for human GPx1

<400> SEQUENCE: 12
gcaaccaguu ugggcaucau u                                              21

<210> SEQ ID NO 13
<211> LENGTH: 19
<212> TYPE: RNA
<213> ORGANISM: Artificial Sequence
<220> FEATURE:
<223> OTHER INFORMATION: siRNA for human NOX4

<400> SEQUENCE: 13
gucaacaucc agcuguacc                                                 19

<210> SEQ ID NO 14
<211> LENGTH: 21
<212> TYPE: RNA
<213> ORGANISM: Artificial Sequence
<220> FEATURE:
<223> OTHER INFORMATION: siRNA for human caveolin-1

<400> SEQUENCE: 14
gcaucaacuu gcagaaagau u                                              21

<210> SEQ ID NO 15
<211> LENGTH: 27
<212> TYPE: DNA
<213> ORGANISM: Artificial Sequence
<220> FEATURE:
<223> OTHER INFORMATION: Sense primer for human Prx II

<400> SEQUENCE: 15
ccgctcgaga tggcctccgg taacgcg                                        27

<210> SEQ ID NO 16
<211> LENGTH: 26
<212> TYPE: DNA
<213> ORGANISM: Artificial Sequence
<220> FEATURE:
<223> OTHER INFORMATION: Antisense primer for human Prx II

<400> SEQUENCE: 16
cgggatccct aattgtgttt ggagaa                                         26

<210> SEQ ID NO 17
<211> LENGTH: 20
<212> TYPE: DNA
<213> ORGANISM: Artificial Sequence
<220> FEATURE:
<223> OTHER INFORMATION: Sense primer for human VEGFR-1

<400> SEQUENCE: 17
atttgtgatt ttggccttgc                                                20
```

<210> SEQ ID NO 18
<211> LENGTH: 21
<212> TYPE: DNA
<213> ORGANISM: Artificial Sequence
<220> FEATURE:
<223> OTHER INFORMATION: Antisense primer for human VEGFR-1

<400> SEQUENCE: 18
caggctcatg aacttgaaag c                                           21

<210> SEQ ID NO 19
<211> LENGTH: 20
<212> TYPE: DNA
<213> ORGANISM: Artificial Sequence
<220> FEATURE:
<223> OTHER INFORMATION: Sense primer for human VEGFR2

<400> SEQUENCE: 19
gtgaccaaca tggagtcgtg                                             20

<210> SEQ ID NO 20
<211> LENGTH: 20
<212> TYPE: DNA
<213> ORGANISM: Artificial Sequence
<220> FEATURE:
<223> OTHER INFORMATION: Antisense primer for human VEGFR2

<400> SEQUENCE: 20
ccagagattc catgccactt                                             20

<210> SEQ ID NO 21
<211> LENGTH: 20
<212> TYPE: DNA
<213> ORGANISM: Artificial Sequence
<220> FEATURE:
<223> OTHER INFORMATION: Sense primer for GAPDH

<400> SEQUENCE: 21
ttcattgacc tcaactacat                                             20

<210> SEQ ID NO 22
<211> LENGTH: 20
<212> TYPE: DNA
<213> ORGANISM: Artificial Sequence
<220> FEATURE:
<223> OTHER INFORMATION: Antisense primer for GAPDH

<400> SEQUENCE: 22
gaggggccat ccacagtctt                                             20

<210> SEQ ID NO 23
<211> LENGTH: 21
<212> TYPE: DNA
<213> ORGANISM: Artificial Sequence
<220> FEATURE:
<223> OTHER INFORMATION: Sense primer for beta-actin

<400> SEQUENCE: 23
tggatcagca agcaggagta t                                           21

<210> SEQ ID NO 24
<211> LENGTH: 18
<212> TYPE: DNA
<213> ORGANISM: Artificial Sequence
<220> FEATURE:

<223> OTHER INFORMATION: Antisense primer for beta-actin

<400> SEQUENCE: 24
gcatttgcgg tggcagat                                                     18

<210> SEQ ID NO 25
<211> LENGTH: 40
<212> TYPE: DNA
<213> ORGANISM: Artificial Sequence
<220> FEATURE:
<223> OTHER INFORMATION: Sense primer for mVEGFR2

<400> SEQUENCE: 25
aatcacgcgg ccgcaccatg gagagcaagg cgctgctagc                             40

<210> SEQ ID NO 26
<211> LENGTH: 35
<212> TYPE: DNA
<213> ORGANISM: Artificial Sequence
<220> FEATURE:
<223> OTHER INFORMATION: Antisense primer for mVEGFR2

<400> SEQUENCE: 26
aatcacctcg agaacaggag gtgagcgcag tgtgg                                  35

<210> SEQ ID NO 27
<211> LENGTH: 39
<212> TYPE: DNA
<213> ORGANISM: Artificial Sequence
<220> FEATURE:
<223> OTHER INFORMATION: primer for C815S site-specific mutation

<400> SEQUENCE: 27
ttgcccttgg atgagcgctc tgaacgcttg ccttatgat                              39

<210> SEQ ID NO 28
<211> LENGTH: 36
<212> TYPE: DNA
<213> ORGANISM: Artificial Sequence
<220> FEATURE:
<223> OTHER INFORMATION: primer for C860S site-specific mutation

<400> SEQUENCE: 28
gacaagacag cgacttccaa aacagtagcc gtcaag                                 36

<210> SEQ ID NO 29
<211> LENGTH: 39
<212> TYPE: DNA
<213> ORGANISM: Artificial Sequence
<220> FEATURE:
<223> OTHER INFORMATION: primer for C1005S site-specific mutation

<400> SEQUENCE: 29
accttggagc atctcatctc ttacagcttc caagtggct                              39

<210> SEQ ID NO 30
<211> LENGTH: 49
<212> TYPE: DNA
<213> ORGANISM: Artificial Sequence
<220> FEATURE:
<223> OTHER INFORMATION: primer for C1114S site-specific mutation

<400> SEQUENCE: 30
gggtcaagat tgatgaagaa ttttctagga gattgaaaga aggaactag                   49

-continued

```
<210> SEQ ID NO 31
<211> LENGTH: 42
<212> TYPE: DNA
<213> ORGANISM: Artificial Sequence
<220> FEATURE:
<223> OTHER INFORMATION: primer for C1199S site-specific mutation

<400> SEQUENCE: 31
gcctacctca cctgtttcct ctatggagga agaggaagtg tg                           42

<210> SEQ ID NO 32
<211> LENGTH: 44
<212> TYPE: DNA
<213> ORGANISM: Artificial Sequence
<220> FEATURE:
<223> OTHER INFORMATION: primer for C1206S site-specific mutation

<400> SEQUENCE: 32
gtatggagga agaggaagtg tccgacccca aattccatta tgac                         44

<210> SEQ ID NO 33
<211> LENGTH: 23
<212> TYPE: DNA
<213> ORGANISM: Artificial Sequence
<220> FEATURE:
<223> OTHER INFORMATION: Sense primer for human Cat-Cyto

<400> SEQUENCE: 33
ggggtaccat ggctgacagc cgg                                                23

<210> SEQ ID NO 34
<211> LENGTH: 23
<212> TYPE: DNA
<213> ORGANISM: Artificial Sequence
<220> FEATURE:
<223> OTHER INFORMATION: Antisense primer for human Cat-Cyto

<400> SEQUENCE: 34
gcggcaaggg agtaatctag agc                                                23

<210> SEQ ID NO 35
<211> LENGTH: 21
<212> TYPE: DNA
<213> ORGANISM: Artificial Sequence
<220> FEATURE:
<223> OTHER INFORMATION: Sense primer for human Cat-Mito

<400> SEQUENCE: 35
cccaagcttg ctgacagccg g                                                  21

<210> SEQ ID NO 36
<211> LENGTH: 42
<212> TYPE: DNA
<213> ORGANISM: Artificial Sequence
<220> FEATURE:
<223> OTHER INFORMATION: Antisense primer for human Cat-Caax

<400> SEQUENCE: 36
gcggcaaggg agtgcaagtg tgtgctctcc taatctagaa ac                           42

<210> SEQ ID NO 37
<211> LENGTH: 1039
<212> TYPE: DNA
<213> ORGANISM: Homo sapiens

<400> SEQUENCE: 37
```

```
gctcgtccgc tccctccccc gcgccgtgca cgtcttggtt cgggccgggc ataaaaggct    60
tcgcggccca gggctcactt ggcgctgaga acgcgggtcc acgcgtgtga tcgtccgtgc   120
gtctagcctt tgcccacgca gctttcagtc atggcctccg gtaacgcgcg catcggaaag   180
ccagcccctg acttcaaggc cacagcggtg gttgatggcg ccttcaaaga ggtgaagctg   240
tcggactaca agggaagta cgtggtcctc ttttctacc ctctggactt cacttttgtg    300
tgccccaccg agatcatcgc gttcagcaac cgtgcagagg acttccgcaa gctgggctgt   360
gaagtgctgg gcgtctcggt ggactctcag ttcacccacc tggcttggat caacaccccc   420
cggaaagagg gaggcttggg cccctgaac atccccctgc ttgctgacgt gaccagacgc    480
ttgtctgagg attacggcgt gctgaaaaca gatgagggca ttgcctacag gggcctcttt   540
atcatcgatg caagggtgt ccttcgccag atcactgtta atgatttgcc tgtgggacgc    600
tccgtggatg aggctctgcg gctggtccag gccttccagt acacagacga gcatggggaa   660
gtttgtcccg ctggctggaa gcctggcagt gacacgatta gcccaacgt ggatgacagc    720
aaggaatatt tctccaaaca caattaggct ggctaacgga tagtgagctt gtgccctgc    780
ctaggtgcct gtgctgggtg tccacctgtg cccccacctg ggtgccctat gctgacccag   840
gaaaggccag acctgcccct ccaaactcca cagtatggga ccctggaggg ctaggccaag   900
gccttctcat gcctccacct agaagctgaa tagtgacgcc ctcccccaag cccacccagc   960
cgcacacagg cctagaggta accaataaag tattagggaa aggtgtgaaa aaaaaaaaa   1020
aaaaaaaaaa aaaaaaaa                                                1039

<210> SEQ ID NO 38
<211> LENGTH: 1042
<212> TYPE: DNA
<213> ORGANISM: Homo sapiens

<400> SEQUENCE: 38
actctcgcga gatccctact ggctataaag gcagcgcccc ggagagctct tgcgcgtctt    60
gttcttgcct ggtgtcggtg gttagtttct gcgacttgtg ttgggactgc tgataggaag   120
atgtcttcag gaaatgctaa aattgggcac cctgccccca acttcaaagc cacagctgtt   180
atgccagatg gtcagtttaa agatatcagc ctgtctgact acaaaggaaa atatgttgtg   240
ttcttctttt accctcttga cttcaccttt gtgtgcccca cggagatcat tgctttcagt   300
gatagggcag aagaatttaa gaaactcaac tgccaagtga ttggtgcttc tgtggattct   360
cacttctgtc atctagcatg ggtcaataca cctaagaaac aaggaggact gggacccatg   420
aacattcctt tggtatcaga cccgaagcgc accattgctc aggattatgg ggtcttaaag   480
gctgatgaag gcatctcgtt cagggccctt tttatcattg atgataaggg tattcttcgg   540
cagatcactg taaatgacct ccctgttggc cgctctgtgg atgagacttt gagactagtt   600
caggccttcc agttcactga caaacatggg gaagtgtgcc cagctggctg gaaacctggc   660
agtgatacca tcaagcctga tgtccaaaag agcaaagaat atttctccaa gcagaagtga   720
gcgctgggct gttttagtgc caggctgcgg tgggcagcca tgagaacaaa acctcttctg   780
tatttttttt ttccattagt aaaacacaag acttcagatt cagccgaatt gtggtgtctt   840
acaaggcagg cctttcctac aggggtgga gagaccagcc tttcttcctt tggtaggaat    900
ggcctgagtt ggcgttgtgg gcaggctact ggtttgtatg atgtattagt agagcaaccc   960
attaatcttt tgtagtttgt attaaacttg aactgagacc ttgatgagtc tttaaaaaaa  1020
aaaaaaaaaa aaaaaaaaaa aa                                           1042
```

<210> SEQ ID NO 39
<211> LENGTH: 1591
<212> TYPE: DNA
<213> ORGANISM: Homo sapiens

<400> SEQUENCE: 39

```
ccctgcgtct ctgcccgccc cgtggcgccc gagtgcactg aagatggcgg ctgctgtagg      60
acggttgctc cgagcgtcgg ttgcccgaca tgtgagtgcc attccttggg gcatttctgc     120
cactgcagcc ctcaggcctg ctgcatgtgg aagaacgagc ttgacaaatt tattgtgttc     180
tggttccagt caagcaaaat tattcagcac cagttcctca tgccatgcac ctgctgtcac     240
ccagcatgca ccctatttta agggtacagc cgttgtcaat ggagagttca aagacctaag     300
ccttgatgac tttaagggga aatatttggt gcttttcttc tatcctttgg atttcacctt     360
tgtgtgtcct acagaaattg ttgcttttag tgacaaagct aacgaatttc acgacgtgaa     420
ctgtgaagtt gtcgcagtct cagtggattc cactttagc catcttgcct ggataaatac     480
accaaggaag aatggtggtt tgggccacat gaacatcgca ctcttgtcag acttaactaa     540
gcagatttcc cgagactacg gtgtgctgtt agaaggttct ggtcttgcac taagaggtct     600
cttcataatt gaccccaatg gagtcatcaa gcatttgagc gtcaacgatc tcccagtggg     660
ccgaagcgtg gaagaaaccc tccgcttggt gaaggcgttc cagtatgtag aaacacatgg     720
agaagtctgc ccagcgaact ggacaccgga ttctcctacg atcaagccaa gtccagctgc     780
ttccaaagag tactttcaga aggtaaatca gtagatcacc catgtgtatc tgcaccttct     840
caactgagag aagaaccaca gttgaaacct gcttttatca ttttcaagat ggttatttgt     900
agaaggcaag gaaccaatta tgcttgtatt cataagtatt actctaaatg ttttgttttt     960
gtaattctgg ctaagacctt ttaaacatgg ttagttgcta gtacaaggaa tcctttattg    1020
gtaacatctt ggtggctggc tagctagttt ctacagaaca taatttgcct ctatagaagg    1080
ctattcttag atcatgtctc aatggaaaca ctcttctttc ttagccttac ttgaatcttg    1140
cctataataa agtagagcaa cacacattga aagcttctga tcaacggtcc tgaaattttc    1200
atcttgaatg tctttgtatt aaactgaatt ttcttttaag ctaacaaaga tcataatttt    1260
caatgattag ccgtgtaact cctgcaatga atgtttatgt gattgaagca aatgtgaatc    1320
gtattatttt aaaaagtggc agagtgactt aactgatcat gcatgatccc tcatccctga    1380
aattgagttt atgtagtcat tttacttatt ttattcatta gctaactttg tctatgtata    1440
tttctagata ttgattagtg taatcgatta taaaggatat ttatcaaatc cagggattgc    1500
attttgaaat tataattatt ttctttgctg aagtattcat tgtaaaacat acaaaataaa    1560
catattttaa aacatttgca ttttaccacc a                                   1591
```

<210> SEQ ID NO 40
<211> LENGTH: 921
<212> TYPE: DNA
<213> ORGANISM: Homo sapiens

<400> SEQUENCE: 40

```
gcggcgctcg cgccaaggga cgtgtttctg cgctcgcgtg gtcatggagg cgctgccgct      60
gctagccgcg acaactccgg accacggccg ccaccgaagg ctgcttctgc tgccgctact     120
gctgttcctg ctgccggctg gagctgtgca gggctgggag acagaggaga ggccccggac     180
tcgcgaagag gagtgccact ctacgcgggg tggacaagtg tacccgggag aggcatcccg     240
```

```
ggtatcggtc gccgaccact ccctgcacct aagcaaagcg aagatttcca agccagcgcc      300
ctactgggaa ggaacagctg tgatcgatgg agaatttaag gagctgaagt taactgatta      360
tcgtgggaaa tacttggttt tcttcttcta cccacttgat ttcacatttg tgtgtccaac      420
tgaaattatc gcttttggcg acagacttga agaattcaga tctataaata ctgaagtggt      480
agcatgctct gttgattcac agtttaccca tttggcctgg attaataccc ctcgaagaca      540
aggaggactt gggccaataa ggattccact tctttcagat ttgacccatc agatctcaaa      600
ggactatggt gtatacctag aggactcagg ccacactctt agaggtctct tcattattga      660
tgacaaagga atcctaagac aaattactct gaatgatctt cctgtgggta gatcagtgga      720
tgagacacta cgtttggttc aagcattcca gtacactgac aaacacggag aagtctgccc      780
tgctggctgg aaacctggta gtgaaacaat aatcccagat ccagctggaa agctgaagta      840
tttcgataaa ctgaattgag aaatacttct tcaagttatg atgcttgaaa gttctcaata      900
aagttcacgg tttcattacc a                                               921

<210> SEQ ID NO 41
<211> LENGTH: 827
<212> TYPE: DNA
<213> ORGANISM: Homo sapiens

<400> SEQUENCE: 41
gcagtggagg cggcccaggc ccgccttccg cagggtgtcg ccgctgtgcc gctagcggtg       60
ccccgcctgc tgcggtggca ccagccagga ggcggagtgg aagtggccgt ggggcgggta      120
tgggactagc tggcgtgtgc gccctgagac gctcagcggg ctatatactc gtcggtgggg      180
ccggcggtca gtctgcggca gcggcagcaa gacggtgcag tgaaggagag tgggcgtctg      240
gcggggtccg cagtttcagc agagccgctg cagccatggc cccaatcaag gtgggagatg      300
ccatcccagc agtggaggtg tttgaagggg agccaggaa caaggtgaac ctggcagagc      360
tgttcaaggg caagaagggt gtgctgtttg gagttcctgg ggccttcacc cctggatgtt      420
ccaaggttcg gctcctggct gatcccactg ggcctttgg gaaggagaca gacttattac      480
tagatgattc gctggtgtcc atctttggga atcgacgtct caagaggttc tccatggtgg      540
tacaggatgg catagtgaag gccctgaatg tggaaccaga tggcacaggc ctcacctgca      600
gcctggcacc caatatcatc tcacagctct gaggccctgg gccagattac ttcctccacc      660
cctccctatc tcacctgccc agccctgtgc tggggccctg caattggaat gttggccaga      720
tttctgcaat aaacacttgt ggtttgcggc caaaaaaaaa aaaaaaaaa aaaaaaaaa        780 aaaaaaaaaa aaaaaaaaaa aaaaaaaaaa aaaaaaaaa aaaaaaa                    827
```